(12) United States Patent
Martin

(10) Patent No.: US 11,849,938 B2
(45) Date of Patent: *Dec. 26, 2023

(54) VARIABLE DENIER YARN AND SUTURE

(71) Applicant: Syntorr Inc., Palo Alto, CA (US)

(72) Inventor: Daniel L. Martin, Palo Alto, CA (US)

(73) Assignee: SYNTORR INC., Palo Alto, CA (US)

( * ) Notice: Subject to any disclaimer, the term of this patent is extended or adjusted under 35 U.S.C. 154(b) by 64 days.

This patent is subject to a terminal disclaimer.

(21) Appl. No.: 17/710,780

(22) Filed: Mar. 31, 2022

(65) Prior Publication Data

US 2022/0401098 A1 Dec. 22, 2022

Related U.S. Application Data

(63) Continuation of application No. 17/473,868, filed on Sep. 13, 2021, now Pat. No. 11,712,241, which is a
(Continued)

(51) Int. Cl.
*A61B 17/06* (2006.01)
*D04C 1/12* (2006.01)
(Continued)

(52) U.S. Cl.
CPC .......... *A61B 17/06166* (2013.01); *D04B 1/22* (2013.01); *D04B 21/202* (2013.01);
(Continued)

(58) Field of Classification Search
CPC A61B 2017/06171; A61B 2017/06185; A61B 2017/00526; A61B 17/06166
See application file for complete search history.

(56) References Cited

U.S. PATENT DOCUMENTS

| 650,984 A | 6/1900 | McConnell |
|---|---|---|
| 1,860,030 A | 5/1932 | Hinchliff |

(Continued)

FOREIGN PATENT DOCUMENTS

| EP | 0459914 | 12/1991 |
|---|---|---|
| EP | 0472260 | 2/1992 |

(Continued)

OTHER PUBLICATIONS

Fontanazza, Maria. Expanding Medical Textiles: Q&A with Biomedical Structures CEO Dean Tulmaris; published on Orthotec (http://www.orthotec.com) on Jan. 9, 2012, 4 pages.

*Primary Examiner* — Diane D Yabut
*Assistant Examiner* — Christina C Lauer
(74) *Attorney, Agent, or Firm* — MURABITO, HAO & BARNES LLP

(57) ABSTRACT

A method of suturing includes: (1) wrapping a first segment of a suture through a traction loop; (2) pulling the traction loop and the first segment through an opening in a suture lock; (3) continuing to pull the traction loop such that a second segment of the suture extends through the opening, wherein the second segment has a greater denier than the first segment such that the second segment more nearly fills an entire dimension of the opening than the first segment; and (4) locking the suture in place with the second segment in the opening.

33 Claims, 52 Drawing Sheets

Related U.S. Application Data continuation of application No. 14/537,719, filed on Nov. 10, 2014, now Pat. No. 11,116,498, which is a continuation-in-part of application No. 13/354,204, filed on Jan. 19, 2012, now Pat. No. 8,881,635.

(60) Provisional application No. 61/542,990, filed on Oct. 4, 2011, provisional application No. 61/453,453, filed on Mar. 16, 2011, provisional application No. 61/438,880, filed on Feb. 2, 2011.

(51) Int. Cl.
| | | |
|---|---|---|
| *D04B 1/22* | (2006.01) | |
| *D04B 21/20* | (2006.01) | |
| *A61B 17/00* | (2006.01) | |
| *A61F 2/06* | (2013.01) | |

(52) U.S. Cl.
CPC ...... *D04C 1/12* (2013.01); *A61B 2017/00526* (2013.01); *A61B 2017/06171* (2013.01); *A61B 2017/06185* (2013.01); *A61F 2/06* (2013.01); *A61F 2002/065* (2013.01); *D10B 2509/04* (2013.01)

(56) References Cited

U.S. PATENT DOCUMENTS

| | | | |
|---|---|---|---|
| 2,020,197 | A | 11/1935 | Franz |
| 2,064,074 | A | 12/1936 | McNamee |
| 2,213,720 | A | 9/1940 | Seim |
| 2,257,953 | A | 10/1943 | Haskell |
| 3,357,171 | A | 12/1967 | Marshall |
| 3,568,277 | A | 3/1971 | Mattingly |
| 3,568,278 | A | 3/1971 | Mattingly |
| 3,587,221 | A | 6/1971 | Buzano |
| 3,738,125 | A | 6/1973 | Blezard et al. |
| 3,748,874 | A | 7/1973 | Blezard |
| 3,926,194 | A | 12/1975 | Greenberg et al. |
| 4,321,854 | A | 3/1982 | Foote et al. |
| 4,621,638 | A | 11/1986 | Silverstrini |
| 4,643,178 | A | 2/1987 | Nastari et al. |
| 4,917,699 | A | 4/1990 | Chervitz |
| 5,147,400 | A | 9/1992 | Kaplan et al. |
| 5,341,632 | A | 8/1994 | Jung et al. |
| 5,645,568 | A | 7/1997 | Jung et al. |
| 5,699,657 | A | 12/1997 | Paulson |
| 6,045,571 | A | 4/2000 | Hill et al. |
| 6,134,923 | A | 10/2000 | Lay et al. |
| 6,296,659 | B1* | 10/2001 | Foerster ............. A61B 17/0469 623/13.13 |
| 6,716,234 | B2 | 4/2004 | Grafton et al. |
| 6,994,719 | B2 | 2/2006 | Grafton |
| 7,070,858 | B2 | 7/2006 | Shalaby et al. |
| 7,329,271 | B2 | 2/2008 | Koyfman et al. |
| 7,601,165 | B2 | 10/2009 | Stone |
| 7,845,262 | B2 | 12/2010 | Ueda |
| 8,881,635 | B2 | 11/2014 | Martin |
| 9,107,653 | B2 | 8/2015 | Sullivan |
| 9,855,029 | B2 | 1/2018 | Sullivan |
| 9,867,607 | B2 | 1/2018 | Sullivan |
| 11,116,498 | B2* | 9/2021 | Martin ..................... D04C 1/12 |
| 2002/0029066 | A1 | 3/2002 | Foerster |
| 2004/0199208 | A1 | 10/2004 | Foerster |
| 2005/0192581 | A1 | 9/2005 | Molz et al. |
| 2005/0192631 | A1 | 9/2005 | Grafton |
| 2006/0155328 | A1 | 7/2006 | Foerster |
| 2006/0259076 | A1 | 11/2006 | Burkhart et al. |
| 2007/0213770 | A1 | 9/2007 | Dreyfuss |
| 2007/0239209 | A1 | 10/2007 | Fallman |
| 2008/0046094 | A1 | 2/2008 | Han et al. |
| 2008/0082128 | A1 | 4/2008 | Stone |
| 2008/0312689 | A1 | 12/2008 | Denham et al. |
| 2009/0318961 | A1 | 12/2009 | Stone et al. |
| 2009/0318962 | A1 | 12/2009 | Spedden et al. |
| 2010/0016892 | A1 | 1/2010 | Kaiser et al. |
| 2010/0211075 | A1 | 8/2010 | Stone |
| 2010/0256677 | A1 | 10/2010 | Albertorio et al. |
| 2010/0268273 | A1 | 10/2010 | Albertorio et al. |
| 2012/0053630 | A1 | 3/2012 | Denham et al. |
| 2012/0197294 | A1 | 8/2012 | Martin |
| 2012/0239145 | A1 | 9/2012 | Peterson et al. |
| 2014/0052178 | A1 | 2/2014 | Dooney, Jr. |
| 2014/0052179 | A1 | 2/2014 | Dreyfuss et al. |
| 2014/0121700 | A1 | 5/2014 | Dreyfuss et al. |
| 2015/0066081 | A1 | 3/2015 | Martin |
| 2022/0008069 | A1 | 1/2022 | Martin |
| 2022/0218341 | A1* | 7/2022 | Martin ............. A61B 17/06166 |

FOREIGN PATENT DOCUMENTS

| | | |
|---|---|---|
| EP | 1623726 | 2/2006 |
| EP | 1690500 | 8/2006 |
| EP | 2698117 | 2/2014 |
| EP | 2724673 A1 | 4/2014 |
| GB | 2468307 | 9/2010 |
| JP | 07324242 | 12/1995 |
| JP | 09031783 | 2/1997 |
| JP | 10280238 | 10/1998 |
| JP | 2004149940 | 5/2004 |
| WO | 9622682 | 8/1996 |
| WO | 2010105171 | 9/2010 |

* cited by examiner

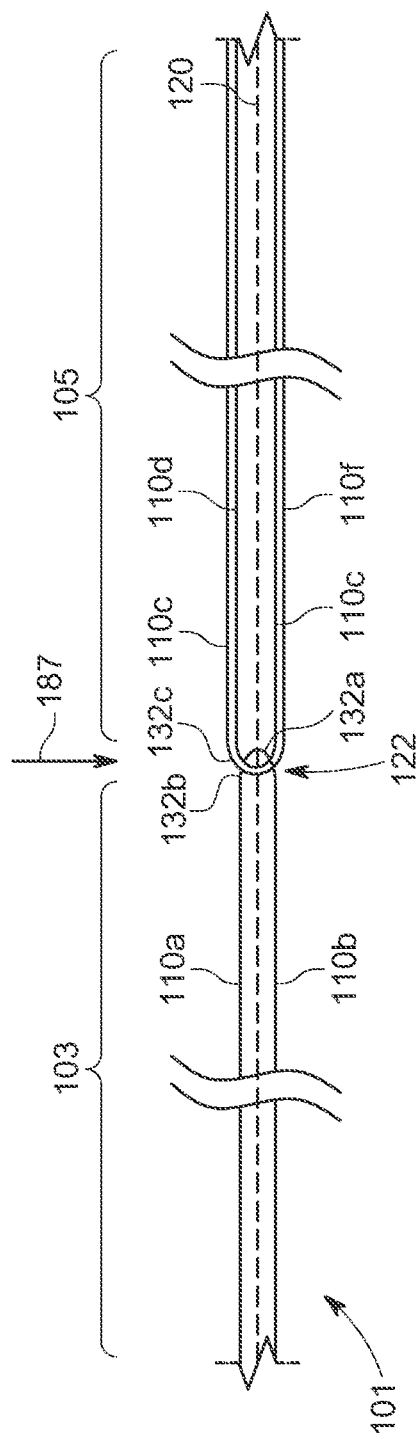
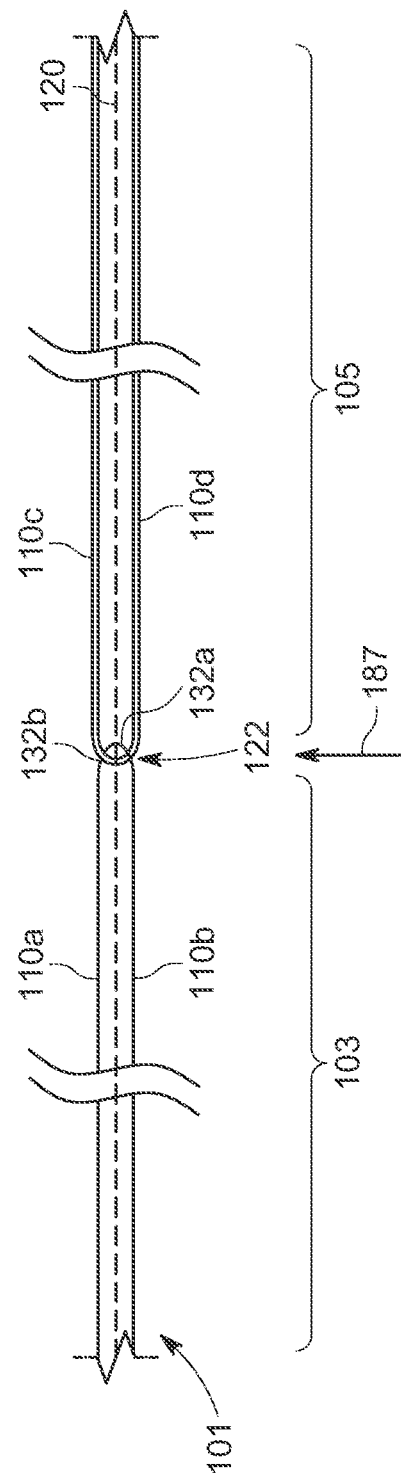

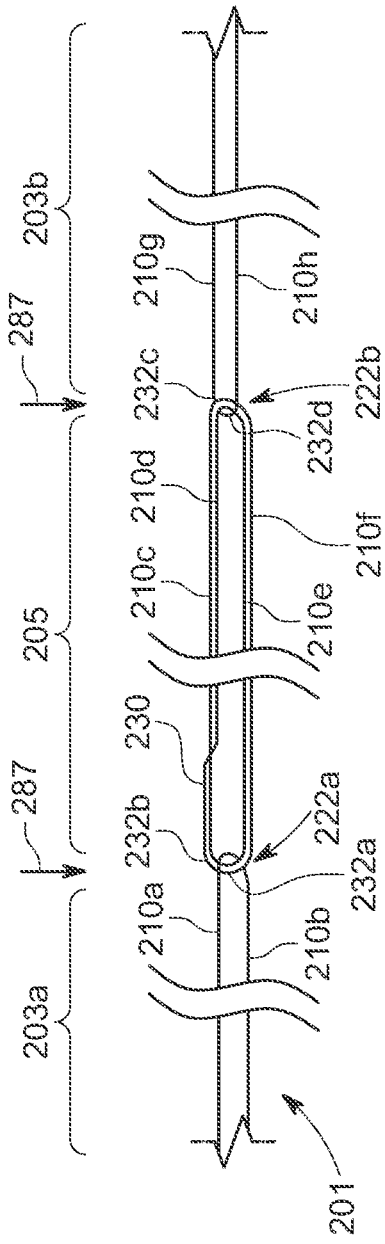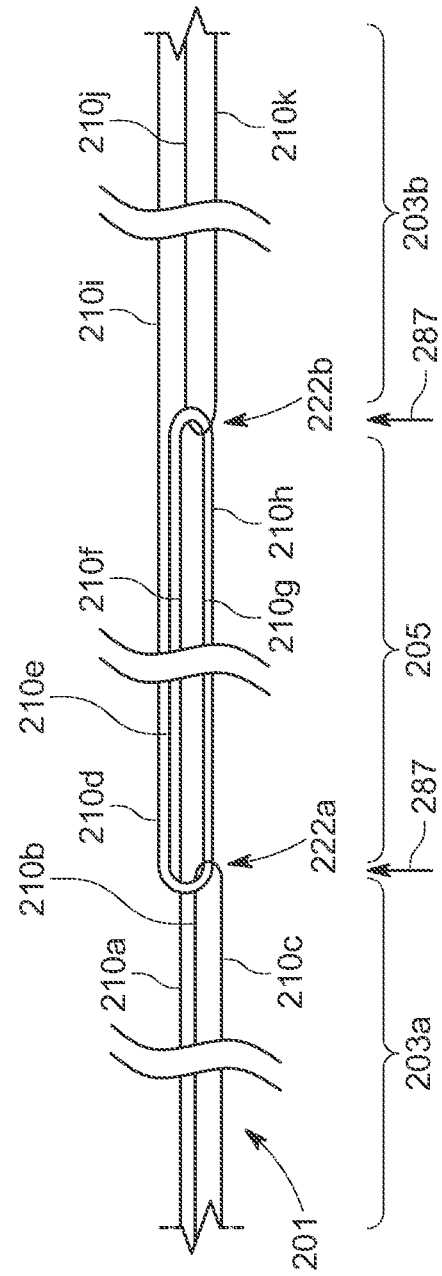

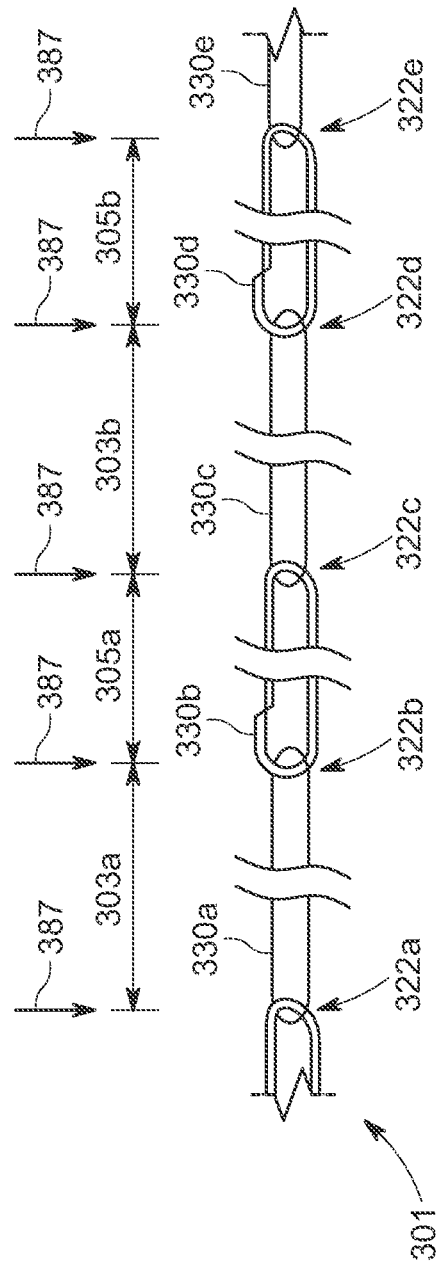
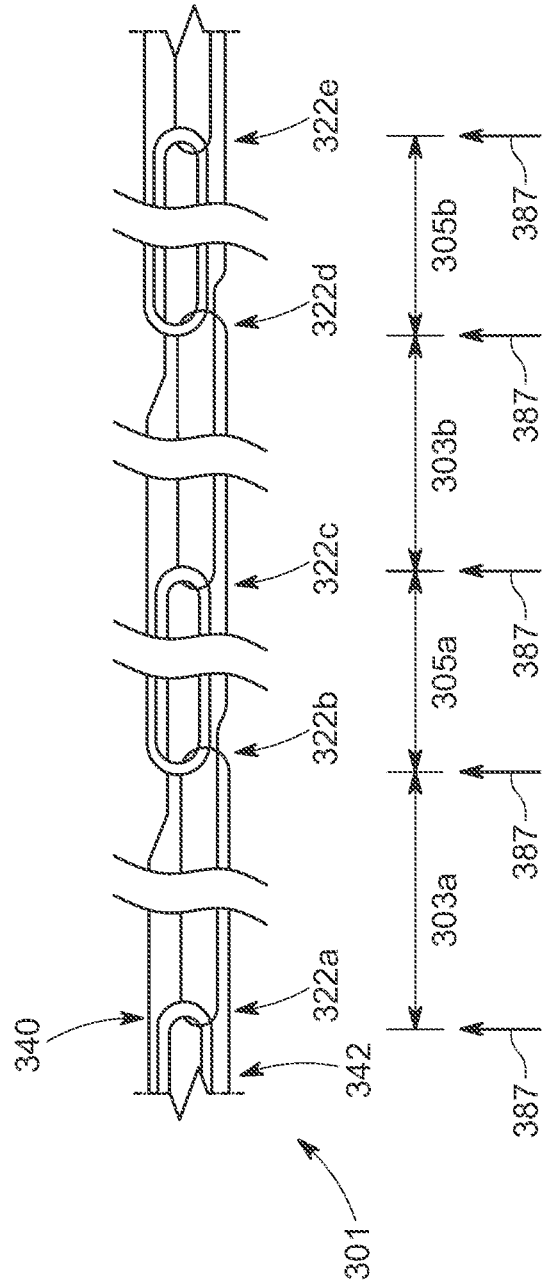
FIG. 3A
FIG. 3B

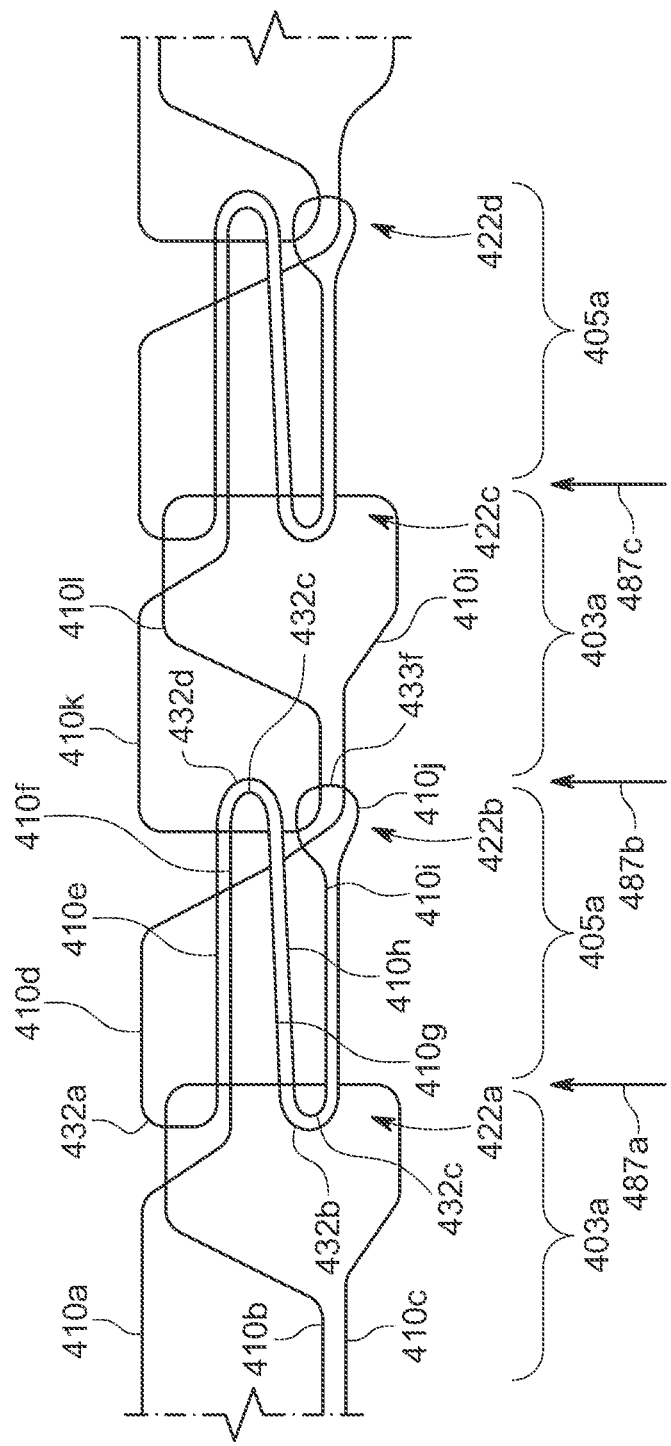

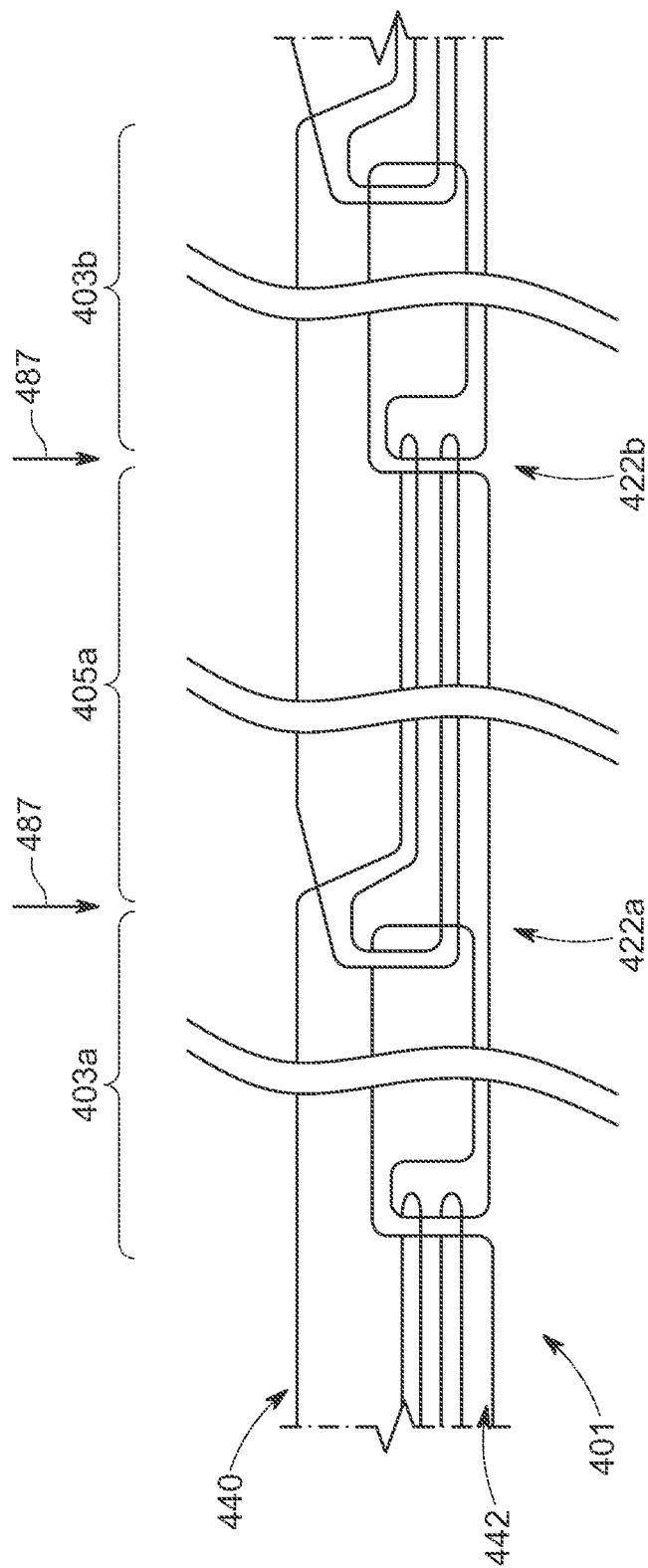

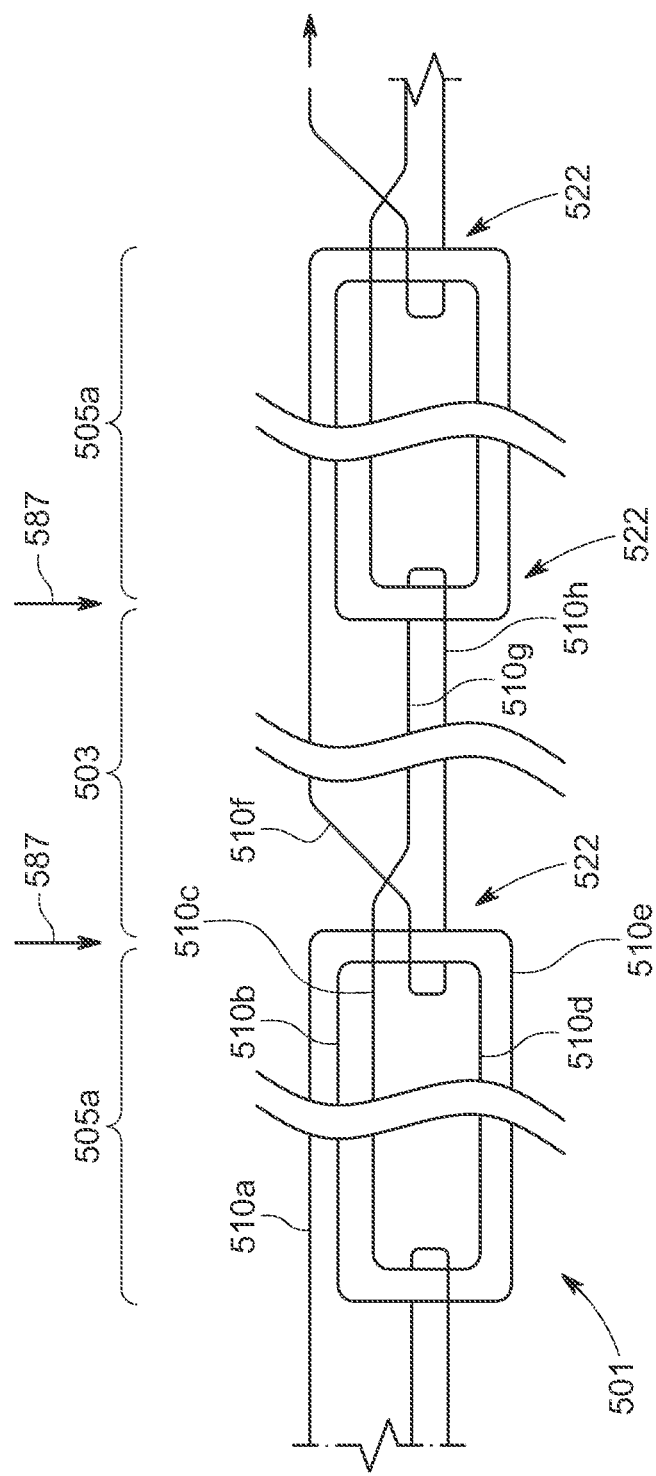

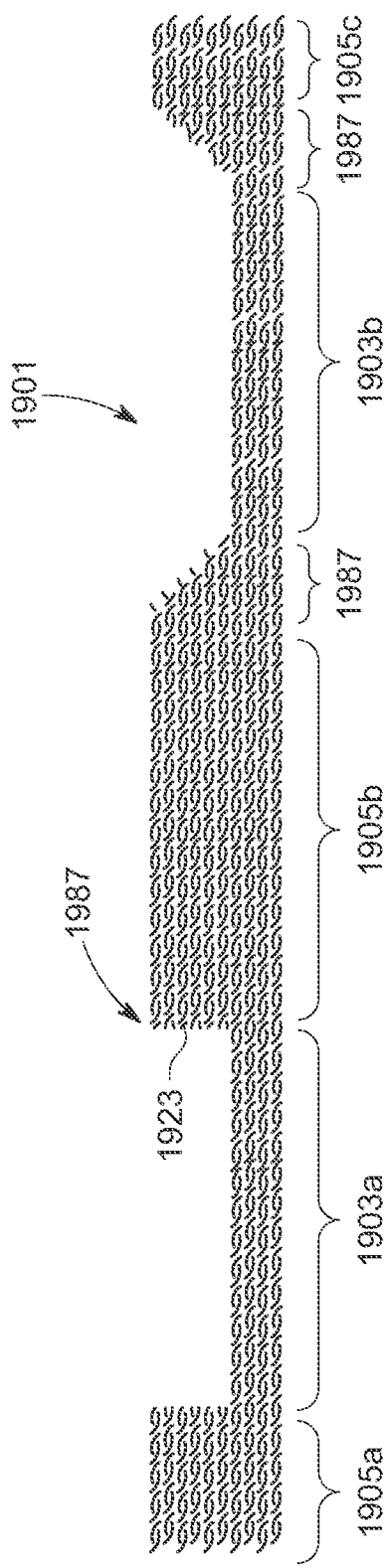
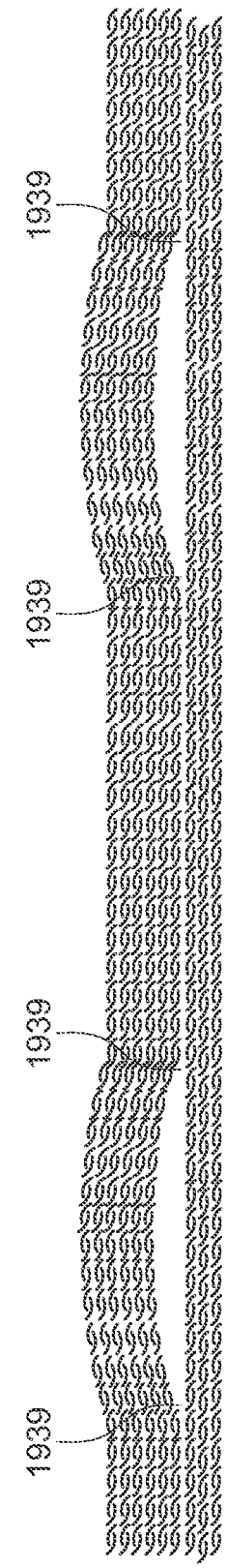
FIG. 9A
FIG. 9B

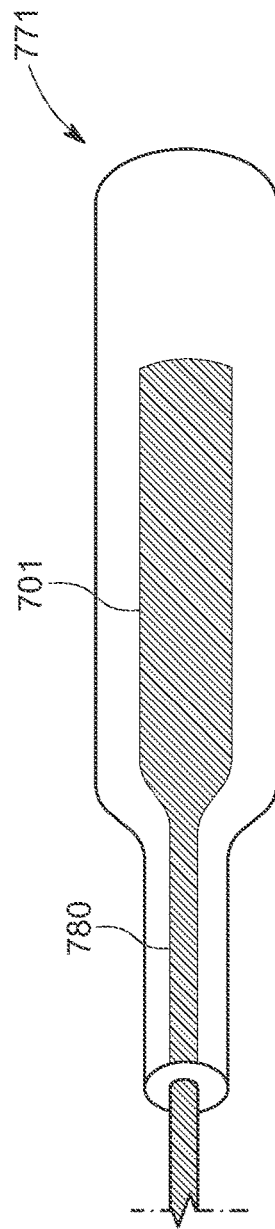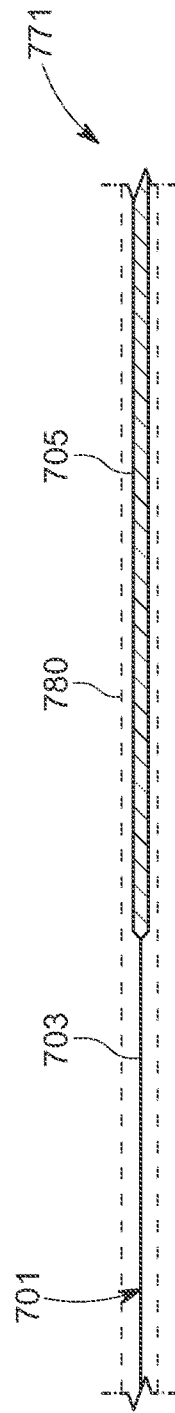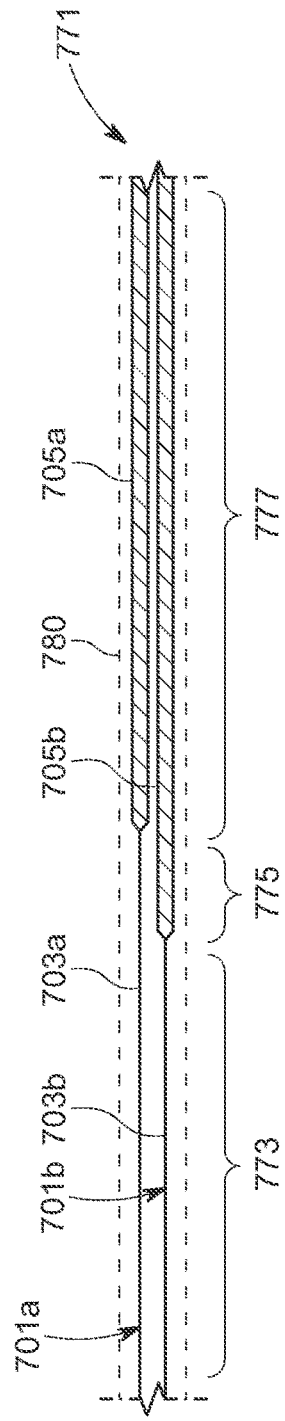
FIG. 12A
FIG. 12B
FIG. 12C

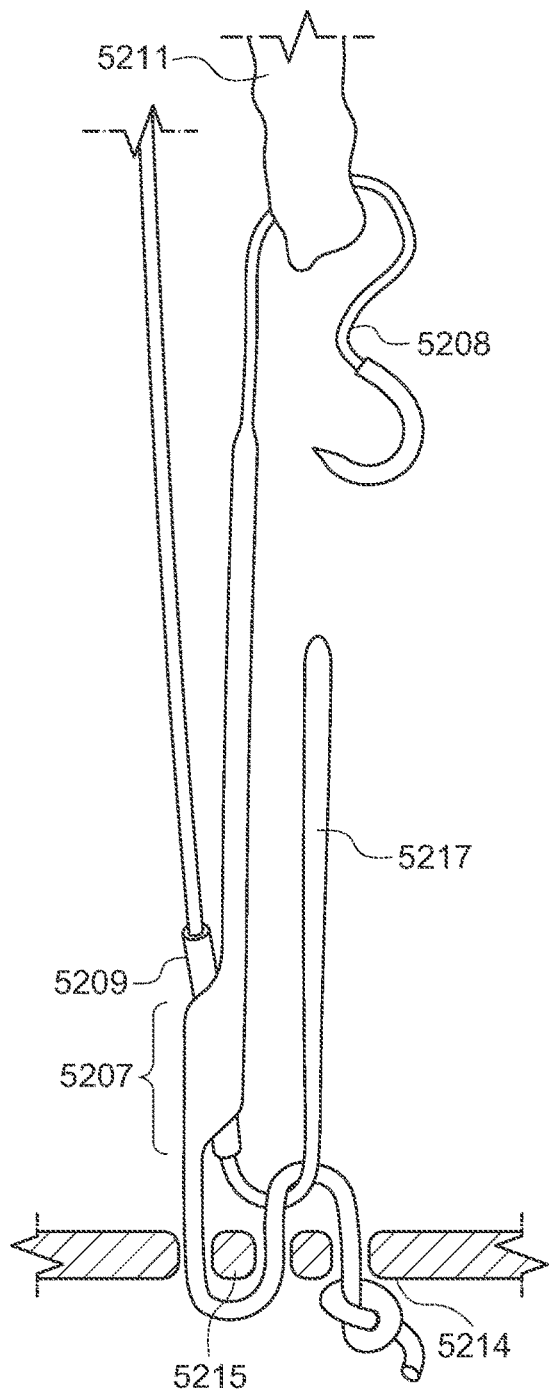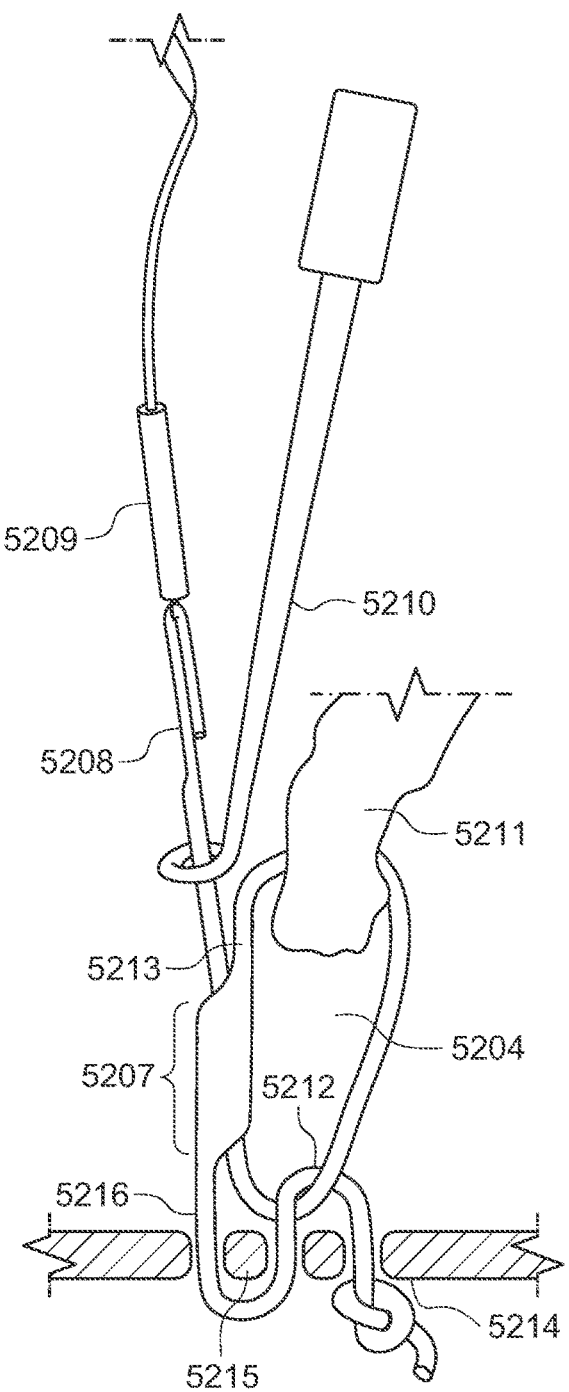
FIG. 22E
FIG. 22F

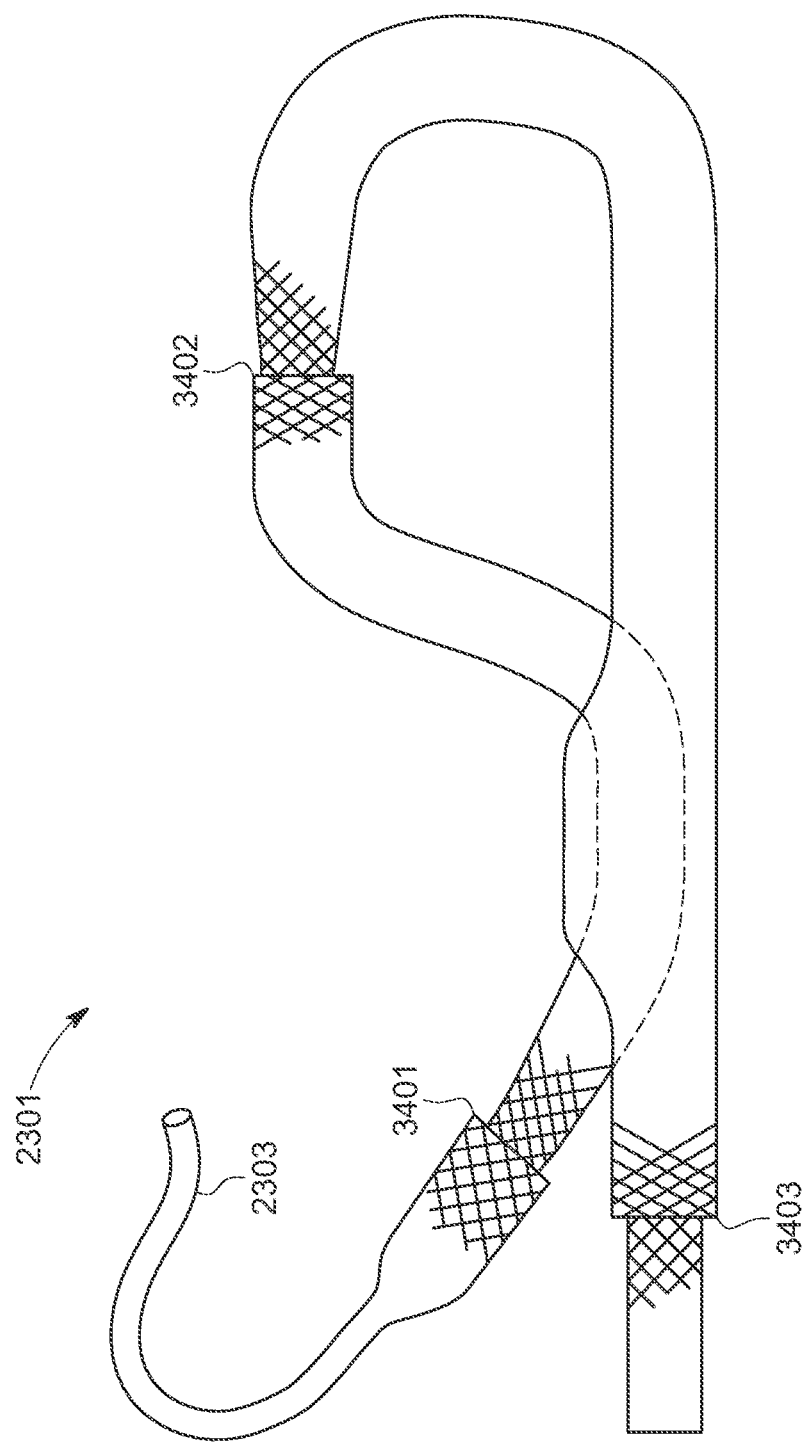

VARIABLE DENIER YARN AND SUTURE

CROSS REFERENCES TO RELATED APPLICATIONS

This application is a continuation of U.S. patent application Ser. No. 17/473,868 filed on Sep. 13, 2021, which is a continuation of U.S. patent application Ser. No. 14/537,719, filed on Nov. 10, 2014, titled "VARIABLE DENIER YARN AND SUTURE," now U.S. Pat. No. 11,116,498, which is a continuation-in-part of U.S. patent application Ser. No. 13/354,204, filed on Jan. 19, 2012, titled "VARIABLE DENIER YARN AND SUTURE," now U.S. Pat. No. 8,881,635, which claims priority to U.S. Provisional Application No. 61/542,990, filed on Oct. 4, 2011, titled "VARIABLE DENIER SURGICAL SUTURE AND BRAIDED ARBORIZED VASCULAR GRAFT;" U.S. Provisional Patent Application No. 61/453,453, filed on Mar. 16, 2011, titled "VARIABLE DENIER YARN AND SUTURE;" and U.S. Provisional Patent Application No. 61/438,880, filed on Feb. 2, 2011, titled "VARIABLE DENIER YARN AND SUTURE," each of which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates generally to variable denier yarn. In particular, this application relates to variable denier yarn that can be used to create a variable denier suture.

BACKGROUND

In many surgical procedures, particularly minimally invasive surgical procedures such as endoscopic suturing of internal body tissue, suturing must be accomplished using a suture that can fit through a surgical instrument or implant, such as a suture lock, having a very small opening. If the opening has a circular cross-section, for example, threading a suture having the same diameter as the opening can be nearly impossible. Moreover, many surgical procedures require looping the suture and pulling a doubled suture through the opening. As a result, most sutures have a smaller denier so as to easily fit through the intended opening and/or so as to be able to be folded over for proper threading by drawing a loop of suture through the opening.

However, in many cases, a suture having the largest diameter possible for the intended opening is advantageous both because a large diameter suture will provide increased stability of the suture in tissue, a larger suture is stronger, and because space in the surgical device will not be wasted with a partially unfilled opening. Moreover, in certain cases, in order to properly pinch or otherwise restrain the suture to avoid movement of the suture after completion of the surgical process, the suture ideally fills a majority of the opening of the surgical instrument or implant.

Currently, a variety of suture locks, or suture restraints, are available, including static compression locks and force multiplier locks. With static compression locks, a static force is applied to the suture with a crimp, screw mechanism, or a mechanism that pops together, and compression resulting from the dimension of the suture and residual space in the assembled mechanism locks the suture in place. In this case, the resistance to slip is defined by static forces and frictional coefficients. Force multiplier locks, on the other hand, couple tension applied to the suture with the pinching or locking force that is applied to the suture. Examples include wedge locks, cam locks, and locks that work on the principle of the Chinese finger trap. Force multiplier locks are usually slideable or tensionable because minimal force is applied to the suture as it is slid in the non-functional-load direction.

Backlash and loosening are often problems with traditional suture locks. While the static locks often have little backlash and resulting loosening from cyclic small movements, the dynamic locks have backlash problems associated with the cross-sectional area of the lock passage that must be closed with longitudinal suture movement in order to achieve locking. That is, initiation of locking with dynamic locks can require contact and friction and movement between the locking mechanism and the suture to initiate and complete locking. If the geometry of the passageway and suture dimensions are such that reliable contact between suture and lock is not present, an elastic biasing mechanism may be needed to move the lock against the suture in order to initiate the locking action.

The size of the passageway through suture locks usually must be large enough to accommodate a traction loop as well as a doubled thickness of suture. This is more than twice the passage cross-section necessary for the lock to function once the suture is drawn though the lock. This increased cross-section increases the size of the lock and makes it so that the lock mechanism must close down a large passage cross-section before locking can occur. In the case of the Chinese finger trap type locks, the reduction in cross section reduces the braid angle at locking, reducing the locking force multiplication factor from tension, increasing the required length of the lock, and generally reducing the efficiency of the lock.

Accordingly, there is a need for a suture having a larger denier at the central portion and a smaller denier near at least one end, particularly for use in a suture lock so as to improve locking.

SUMMARY OF THE DISCLOSURE

In general, in one embodiment, a textile yarn includes a first segment and a second segment. The first segment includes a plurality of first strands and has a substantially constant first denier. The second segment includes a plurality of second strands integrated together and has a substantially constant second denier. There are more second strands in the second segment than first strands in the first segment such that the second denier is greater than the first denier. A first portion of the plurality of second strands is made from a first plurality of yarn elements that extend through the first segment and the second segment. A second portion of the plurality of second strands is made from a second plurality of yarn elements that are present in the second segment and not the first segment. The yarn elements in the second plurality of yarn elements terminate in a transition zone between the first segment and the second segment.

This and other embodiments can include one or more of the following features. The plurality of second strands can be braided together. The plurality of first strands can be braided together. The plurality of first strands can be braided together in a tubular braid, and the plurality of second strands can be braided together in a tubular braid. The plurality of first strands can be braided together in a flat braid, and the plurality of second strands can be braided together in a tubular braid. The plurality of first strands can be braided together in a flat braid, and the plurality of second strands can be braided together in a flat braid. The plurality of second strands can be integrated as a warp knit. The plurality of first strands can extend in parallel along the length of the first segment. All of the plurality of first strands can be made from the yarn elements extending through the first segment and the second segment. Ends of the strands in the second plurality of yarn elements can be loose in the transition zone. The second denier can be at least twice as large as the first denier. The textile yarn can be a suture. There can be a tubular over-braid running the length of the textile yarn. There can be a plurality of first segments and a plurality of second segments, and the first and second segments can be arranged in an alternating pattern along the length of the textile yarn. There can be a third segment, and there can be more third strands in the third segment than second strands in the second segment such that the third denier is greater than the second denier. A first portion of the plurality of third strands can be made from the same yarn elements as at least some of the plurality of first strands and at least some of the plurality of second strands. The first portion of the plurality of third strands can extend through the first, second, and third segments.

In general, in one embodiment, a textile yarn includes a first segment, a second segment, and a transition zone between the first segment and the second segment. The first segment includes a plurality of first strands coextending axially and has a substantially constant first denier. The second segment has a plurality of second strands coextending axially and has a substantially constant second denier. The second segment has a greater number of strands than the first segment such that the second denier is greater than the first denier. The transition zone includes a first loop formed by two first strands connected to a plurality of second loops, and each second loop is formed by two second strands, such that the transition zone has an increasing denier from the first segment to the second segment. The aspect ratio of the length of each segment and the width of a first strand or a second strand is greater than 100.

This and other embodiments can include one or more of the following features. The first loop can be directly connected to the plurality of second loops. The transition zone can further include a plurality of third loops connecting the first loop and the plurality of second loops. There can be a plurality of first segments or second segments and a plurality of transition zones, and the distance between each transition zone can be between 5 and 100 cm. The second segment can have a greater number of wales per course than the first segment. The second denier can be at least twice as large as the first denier. There can be a tubular over-braid running the length of the textile yarn. The textile yarn can be a suture.

In general, in one embodiment, a method of suturing includes threading a first segment through an opening of a surgical instrument and pulling the suture through tissue to place a second segment of the suture against soft tissue. The first segment includes a plurality of first strands and has a substantially constant first denier. The second segment includes a plurality of second strands integrated together and has a substantially constant second denier. There are more second strands in the second segment than first strands in the first segment such that the second denier is greater than the first denier. A first portion of the plurality of second strands is made from a first plurality of yarn elements that extend through the first segment and the second segment. A second portion of the plurality of second strands is made from a second plurality of yarn elements that are present in the second segment and not the first segment. The yarn elements in the second plurality of yarn elements terminate in a transition zone between the first segment and the second segment.

This and other embodiments can include one or more of the following features. The method can further include wrapping the first segment around a traction loop before threading the suture. The method can further include cutting the first segment of the suture after the suture is pulled through. The denier of the second segment can be at least twice the denier of the first segment.

In general, in one embodiment, a method of suturing including threading a first segment of a suture through an opening of a surgical instrument and pulling the suture through tissue to place a second segment of the suture against soft tissue. The first segment includes a plurality of first strands coextending axially and having a substantially constant first denier. The second segment has a substantially constant second denier and has a greater number of strands than the first segment such that the second denier is greater than the first denier. The suture further includes a transition zone between the first segment and the second segment. The transition zone includes a first loop formed by two first strands connected to a plurality of second loops, and each second loop is formed by two second strands, such that the transition zone has an increasing denier from the first segment to the second segment. The aspect ratio of the length of each segment and the width of a first strand or a second strand is greater than 100.

This and other embodiments can include one or more of the following features. The method can further include wrapping the first segment around a traction loop before threading the suture. The method can further including cutting the first segment of the suture after the suture is pulled through. The denier of the second segment can be at least twice the denier of the first segment.

In general, in one aspect, a method of manufacturing an integrated suture includes creating a first segment of a yarn, creating a second segment of a yarn, and wrapping a cover over the first and second segments to create a suture. The second segment has a different denier than the first segment, and the first segment and the second segment are created continuously from at least some of the same yarn elements.

In general, in one aspect, a suture includes a polymer monofilament, the polymer monofilament having an end portion and a central portion, the end portion having a smaller denier than the central portion.

In general, in one aspect, a method of manufacturing a suture includes milling an end portion of a polymer monofilament such that the end portion has a smaller denier than a central portion of the monofilament.

In general, in one embodiment, a method of suturing includes: (1) wrapping a first segment of a suture through a traction loop; (2) pulling the traction loop and the first segment through an opening in a suture lock; (3) continuing to pull the traction loop such that a second segment of the suture extends through the opening, wherein the second segment has a greater denier than the first segment such that the second segment more nearly fills an entire dimension of the opening than the first segment; and (4) locking the suture in place with the second segment in the opening.

This and other embodiments can include one or more of the following features. The second segment can substantially fill the entire dimension of the opening when the suture is locked in place. The method can further include, prior to the wrapping step, threading the suture through a tissue such that a portion of the second segment sits against the tissue. The opening in the suture lock can be a channel within the suture. The channel can extend along a longitudinal axis that extends from a first end of the suture to a second end of the suture. The channel can be within the second segment. The first segment can form the first end of the suture, and pulling the traction loop can include pulling the loop along the longitudinal axis towards the second end of the suture. The first segment can form the first end of the suture, and pulling the traction loop can include pulling the loop along the longitudinal axis away from the second end of the suture. Ends of the channel can extend through a side-wall of the second segment. Wrapping the first segment through a traction loop can include folding the first segment over on itself. The denier of the second segment can be at least twice as large as the denier of the first segment. The method can further include cutting the first segment off of the suture after the locking step. The suture lock can include a cinching suture lock, a pinch-lock, a wedge lock, or a cam lock. The method can further include wrapping a third segment of the suture through a traction loop and pulling the traction loop and the third segment through an opening in the suture lock. The first and third segments can extend in opposite directions through the suture lock. The third segment can have a lower denier than the second segment.

In general, in one embodiment, a method of suturing includes: (1) threading a first end of a suture through tissue, wherein the suture includes a first segment and a second segment, wherein the second segment has a greater denier than the first segment, and wherein the first end includes the first segment and a portion of the second segment; (2) wrapping the first end of the suture through a traction loop that extends through a central channel of the suture after the threading step; and (3) pulling the traction loop such that the first end extends through the central channel to lock the suture in place.

This and other embodiments can include one or more of the following features. Pulling the traction loop such that the first end extends through the central channel to lock the suture in place can include pulling the first end until the portion of the second segment extends through the central channel. The central channel can be within the portion of the second segment. The denier of the second segment can be at least twice as large as the denier of the first segment. The method can further include cutting the first segment off of the suture after the pulling step. The central channel can extend down a longitudinal axis that extends from the first end of the suture to a second end of the suture. Pulling the traction loop can include pulling the loop along the longitudinal axis towards the second end of the suture. Pulling the traction loop can include pulling the loop along the longitudinal axis away from the second end of the suture. Ends of the channel can extend through a side-wall of the second segment. Wrapping the first end through a traction loop can include folding the first segment over on itself. The method can further include: (1) threading a second end of a suture through the tissue, the second end including a third segment; (2) wrapping the second end of the suture through a traction loop that extends through the central channel; and (3) pulling the traction loop such that the second end extends through the central channel to lock the suture in place. The first and second ends can extend through the central channel in opposite directions. The third segment can have a lower denier than the second segment.

In general, in one embodiment, a suture includes a first segment of suture including a plurality of first strands. The first segment has a substantially constant first denier. The suture also includes a second segment of comprising a plurality of second strands. The second segment has a substantially constant second denier. There are more second strands than first strands such that the second denier is greater than the first denier. All of the first and second strands are part of a continuous braid.

This and other embodiments can include one or more of the following features. A portion of the second strands can be cut in a transition zone between the first and second segments. Ends of the second strands can be positioned along an axis that is oriented substantially transverse to a longitudinal axis of the suture. The suture can further include an overbraid extending over the first and second segments. The first segment can be a tubular braid, and the second segment can be a tubular braid. The first segment can be a flat braid, and the second segment can be a tubular braid. The denier of the second segment can be at least twice the denier of the first segment. The strands of the second segment can consist of greater than one suture material. The aspect ratio of the second segment relative to the first segment can be greater than 100. The length of the second segment can be equal to or greater than one-third the length of the suture.

In general, in one embodiment, a suture device includes a suture having a first segment and a second segment. The first segment forms one end of the suture, and the second segment has a greater denier than the first segment. A traction loop is threaded through a central portion of the second segment substantially parallel to a longitudinal axis of the suture such that the first segment can be wrapped through the traction loop and pulled into the central portion of the second segment to lock the suture in place.

This and other embodiments can include one or more of the following features. The denier of the second segment can be at least twice the denier of the first segment. The traction loop can further extend through a side-wall of the second segment. The first segment can be a tubular braid, and the second segment can be a tubular braid. The first segment can be a flat braid, and the second segment can be a tubular braid.

In general, in one embodiment, a textile for making variable denier surgical sutures includes a warp knitted structure having at least one pillar stitch extending the length of the structure. In higher denier areas, additional yarns are incorporated in a warp-knit fashion with the pillar stitch. The same additional yarns in lower denier areas can leave the warp knit pattern and become straight yarns.

This and other embodiments can include one or more of the following features. The additional yarns can become weft yarns, running between the loops of the pillar stitch but without forming loops with the pillar stitch. The additional yarns in low denier areas can be unengaged with the pillar stitch. At least some additional yarn can be cut away in the lower denier areas, thereby further decreasing the denier in the low denier areas. The additional yarns can leave the warp pillar stitch in a stepwise fashion. One yarn can leave the pillar stitch to become a weft yarn, and then after one or more additional picks, another warped yarn can leave the pillar stitch, and so forth. The textile can further include cut straight yarns in the low denier portion.

In general, in one embodiment, a variable denier textile structure is made by knitting, where denier increase is achieved by having one or more loops engage a greater number of loops.

This and other embodiments can include one or more of the following features. The variable denier textile structure can be a warp knitted structure. The warp yarns can be converted to weft yarns by weft insertion.

In general, in one embodiment, a warp knit textile structure for making variable denier surgical sutures includes warp yarns that leave the pillar stitch, spanning over following pillar stitch picks without looping, and then subsequently become engaged with the pillar stitch as a warp knit structure again.

In general, in one embodiment, a variable denier suture includes a first segment having a first denier and a second segment having a second denier that is greater than the first denier. A first yarn extends from a proximal end to a distal end of the suture. The first yarn has a series of first loops extending through the first and second segment, and a second yarn extends from the proximal end of the suture to the distal end of the suture. The second yarn has a series of second loops extending through the first second segment and not the first segment.

This and other embodiments can include one or more of the following features. The second loops in the second segment can be aligned with the first loops in the second segment. The second yarn can be intertwined with the first loops in the first segment.

In general, in one embodiment, a surgical suture has a change in denier along its length, where change in denier is achieved by having a yarn loop from the lower denier segment engage a greater number of yarn loops connecting to a higher denier segment.

In general, in one embodiment, a surgical suture has change in denier along its length, where change in denier is achieved by having a yarn loop of first denier yarn engage a loop of higher second denier yarn in the higher denier portion.

In general, in one embodiment, a surgical suture includes a longitudinal textile structure having portions of greater and lesser denier, such that having a change in denier results from yarn loops from a greater denier portion engage a lesser number of yarn loops from a lower denier portion, and the continuation of at least one yarn from the greater denier portion passes substantially parallel with the lesser denier portion without forming loops while passing along the length of the lesser denier portion.

In general, in one embodiment, a surgical suture includes a knitted structure, where increased denier is created by increasing the number of loops at a given location along the suture while moving in a direction of increasing denier.

In general, in one embodiment, a variable denier surgical suture include a yarn that forms a constant repeating pattern of looping along the length of the suture (pillar stitch) and a second yarn with loops engaging the loops of the first yarn. The second yarn forms loops only in the suture portion having greater denier.

In general, in one embodiment, a surgical suture includes a first single-denier element extending from a proximal end of the suture to a distal end of the suture and a second single-denier element parallel with the first single-denier element and shorter than the first single-denier element. The second single-denier element extends from the proximal end of the suture to a position proximal to the distal end of the suture, and the second single-denier element is secured to the first single-denier element by one or more stitches.

This and other embodiments can include one or more of the following features. The surgical suture can further include an outer cover around the first and second single-denier elements. The outer thread can be braided. The stitches can be formed by a sewn thread. The sewn thread can extend the length of the suture.

In general, in one embodiment, a surgical suture includes a first element and a second element running parallel to and of different length than the first element. Sewn stitches penetrate or go around the first and/or second elements to attach the first element to the second element.

This and other embodiments can include one or more of the following features. A zig-zag stitch can be the stitch that attaches the elements. The second element can be sewingly attached to the first element, and the first element can form stitches penetrating through or around the second element. The first element can be a structure that can be sewn, and in the locations where the first element is sewn to the second, the first element can be used as a sewing structure. One of the structures can be one or more sewing threads that can be sewingly attached to the shorter second textile element.

In general, in one embodiment, a variable denier suture includes a first segment of the suture consisting only of an outer braid. An adjacent segment consists of the outer braid over a core element. The next adjacent segment consists of only the core element.

This and other embodiments can include one or more of the following features. The yarn of the outer braid can be monofilament. The yarns of the outer braid can be fused together near the end of the outer braid overlying the suture. The passing cross section through the axial channel of the second or third portions can be less than two times the compressed cross section of the second or third portions. The denier of the outer braid can be less than 0.5× the denier of the core element. The compressed-cross-section of the outer braid can be less than 0.5× the compressed-cross-section of the suture. The core element can be a tubular braided structure. The core element can be a twisted yarn structure.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

FIGS. 1A and 1B show embodiments of a multi-denier yarn.

FIGS. 2A and 2B show embodiments of a multi-denier yarn having three segments.

FIGS. 3A and 3B show embodiments of a multi-denier yarn having a repeating pattern of segments.

FIGS. 4A and 4B show embodiments of a knitted multi-denier yarn.

FIGS. 5A and 5B show embodiments of a woven multi-denier yarn.

FIG. 9A shows an embodiment of a Raschel knitted and cut multi-denier yarn. FIG. 9B shows a process of making the multi-denier yarn of FIG. 9A.

FIGS. 12A-12C show a composite structure including a multi-denier yarn.

FIG. 13A is an axial cross-section of FIG. 13B.

FIGS. 24A-24B show self-locking of the suture of FIG. 23.

DETAILED DESCRIPTION

Figure 5B:
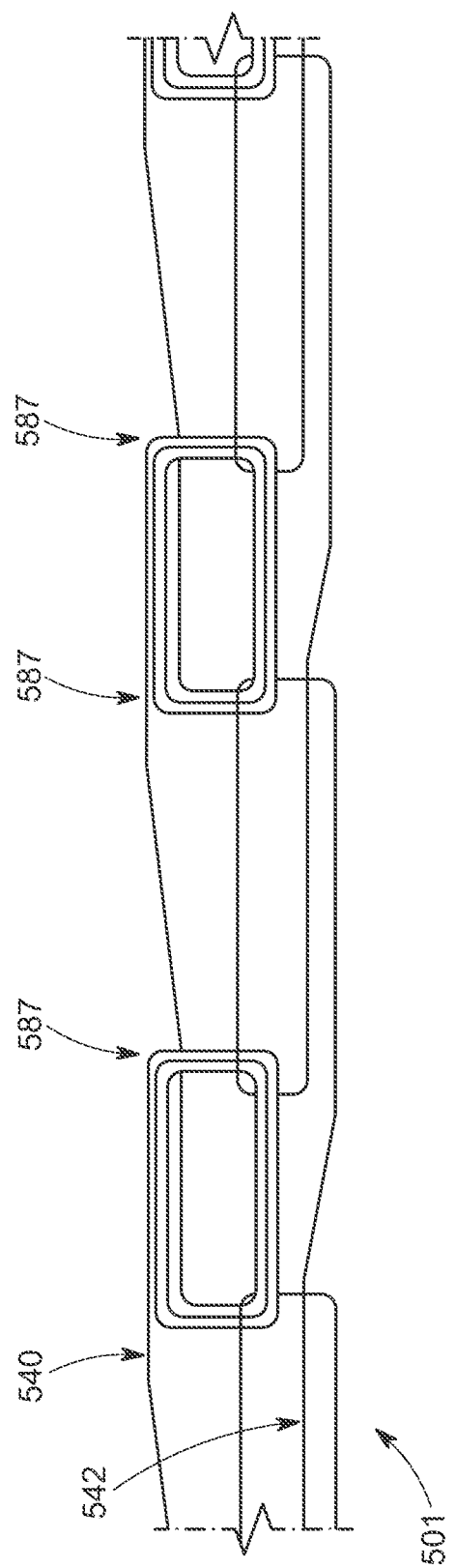

Described herein are yarns and sutures having variable deniers.

Referring to FIGS. 1A and 1B, a variable denier yarn 101 can include a low denier segment 103 and a high denier segment 105 having a higher denier than the low denier segment 103. Each segment 103, 105 can include multiple strands 110 coextending axially, i.e. extending substantially along the axis 120 of the variable denier yarn 101. As used herein, the number of strands is the number of yarn element cuts that would be made if a cut were made transversely through the yarn at a particular location. A transition zone 187 can be located at the intersection of, or between, the low denier segment 103 and the high denier segment 105 to transition from the higher denier to the lower denier. For the variable denier yarn 101 of FIGS. 1A and 1B, the transition zone 187 includes a node 122 formed by at least one loop 132 of segment 103 connected to at least one loop 132 of segment 105. Each loop can include a single yarn element, or continuous thread of yarn, looped back approximately 180°.

Referring to FIG. 1A, the denier of the high denier segment 105 can be greater than the denier of the low denier segment 103 because it has more strands 110 than the low denier segment 103. For example, the high denier segment 105 can have at least two times as many strands 110 as the low denier segment 103. Thus, as shown in FIG. 1A, segment 105 can have four strands 110c, 110d, 110e, 110f, while segment 103 can have only two strands 110a, 110b. The node 122 can include a loop 132a formed by strands 110a and 110b connected to a first loop 13b formed by strands 110c and 110f and a second loop 132c formed by strands 110e and 110g. Thus, there are more loops 132 associated with segment 105 than segment 103.

Referring to FIG. 1B, the denier of the high denier segment can be greater than the denier of the low denier segment 103 because the strands 110 of segment 105 can have a greater denier than the strands 110 of segment 103. Thus, there can be an equal number of strands 110 in segment 103 as in segment 105. In the simplest case, as shown in FIG. 1B, segment 103 can include two strands 110a, 110b, and segment 105 can include two strands 110c, 110d. In this embodiment, loop 132a connecting strands 110a and 110b can pass through loop 132b connecting strands 110c and 110d to form the node 122.

A variable denier yarn can include at least one change in denier along its length. Referring to FIGS. 2A and 2B, a multiple-denier yarn 201 includes a high denier segment 205 surrounded by low denier segments 203a, 203b on either side. Transition zones 287 are located at the intersections of the low denier segments 203a, 203b with the high denier segment 205. The transition zones 287 can include nodes 222a, 222b. Each segment can have the same number of loops 232 at node 222a as at node 222b. Although FIGS. 2A and 2B show only three segments with the central segment being the high denier segment, there may be more segments with more than two different deniers and/or there may be only three segments with the central segment being the low denier segment.

As shown in FIGS. 2A and 2B, the high denier segment 205 of variable denier yarn 201 can comprise more strands 210 than the low denier segment 203. Further, each segment 203a, 203b, 205 can include a yarn element that does not extend to adjacent segments. Thus, the variable denier yarn 201 can be manufactured in a way such that it includes yarn elements that do not extend the entire length of the yarn.

Referring to FIG. 2A, the strands 210c, 210e, 210d, 210f of segment 205 can all be formed of the same yarn element. Further, segments 203a, 203b can each include strands 210a, 210b and 210g, 210h formed of different yarn elements than segment 205. Therefore, in the embodiment of FIG. 2A, no yarn elements cross the transition zones 287. The strands 210c, 210e, 210d, 210f of segment 205 can be connected together at a point 230, for example with a knot.

Referring to FIG. 2B, variable denier yarn 201 can include a yarn element that crosses through one or more transition zones to form strands of different segments. For example, as shown in FIG. 2B, a single yarn element can form strands 210a, 210d-h, and 210i. However, segments 203*a*, 203*b* can still each include strands 210*b*, 210*c* and 210*j*, 210*k*, respectively, formed of different yarn elements.

In some embodiments, the variable denier yarn includes a repeating pattern of segments. For example, referring to FIGS. 3A and 3B, the variable denier yarn 301 can include a pattern of alternating low denier segments 303 and high denier segments 305. Each segment can be separated by a transition zone 387. The transition zone 387 can include a node 322 connecting loops of adjacent segments. The high denier segments 305 can each include at least two loops at opposing nodes 322. There can be at least two low denier segments 303 and at least two high denier segments 305 arranged in an alternating pattern.

Referring to FIG. 3A, each segment can be formed of its own yarn element connected together at a point 330. In other embodiments, one or more yarn elements can continue throughout the entire variable denier yarn 301, i.e. through the transition zone 387, to create all of the segments. For example, as shown in FIG. 3B, two yarn elements 340 and 342 can form all of the strands of each segment.

Referring to FIGS. 4A and 4B, the variable denier yarn 401 can be knitted, i.e. fabricated from successive interlooping of yarn elements. Thus, each yarn element can extend the entire length of the multi-denier yarn 401.

Referring to FIG. 4A, a multi-denier yarn 401 can be formed from a single yarn element. Thus, as shown in FIG. 4A, the low denier segments 403 can include a lower number of strands 410 than the higher-denier segments 405. For example, the low denier segments 403 can include three strands 410 while the high denier segments can include seven strands 410. The low denier segments 403 and the high denier segment 405 can be separated by a transition zone 487*a, b, c*, which each includes a nodes 422. Further, the high denier segments 405 can include at least two loops at opposing nodes 422 as well as at least one strand that passes through each transition zone 487*a, b, c*. For example, segment 405*a* includes three loops 432*a*, 432*b*, 432*c* at node 422*a* and three loops 432*d*, 432*e*, 432*f* formed at node 422*b*. Further, strand 410*a* crosses through the transition zone 487*a* to form strand 410*f*. Likewise, strand 410*d* crosses the transition zone 487*b* to form strand 410*i*. Although only two low denier segments 403 and two high denier segments 405 are shown in FIG. 4A, there can be different number of segments, which can be in a repeating pattern.

Referring to FIG. 4B, a multi-denier yarn 401 can be formed from multiple yarn elements. For example, as shown in FIG. 4B, two yarn elements 440 and 442 can each extend along the length of the multi-denier yarn 401.

Referring to FIGS. 5A and 5B, the variable denier yarn 501 can be woven, i.e. fabricated by passing a bobbin around a yarn element rather than by pulling a loop around a yarn element. Thus, during weaving, the bobbin carries the end of the yarn element, whereas during knitting and crocheting, the loop around a yarn element does not include the end of the yarn element. Again, each yarn element can extend the entire length of the multi-denier yarn 501.

Referring to FIG. 5A, the multi-denier yarn 501 can be formed from a single yarn element. A yarn element can include a group of subelements running parallel but not integrated together as a textile. The higher-denier segments 505 can have more strands than the low denier segments 503. For example, the low denier segments 503 can include three strands 510 while the high denier segments can include five strands 510. The transition zone 587 can include a node formed by at least one loop of segment 503 connected to at least one loop of segment 505. Further, the high denier segments 505 can include at least two loops at opposing nodes 522 as well as at least one strand that passes across each node 522. Although only two high denier segments 505 and one low denier segment 503 are shown in FIG. 5A, there can be a different number of segments, which can be in a repeating pattern.

Referring to FIG. 5B, the multi-denier woven yarn 501 can be formed from multiple yarn elements. For example, as shown in FIG. 5B, two yarn elements 540 and 542 can each extend along the length of the multi-denier yarn 501.

The yarns including two or more yarn elements with alternating engagement, such as those described with reference to FIGS. 3B, 4B, and 5B, can advantageously avoid creating differential lengths of strands within a segment, which can create slack strands in the yarn. This is because in these cases, at a transition zone, the loops of one yarn element engage adjacent opposing loops of a different yarn element. Further, tension on a given yarn element remains constant as the yarn element passes across a transition zone. In two different denier segments, the sum strand tension is equal, for both the single yarn element yarn, and for the multiple yarn element yarn. Yet, for any strand that crosses the transition zone, the tension is the same throughout the strand spanning both segments. The strand tension is constant for each strand that crosses a transition zone, regardless of which segment it is in. Therefore, for the cases in FIGS. 3B, 4B, and 5B there must be equal tensions on the two opposing arms of all loops. Thus there is no pulley effect where opposing loops cross one another, and no tendency to develop slack strands that cause tangling in the course of manufacture. Moreover, the two yarn element embodiment allows the strands to run parallel to one another along the length of the segment, rather than crossing over one another along the length of the segment. The same principles can be extended to a yarn with greater than two yarn elements. In contrast, for a single-yarn-element yarn such as in FIG. 4A, the loops that interface at transition zones have different tensions on the opposing arms of a given loop, because the strand count, with the same yarn element, is different in the different segments. The mean strand tension is different in the different segments, but the strand tension in the strand crossing the transition zone is equal. If the coefficient of friction were nearly zero, there would be pulley slippage where the opposing loops engage each other.

Figure 6:
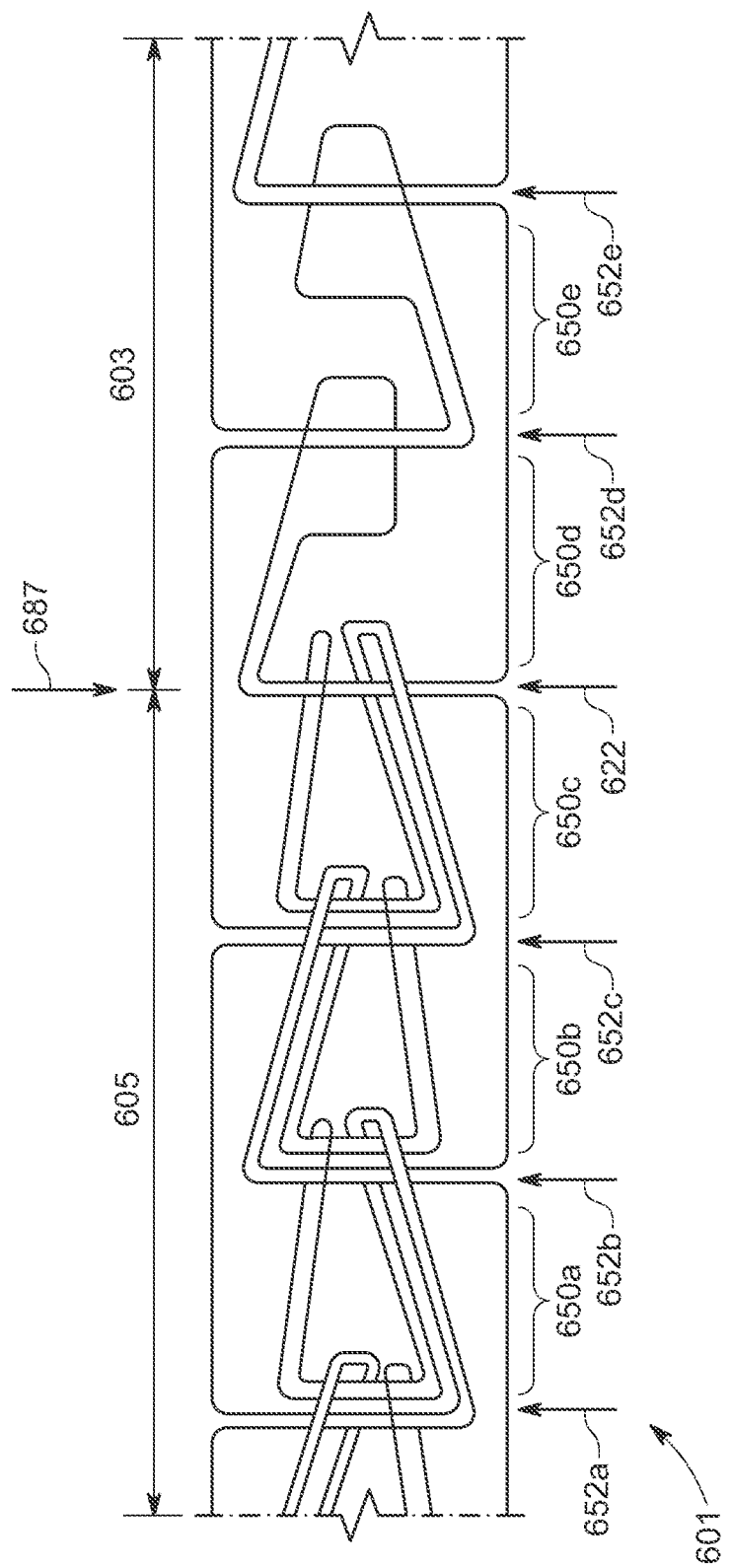
FIG. 6 shows an embodiment of a multi-denier yarn with segments having a plurality of sections.

In some embodiments, one or more segments in a multi-denier yarn can have multiple sections connected by semi-nodes, i.e. loop connections between strands of the same segment such that there is no change in denier. For example, referring to FIG. 6, a multi-denier yarn 601 includes a low denier segment 603 and a high denier segment 605 connected by a transition zone 687 having a node 622. The high denier segment 605 includes a plurality of sections 650 connected by semi-nodes 652. Each section 650*a*, 650*b*, 650*c* of the high denier segment 605 is of equal denier, and each section 650*d*, 650*e* of the low denier segment 603 is of equal denier. There can be one, two, or more sections 650 in at least one segment of the multi-denier yarn 601. For example, each segment can include two or three sections. Although the multi-denier yarn 601 shown in FIG. 6 is knit, the yarn 601 can also be woven. A knit multi-denier yarn 601, as shown in FIG. 6, may be advantageous to achieve close semi-node spacing.

Figure 7A:
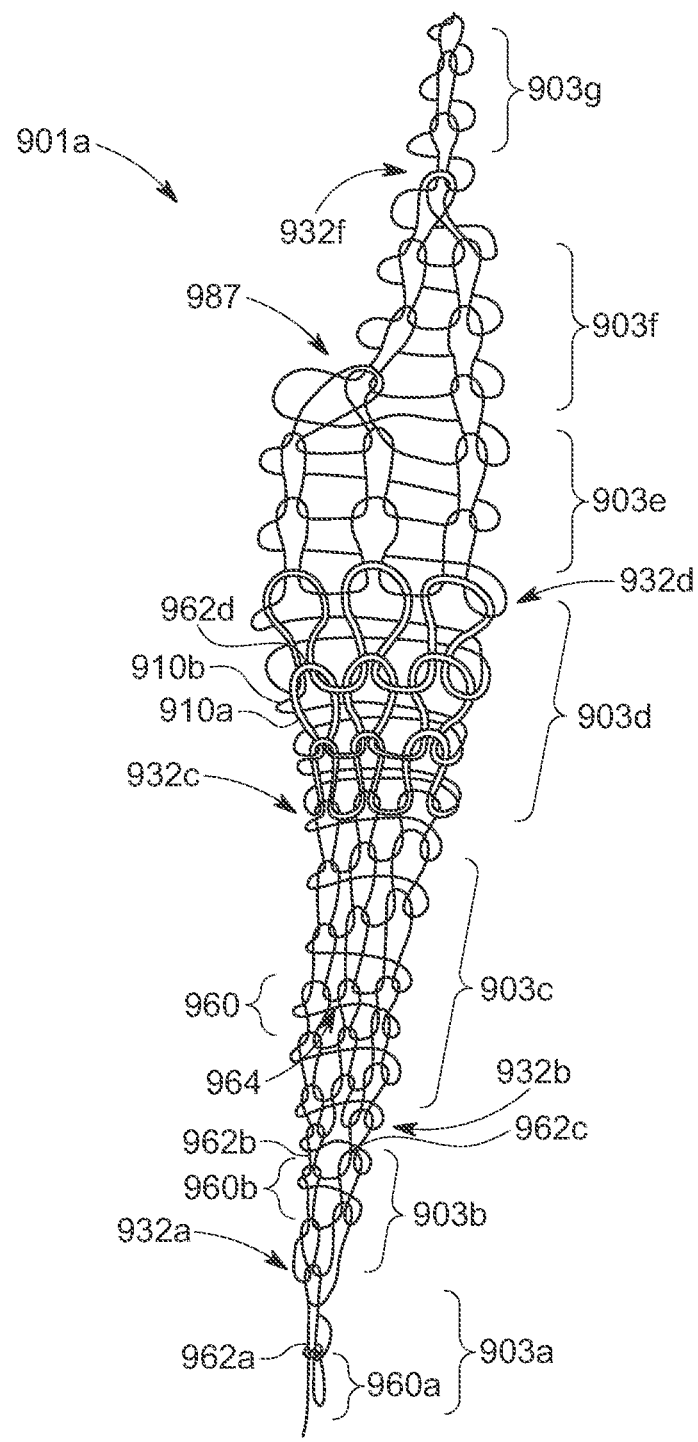
FIGS. 7A and 7B show embodiments of a linear knitted yarn.
Figure 7B:
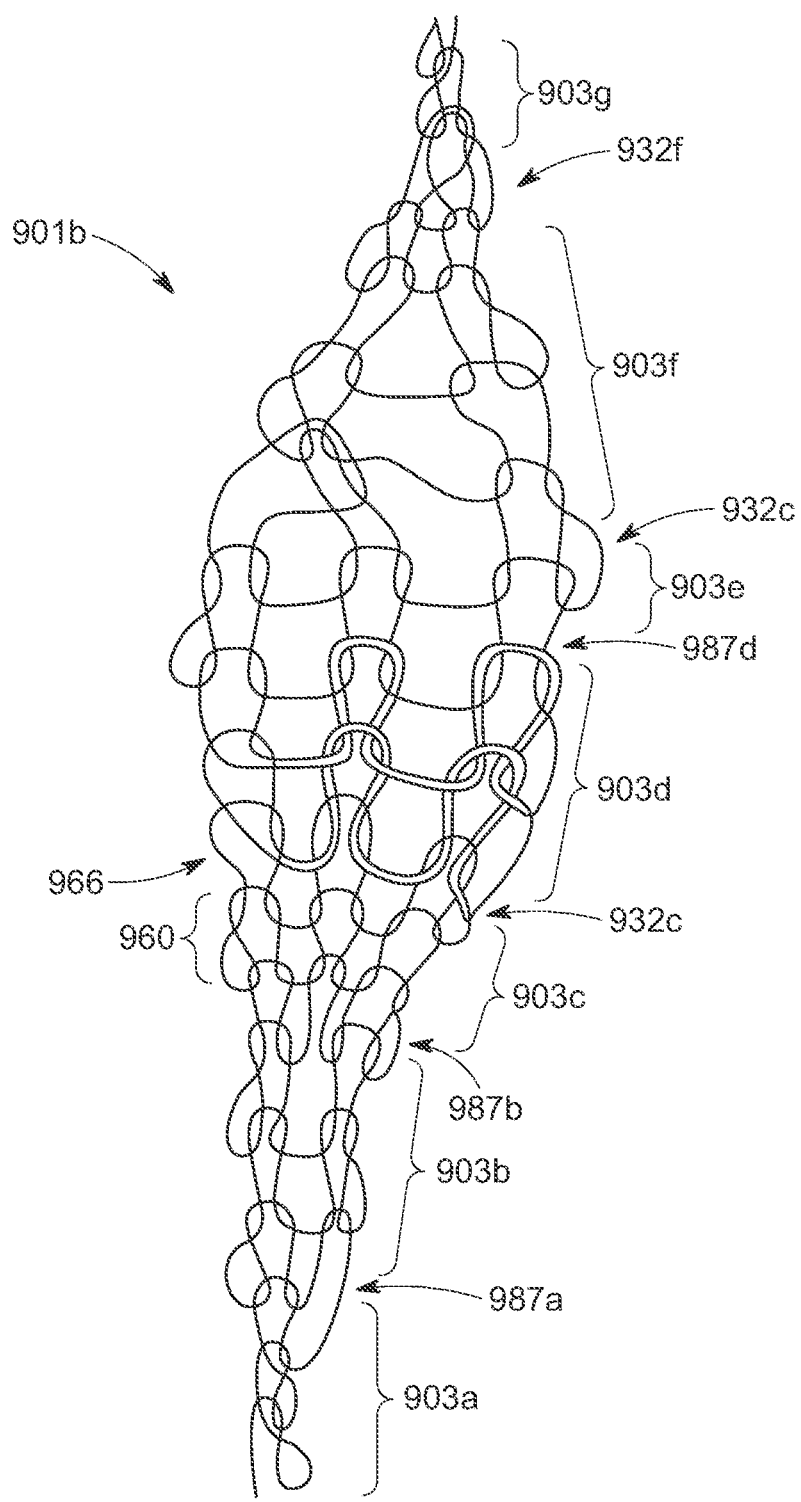

In some embodiments, shown in FIGS. 7A and 7B, a multi-denier yarn can be constructed as an elongate or linear weft knitted structure. Referring to FIG. 7A, a multi-denier yarn 901*a* can be formed as a linear knitted structure with the progression of yarn extending back to start on the same side on every course or radial row of stitches, advancing to the new row or course. Thus, the yarn 901a can be formed of a plurality of circumferentially-extending courses 960, each course including at least one wale 962 or back-and-forth loop. Each course 960 can include a circumferential strand 964 extending either in front or in back of the course to start the next course, substantially forming a circular knit.

The multi-denier yarn 901a can include at least two segments 903 of different denier connected by nodes 932. The change in denier from one segment 903 to another segment at transition zone 987 can be the result of an increase in the number of strands 910 per segment.

The increase in the number of strands 910 per segment 903 can be caused by an increase in the number of wales 962 per course 960. For example, course 960a of segment 903a includes a single wale 962a, while course 960b of segment 903b includes two wales 962b, 962c. Likewise, each course of segment 903c includes more wales than each course of segment 903b. Alternatively, or in addition, the number of strands 910 per segment 903 can be caused by an increase in the number of strands 910 per wale. For example, segment 903d includes two strands 910a, 910b in a single wale 962d. In one embodiment, the yarn 901 can be made by controlling the raising of the latch needles of a circular knitting machine, e.g., by holding them raised for one or more extra revolutions, then proceeding with the cam one revolution to make the stitches, and again holding them raised for one or more revolutions. The transition zones 987 between each segment can differ depending on the cause of the change in denier as well as the direction of knitting. For example, the increase in denier at node 932b is caused by the formation of an additional loop, the increase in denier at node 932c is caused by looping back over the same course, the decrease in denier at 932d is caused by decreasing the amount of looping back over the same course, and the decrease in denier at 932c and 932f is caused by using a transfer stitch. In each case, however, the change in denier can be associated with a single loop engaging multiple loops, or vice versa, or by a given number of loops engaging a greater or lesser number of loops. In some embodiments, a computerized flat-bed knitting machine, such as a Shima-Seiki, can be used to create transfer stitches to pass the loops of two wales to a single wale in an adjacent course.

Referring to FIG. 7B, a multi-denier yarn 901b can be formed as a flat linear knitted structure with stitches reversing direction along each row of stitches. Thus, the yarn 901b can be formed of a plurality of circumferentially-extending courses 960, each course including at least one wale 962. Each course 960 can include an axially extending strand 966 to start the next course.

Similar to the multi-denier yarn 901a of FIG. 7A, the multi-denier yarn 901b can include at least two segments 903 of different denier connected by transition zones 987. The change in denier from one segment 903 to another segment can be the result of an increase in the number of strands per segment 903, which can be the result of an increase in the number of wales per course or an increase in the number of strands per wale.

Figure 8A:
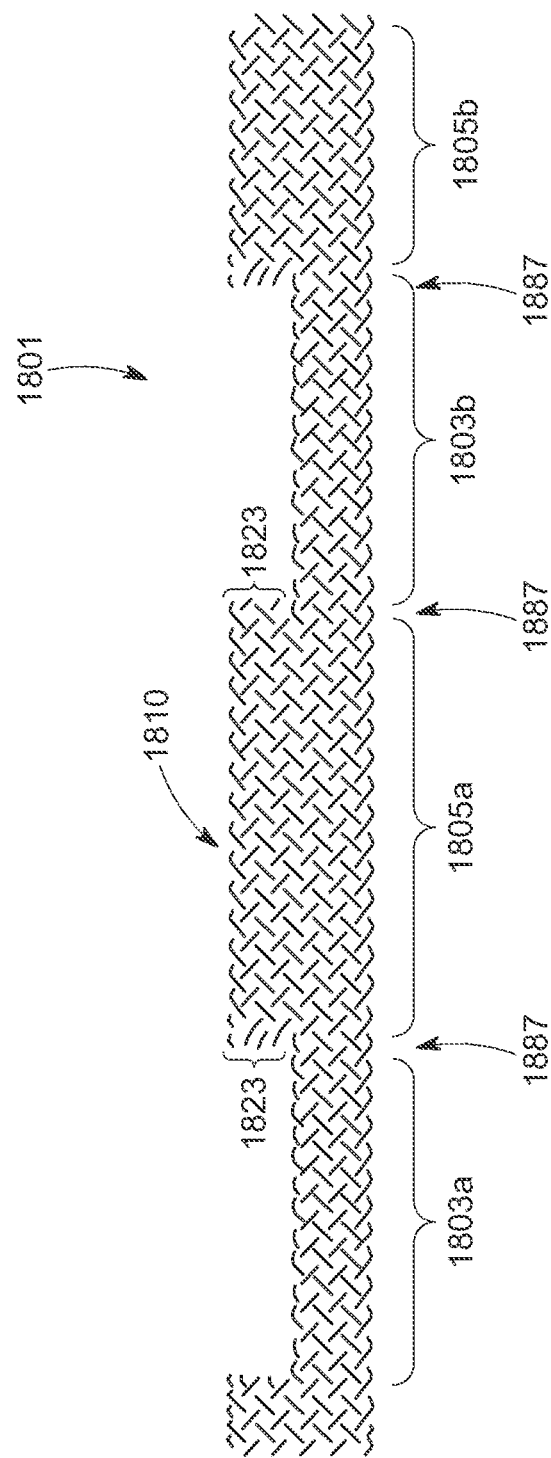
FIG. 8A shows an embodiment of a braided and cut multi-denier yarn.

Referring to FIG. 8A, in some embodiments, a multi-denier yarn 1801 can include segments 1803a,b and segments 1805a,b. Segments 1805a,b can have a greater number of strands than segments 1803a,b such that the segments 1805a,b have a higher denier than segments 1803a,b. The strands 1810 of each segment can be integrated together, such as braided together. Some yarn elements of the high denier segments 1805a,b can terminate at a transition zone 1887 between the high denier segments 1805a,b and the low denier segments 1803a,b. Thus, the transition zone 1887 can include ends 1823 of yarn elements of the higher denier sections 1805a,b that do not extend into the low denier segments 1803a,b. In some embodiments, the ends 1823 can be loose ends, i.e., not attached together. In other embodiments, the ends 1823 can be attached together, such as with a glue or by melting.

Figure 8B:
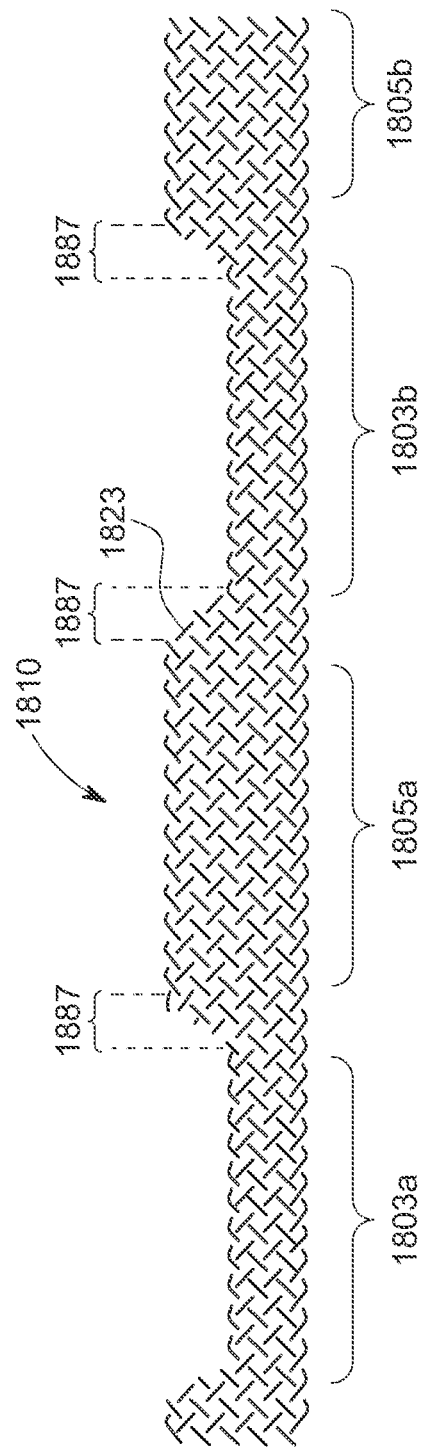
FIG. 8B shows an embodiment of a braided and cut multi-denier yarn having a gradual change in denier.

As shown in FIG. 8A, the ends 1823 can all be aligned transversely to the axis of the multi-denier yarn such that there is a sudden change in denier at the transition zone 1887. In another embodiment, the array of ends 1823 can be aligned oblique to the yarn axis so as to create a more gradual change in denier from the low denier segments 1803a,b to the high denier segments 1805a,b at the transition zone 1887, as shown in FIG. 8B. The yarn elements forming the strands of the low denier segments 1803a,b can extend into neighboring segments 1805a,b to form strands of the high denier segments 1805a,b.

In some embodiments, the strands in each segment are braided together in a tubular braid. In other embodiments, the strands of the high denier segments 1805a,b are braided together in a tubular braid while the strands of the low denier segments 1803a,b are braided together in a flat braid. In still other embodiments, the strands in each segment are braided together in a flat braid.

Figure 8C:
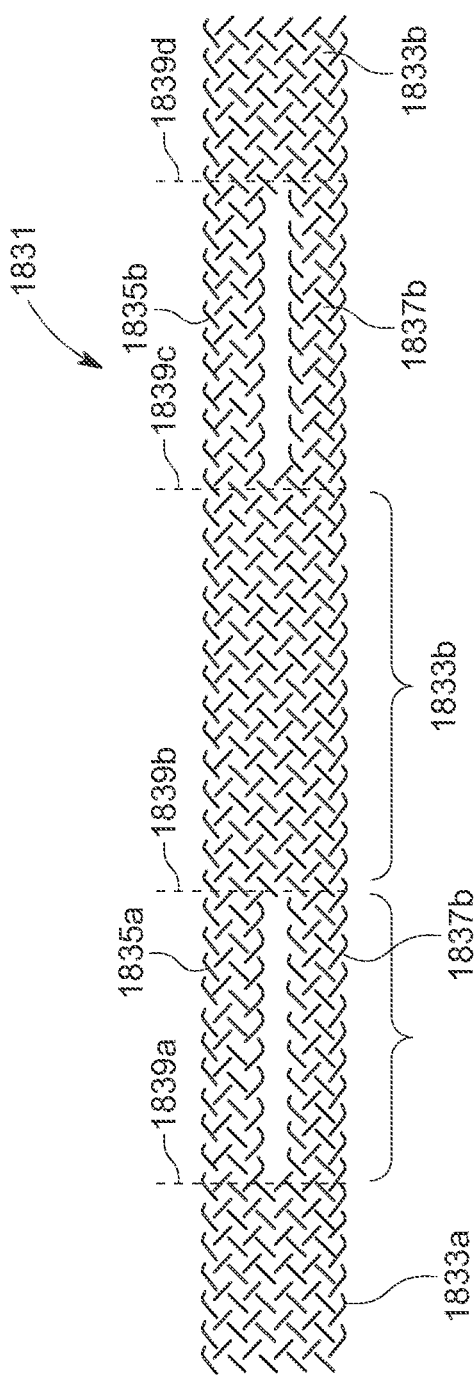
FIG. 8C shows a process of making the multi-denier yarn of FIG. 8B.

Referring to FIG. 8C, the multi-denier yarn 1801 of FIG. 8A can be formed from a yarn 1831 having a single braid section 1833 that divides into two or more parallel unitary braids 1835, 1837 and then joins back into a single unitary braid 1833 again. One or more of the parallel braids 1835, 1837 can then be cut at the splits 1839. The remaining parallel braid 1835, 1837 can form the lower-denier segment 1803 of the multi-denier yarn 1801, while the unitary braid 1833 can form the higher-denier segment 1805.

Referring to FIG. 9A, in some embodiments, a multi-denier yarn 1901 can include segments 1903a,b and segments 1905a,b,c. Segments 1905a,b can have a greater number of strands than segments 1903a,b such that the segments 1905a,b have a higher denier than segments 1803a,b. The strands 1910 of each segment can be knitted together in a warp knit, such as a raschel knit, crocheted together, or knitted together with parallel pillar stitches and weft inlays. Some yarn elements of the high denier segments 1905a,b can terminate at a transition zone 1987 between the high denier segments 1905a,b and the low denier segments 1903a,b. Thus, the transition zone 1987 can include ends 1923 of yarn elements of the higher denier sections 1905a, b that do not extend into the low denier segments 1903a,b. The yarn elements forming the strands of the low denier segments 1903a,b can extend into neighboring segments 1905a,b to form strands of the high denier segments 1905a,b as well.

Referring to FIG. 9B, the multi-denier yarn 1901 of FIG. 9A can be formed from a yarn 1931 having a full raschel knit section 1933 that is cut at splits 1939 to form high denier segments 1905 and low denier segments 1903.

Figure 10A:
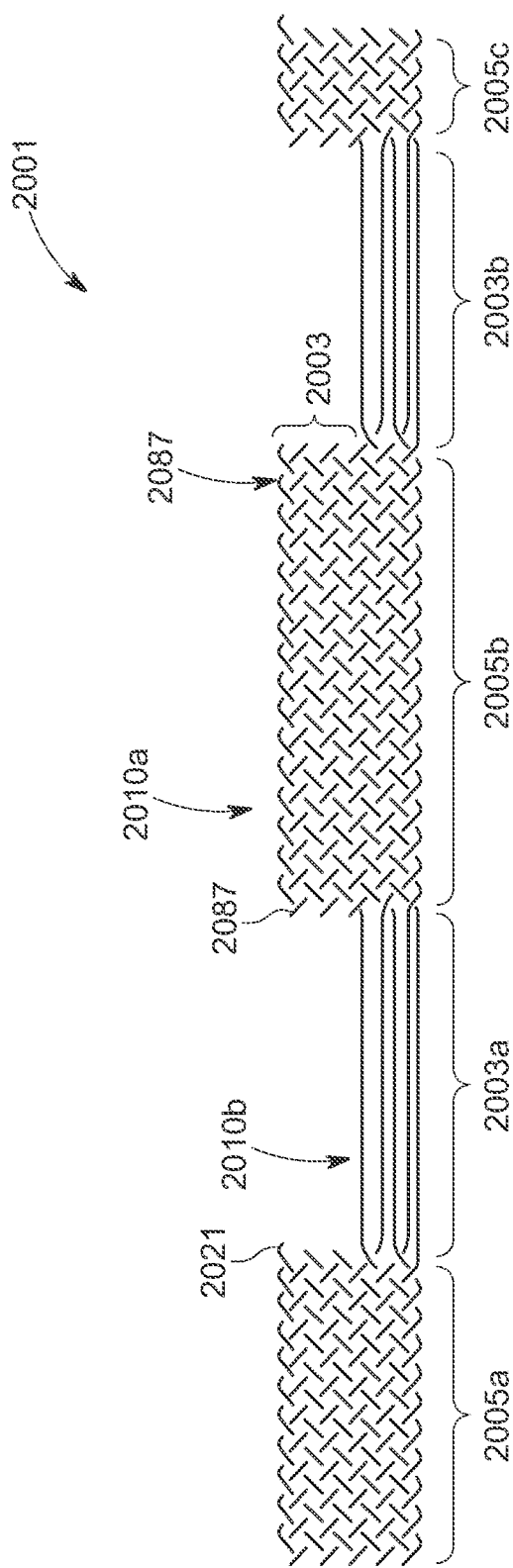
FIG. 10A shows an embodiment of a multi-denier yarn having braided and unbraided portions.
Figure 10B:
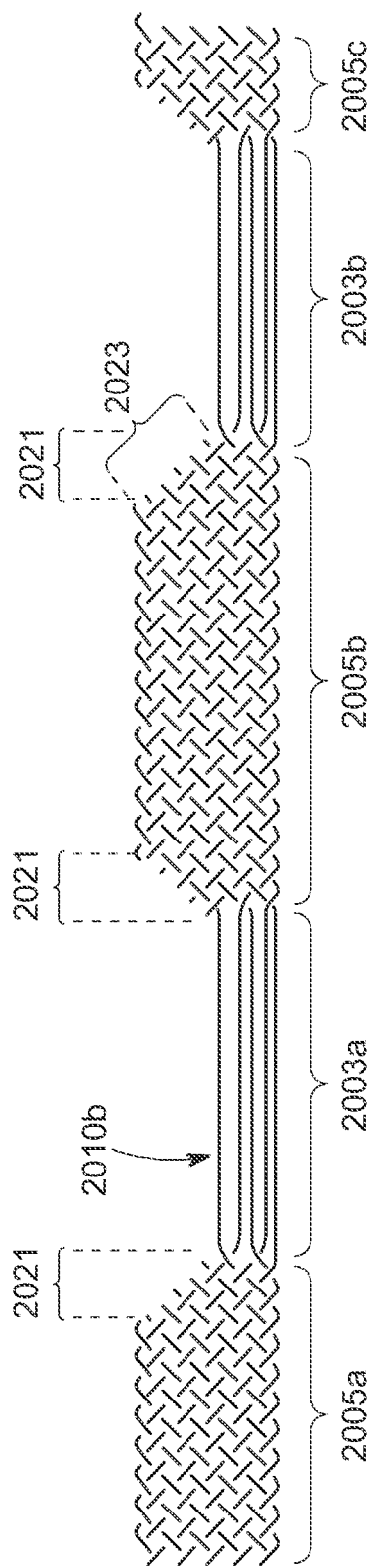
FIG. 10B shows an embodiment of a multi-denier yarn having braided and unbraided portions and having a gradual change in denier.

Referring to FIG. 10A, in some embodiments, a multi-denier yarn 2001 can include segments 2003a,b having a lower denier than segments 2005a,b. The higher-denier segments 2005a,b can include strands 2010a of yarn integrated together, such as in a tubular or flat braid, a tubular or flat braid with longitudinal warp fibers, a warp knit, or a weave with warp and weft yarn elements. In contrast, the lower-denier segments 2003a,b can include strands 2010b extending substantially parallel to one another and the axis of the yarn 2001, i.e. can be not braided, knit, or woven. Some yarn elements of the high denier segments 2005a,b can terminate at a transition zone 2087 between the high denier segments 2005a,b and the low denier segments 2003a,b. Thus, the transition zone 2087 can include ends 2023 of yarn elements of the higher denier sections 2005a,b that do not extend into the low denier segments 2003a,b. As shown in FIG. 10A, the ends 2023 can all be aligned transversely to the axis of the multi-denier yarn such that there is a sudden change in denier at the transition zone 2087. In another embodiment, the ends 2023 can be aligned diagonally so as to create a gradual change in denier from the low denier segments 2003a,b to the high denier segments 2005a,b, as shown in FIG. 10B. The yarn elements forming the strands of the low denier segments 2003a,b can extend into neighboring segments 2005a,b to form strands of the high denier segments 2005a,b.

Figure 10C:
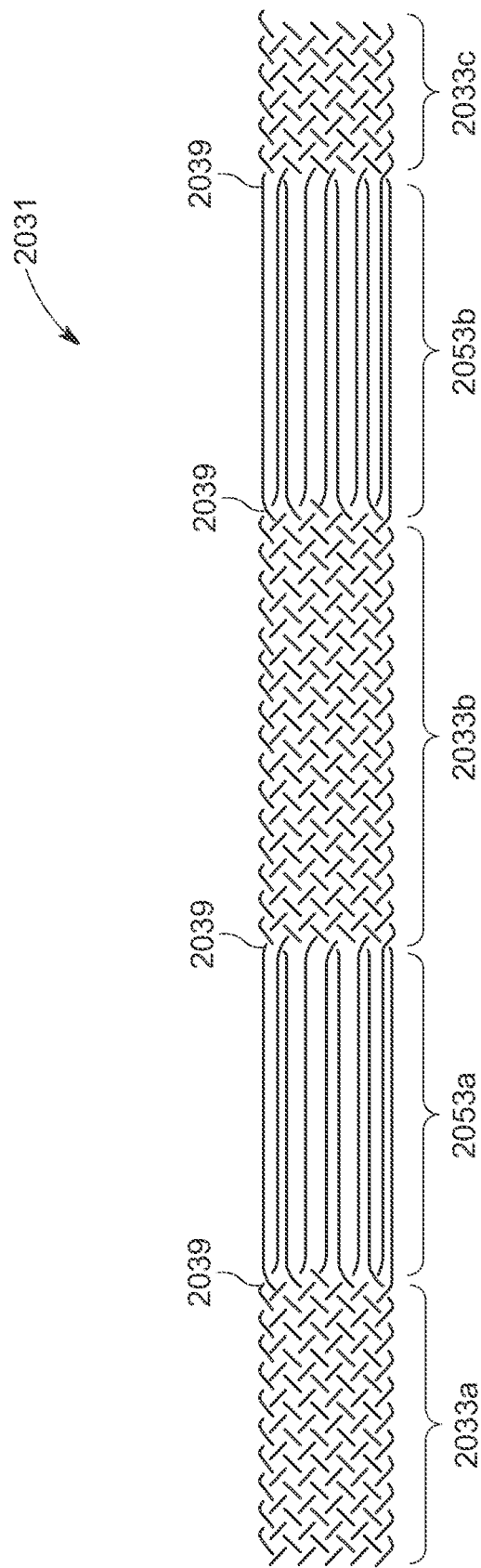
FIG. 10C shows a process of making the multi-denier yarn of FIG. 10A.

Referring to FIG. 10C, the multi-denier yarn 2001 of FIG. 10A can be formed from a yarn 2031 having a single braided section 2033, an unbraided section 2053, and then another braided section 2033. The yarn elements can be cut at the splits 2039 to form the lower-denier segments 2003 and the high denier segments 2005.

In some embodiments, a multi-denier yarn as described with respect to FIGS. 8 through 10 can include, in addition to yarn elements that are braided or knit, warp yarn elements running longitudinally that run through the braided or knit portions but are not themselves braided or knit. These warp yarn elements may be included throughout the yarn cross section or may be located in only portions of the yarn cross section.

Figure 11:
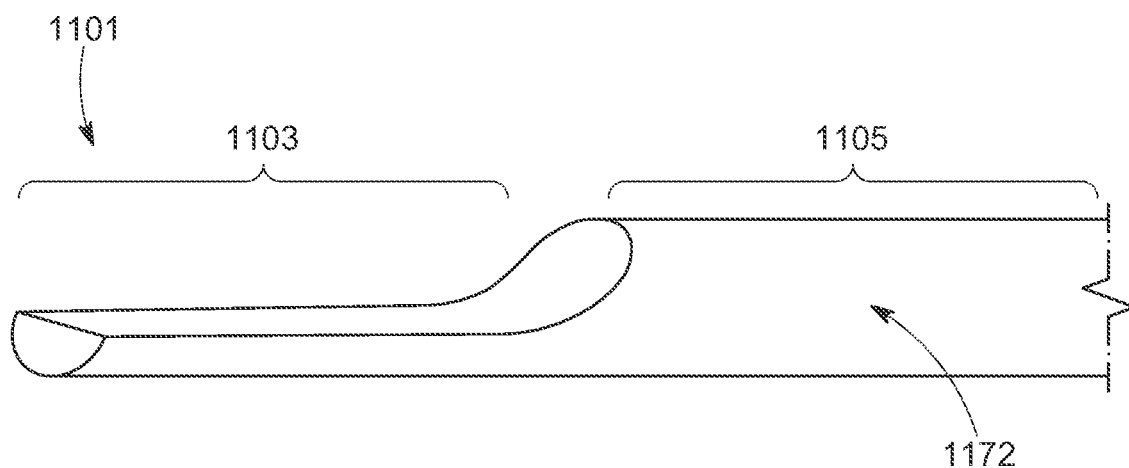
FIG. 11 shows an embodiment of a multi-denier monofilament suture.

Referring to FIG. 11, in some embodiments, a multi-denier yarn 801 can be formed of a single monofilament 872, such as a polymer monofilament. The multi-denier yarn can thus include a low denier segment 803 having a smaller denier than a high denier segment 805. The smaller denier segment 803 can be formed by removing a portion of the monofilament, such as through milling.

Figure 25:
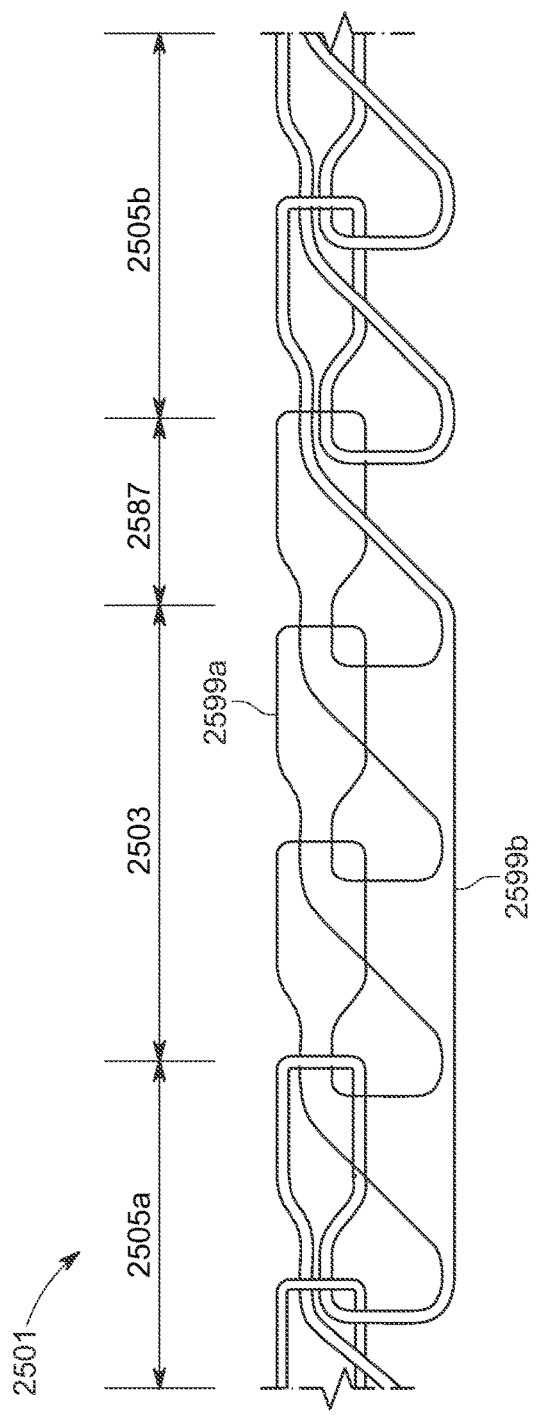
FIG. 25 shows an exemplary multi-denier yarn having multiple yarn elements and at least one warp-knit pillar stitch.

Referring to FIG. 25, a multi-denier yarn 2501 can include lower denier segment (or segments) 2503 and higher denier segments 2505a,b. Segments 2505a,b can have a greater number of strands than segment 2503 such that segments 2505a,b have a higher denier than segment 2503. A transition zone 2587 can be located between each segment 2505, 2503. The multi-denier yarn 2501 can be formed of two or more yarn elements 2599a,b. Each segment 2505a,b of higher denier can be formed of more loops than a lower denier segment 2503. For example, in FIG. 25, low denier segment 2503 is formed by knitted or crocheted loops (i.e. pillar stitches) of yarn element 2599a with yarn element 2599b forming a weft yarn outside of the pillar stitch of yarn elements 2599a. In contrast, high denier segments 2505a,b is formed by looping or forming pillar stitches with yarn element 2599a and yarn elements 2599b. For example, as shown in FIG. 25, the segments 2505a,b can include both yarn elements 2599a,b looped together in parallel. The yarn element 2599a can have repeated pillar stitches extending the entire length of the yarn 2501.

Figure 26:
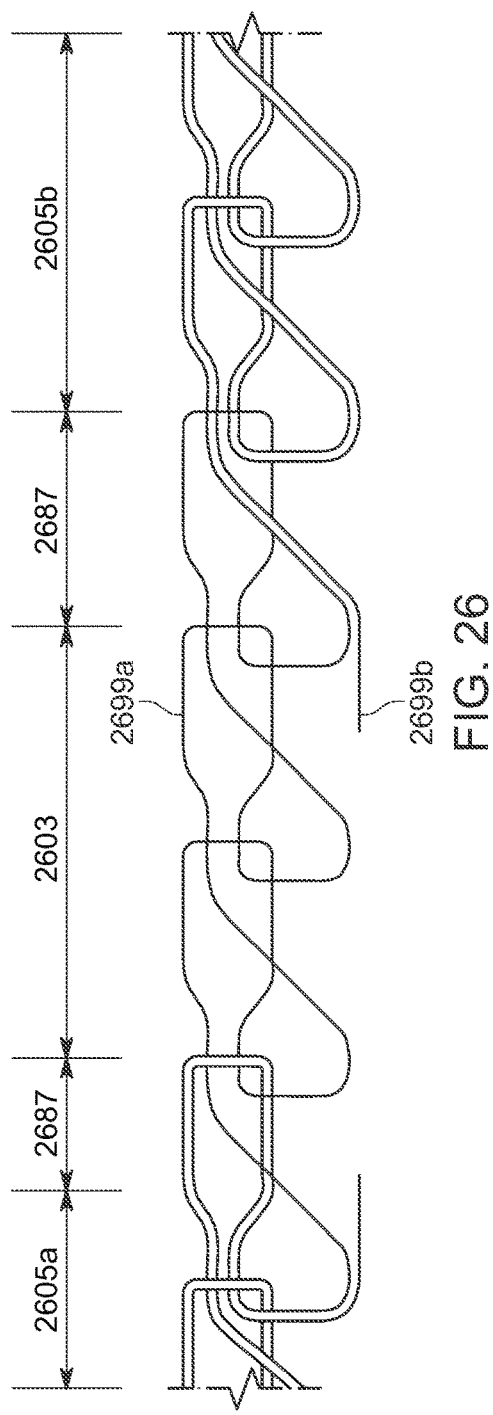
FIG. 26 shows an exemplary multi-denier yarn having multiple yarn elements, at least one pillar stitch, and a cut in a yarn element.

Referring to FIG. 26, a multi-denier yarn 2601 can include can include lower denier segment (or segments) 2603 and higher denier segments 2605a,b. Segments 2605a,b can have a greater number of strands than segment 2603 such that segments 2605a,b have a higher denier than segment 2603. A transition zone 2687 can be located between each segment 2605, 2603. The multi-denier yarn 2601 can be formed of two or more yarn elements 1599a,b. Similar to FIG. 25, the higher denier segments 2605a,b can have loops or pillar stitches formed of more than one yarn element 2699a,b while the lower denier segment 2603 can have loops or pillars formed of fewer (e.g., only one) yarn elements 2699a. In FIG. 26, the weft yarn element 2699b can be cut at the transition zone 2687 to lower the denier of the segment 2603 relative to the denier of segments 2605a,b.

In another warp knitted embodiment, longitudinal yarn elements are captured in some areas by pillar stitches, and in other areas, the longitudinal yarns run parallel to the pillar stitches. The longitudinal yarns in this embodiment thus do not form loops. In areas where the yarns are parallel to the pillar stitch, the yarns may be cut away in a secondary operation, leaving reduced denier in zones where there are only pillar stitches.

Figure 27:
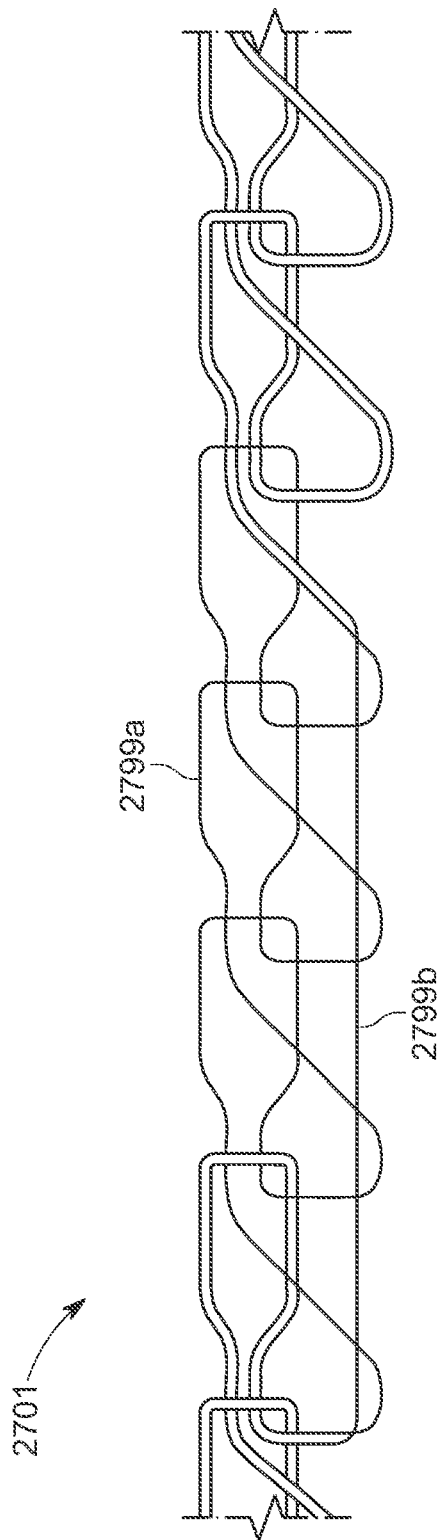
FIG. 27 shows an exemplary multi-denier yarn having multiple yarn elements, at least one pillar stitch, and a weft yarn integrated with the pillar stitch.

Referring to FIG. 27, in some embodiments, a multi-denier yarn 2701 can include the same or similar features to the multi-denier yarn 2501 described with respect to FIG. 25 except that the weft yarn element 2799b can be integrated with, intertwined with, or captured by the yarn element 2799a forming the loops or pillar stitches.

Figure 28:
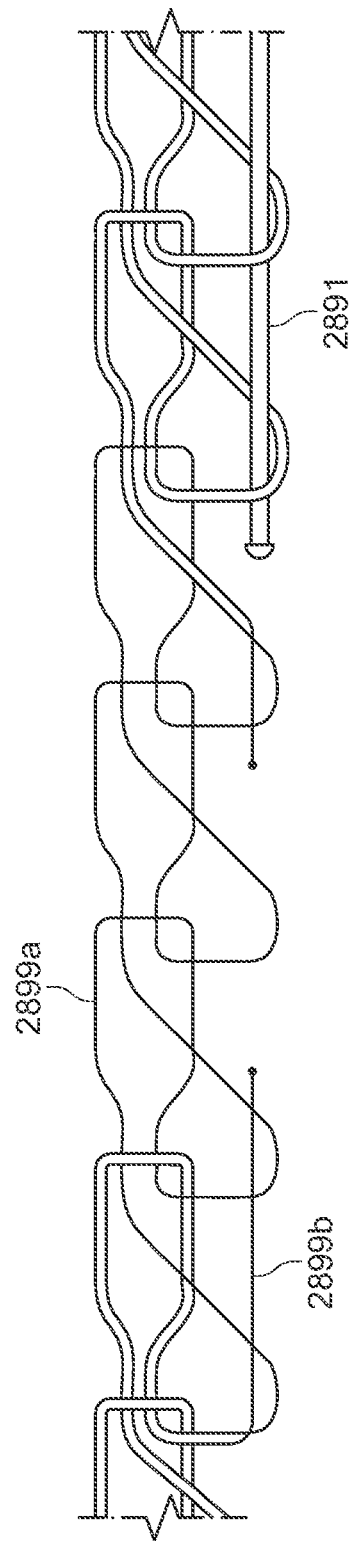
FIG. 28 shows an exemplary multi-denier yarn having multiple yarn elements at least one pillar stitch, a weft yarn integrated with the pillar stitch, and a cut in the weft yarn.

Referring to FIG. 28, in some embodiments, a multi-denier yarn 2801 can include the same or similar features to the multi-denier yarn 2601 described with respect to FIG. 26 except that the weft yarn element 2899b can be integrated with, intertwined with, or captured by the yarn element 2899a forming the loop or pillar stitches. A weft yarn element 2891 can be placed to be captured by the pillar stitch without integrating into the pillar stitch at any point, and it may run parallel and outside the pillar stitch according to knit pattern. Yarn element 2891 may be cut away in zones where it runs outside the pillar stitch, to reduce the denier of the cross-section.

Figure 29:
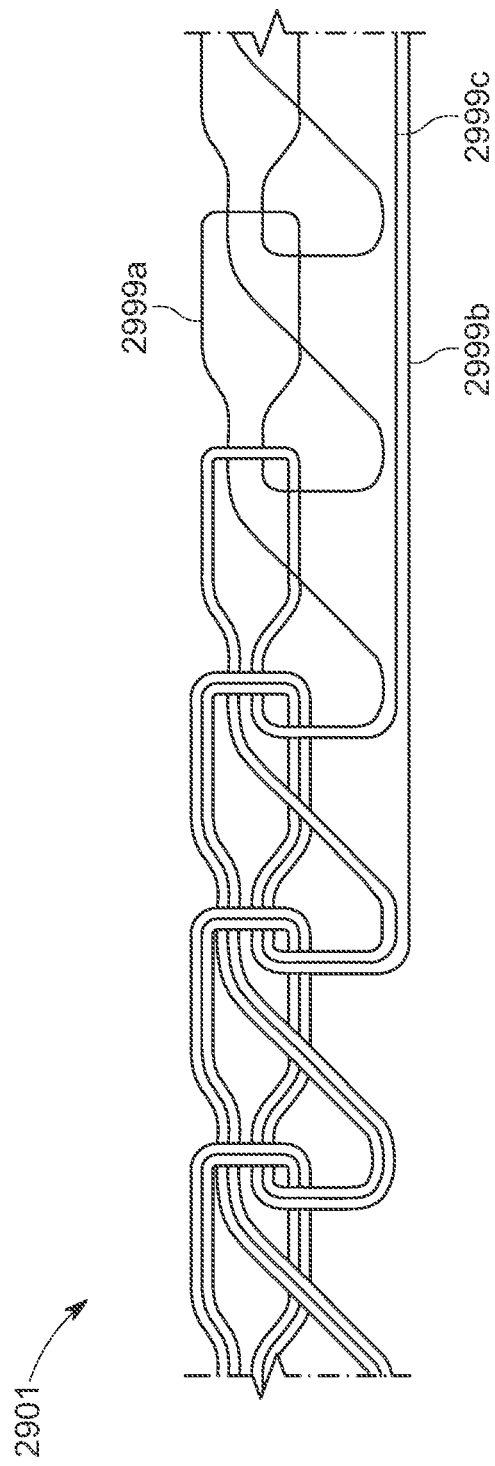
FIG. 29 shows the stepwise exit of yarn elements form a pillar stitch.

Although FIGS. 25-28 have been described as including only two different yarn elements and two different deniers, it is to be understood that other combinations are possible. For example, as shown in FIG. 29, there could be three different yarn elements, and there could be several different segments of different denier created by loops formed of one, two, or three of the yarn elements. As shown in FIG. 29, a multi-denier yarn 2901 having three yarn element 2999a,b,c can include a step-wise transition from a higher denier to a lower denier by removing one yarn element 2999b from the pillar stitch and then another yarn element 2999c from the stitch further down the yarn 2901. Further, combinations of any of the features of one yarn of FIGS. 25-28 can be included with features of any other to vary the denier of a yarn.

Figure 30:
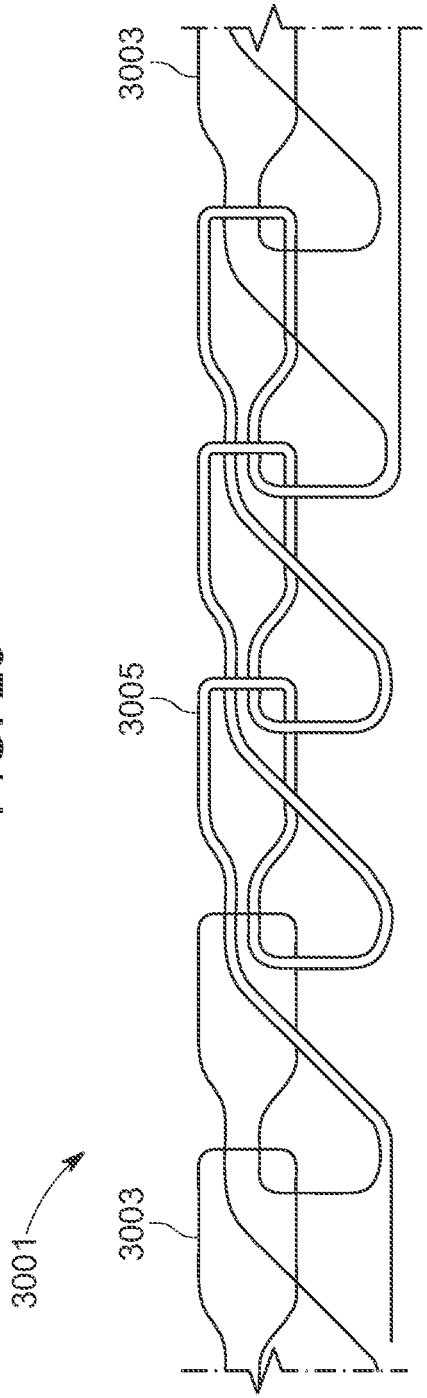
FIG. 30 shows a multi-denier yarn having a central portion of greater denier.

In some embodiments, at least one yarn element in the multi-denier yarns of FIGS. 25-29 can have a denier different than other yarn elements. The denier of each segment can be controlled based upon which yarn element is used to form the loops or pillar stitches. In some embodiments, at least one segment can have no pillar stitches, such as have all of the yarn elements extending in parallel. Further, the yarns described with respect to FIGS. 25-29 can have any number and order of lower and higher denier segments. For example, referring to FIG. 30, a multi-denier yarn 3001 can have a high denier segment in the middle surrounded by two low denier segments.

The multi-denier yarns of FIGS. 25-30 can be made, for example, using a Warp Knitting Machine with Weft Insertion, MDC 8/630, manufactured by Jakob Mueller AG, 5070 Frick, Switzerland.

In embodiments of the multi-denier yarns described herein, the aspect ratio of the distance between segments of different denier and the width of a yarn element can be greater than 100, such as greater than 200, greater than 500, or greater than 1,000. For example, the distance between segments of different denier can be between 5 and 100 cm. In some embodiments, each transition zone is substantially equidistant. In other embodiments, each segment of the same denier has the same length. In yet other embodiments, repetition of transition zones between repeating segments is at regular intervals. Moreover, where the multi-denier yarns described herein change in denier, the change can be greater than 10%, such as by a factor of two or more.

In some embodiments, the distance between transition zones can be short, e.g., 5-10 mm, so that the yarn includes a large number of segments. In other embodiments, the distance between transitions zones can be long, e.g. 10-50 cm apart, so that yarn includes only a few, e.g., less than 10, such as only two, different segments.

In embodiments of the multi-denier yarns described herein, the yarn includes one or more low denier segments and one or more high denier segments. Further, additional segments having a denier between the deniers of the low denier segments and the high denier segments can be present.

In embodiments of the multi-denier yarns described herein, each segment can have a substantially constant denier, i.e., can change by less than 5%, such as less than 1%, along the length of the segment. Further, the transition zones can include a sudden change in denier or can have a gradual change in denier, e.g., include a gradual decrease in the number of wales per course. Stated differently, the yarn can have a change in denier over a length being as shorter than 0.5% of the higher denier segment, or as long as 50% of the length of the higher denier segment, or can have gradually increasing and decreasing denier in a single length of yarn or in a repeating pattern over the length of the yarn.

In embodiments of the multi-denier yarns described herein, all of the yarn elements are made of the same denier and material. In other embodiments, at least one yarn element is made of a different denier or material. The yarn elements can be made of a material such as polyester, polyethylene, or polypropylene. Further, the multi-denier yarn can be substantially inelastic, e.g., the multi-denier yarn can be configured to rupture with less than 5% axial elastic strain.

Advantageously, the multi-denier yarns described herein can be made using an automated process without interrupting the linear continuity of the yarn and producing a repeating pattern of varying denier. In some of the embodiments of the multi-denier yarns described herein, standard commercial machinery can be used to manufacture the sutures. For example, the yarns described herein can be manufactured using a Shima Seiki SWG 041N machine, a Herzog LZ2 series machine, a Herzog NG2 series machine, a Comez DNB-800 machine for narrow nets, a Double Bar Raschel machine HDR8, or a Karl Mayer Double needle bed warp knitting machine.

Any of the multi-denier yarns described herein can be used independently as a completed textile, or as part of a composite or integrated structure, which in turn functions as a variable denier yarn or completed structure. For example, referring to FIGS. 12A-12C, an integrated structure 771 can include an outer thread 780 braided or wrapped around one or more of the multi-denier yarns 701 such that the multi-denier yarn acts as an axial center of the integrated structure 771. Alternatively, an integrated structure could be made by braiding or winding one or more multi-denier yarns together. The independent or composite structure can be, for example, a suture for use in surgical procedures, without further modifications other than cutting it into lengths for use, tipping, etc.

Referring to FIG. 12B, a single multi-denier yarn 701 can be wrapped or braided in an outer thread 780. In contrast, referring to FIG. 12C, the composite structure 771 can include multiple multi-denier yarns 701a, 701b wrapped or braided in an outer thread 780. As shown in FIG. 12C, the high denier portions 705a, 705b of the multi-denier yarns 701 can be staggered axially so as to create three sectors 773, 775, 777 of variable denier along the composite structure 771. That is, where the high denier segments 705a, 705b line up axially, the denier of the sector 777 will be greater. At the staggered portion (sector 775), the denier of sector 775 will be lower, and where the low denier segments align (at sector 773), the composite 771 will have an even lower denier. Further, referring to the yarns 901a, 90b of FIGS. 7A and 7B, the transition zones may be knitted so that they are staggered along the length of the suture to avoid having a lump in the yarn caused by having multiple transition zones positioned at the same axial location.

Figures 13A, 13B:
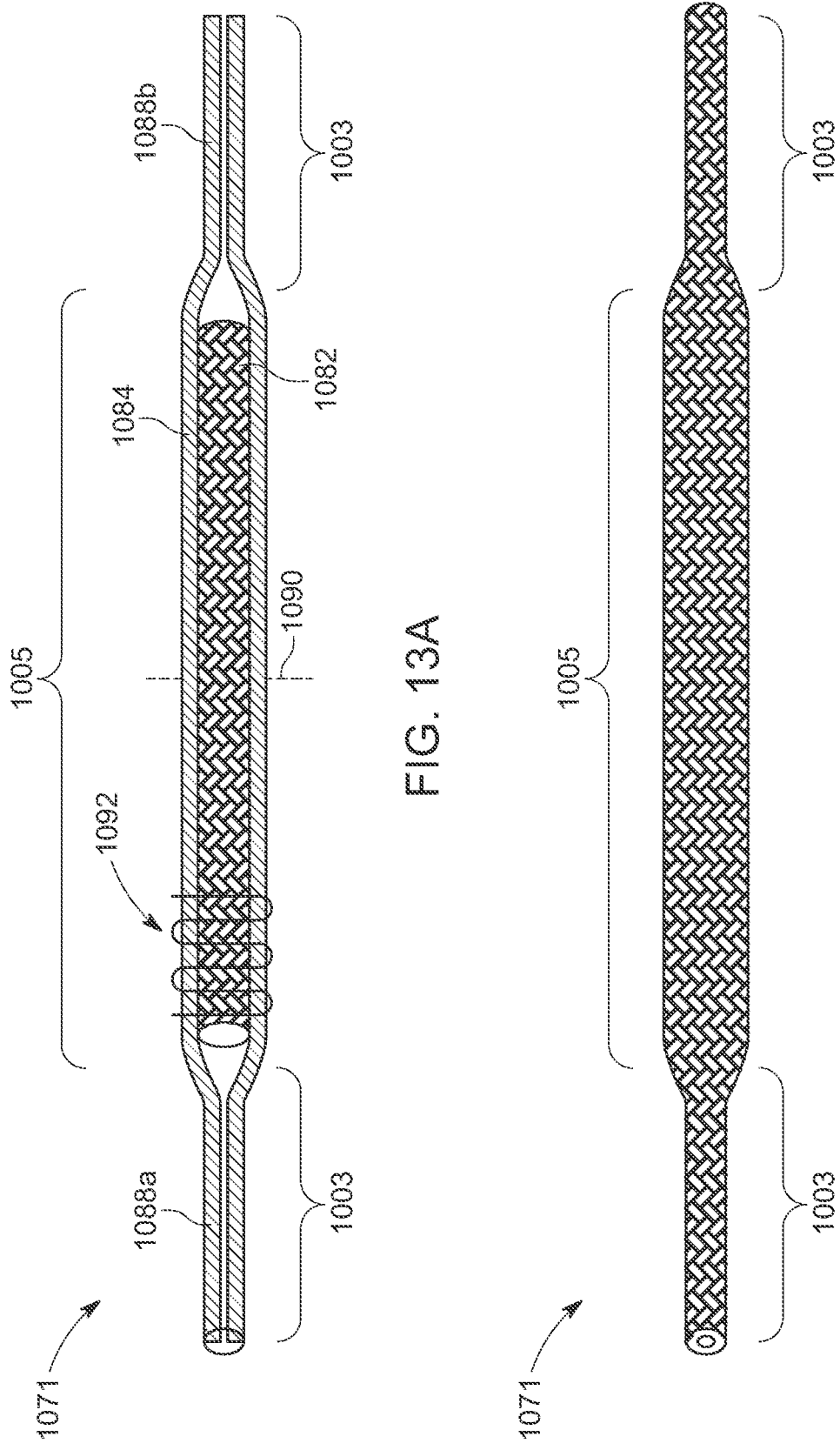
FIGS. 13A-13B show an embodiment of a variable denier surgical suture.

Referring to FIGS. 13A and 13B, an integrated structure 1071 can be formed of single-denier inner element 1082 introduced by textile process inside an outer thread 1084. The single-denier inner element 1082 can have a shorter length than the outer thread 1084 to as to create a segment 1005 of greater denier than an adjacent segment 1003. In one embodiment, the integrated structure 1071 can be formed by knitting, braiding, or weaving one structure over the other. In another embodiment, the integrated structure 1071 can be formed by braiding outer thread 1084 over inner element 1082 in a continuous uninterrupted fashion, where the inner element 1082 is introduced intermittently as an axial yarn. In another embodiment, the composite structure 1071 can be formed by introducing the single-denier inner element 1082 into the radial center of the outer element 1084.

Additionally, the inner element 1082 and outer element 1084 can be supplementally secured by sewing one or more stitches 1092 and/or by use of adhesive 1094. In some embodiments, the inner element 1082 can be a tubular braid, advantageously facilitating automated textile processes and also allowing the central portion of the suture to function as a Chinese finger trap-type lock, as described further below. The inner element 1082 can have a greater denier than the outer element 1084. This makes the denier of the folded and doubled first segment less than the denier of the second segment so that at maximum fill of the passageway, the fit of the second segment is tighter than the fit of the folded first segment, as described further below.

In one embodiment, the inner element 1082 can be produced as a braid with a core yarn, or axial yarn. This core yarn may be a monofilament or a braid, and the core yarn may be colored. To vary the denier of the suture 1071, the side of the braids of both the inner and outer elements 1082, 1084 may be spread apart to expose the core yarn, and then one end of the exposed core yarn can be pulled out. This may be repeated at another location on the second segment, pulling the other end of the core yarn out, to thereby create a yarn 1071 having multiple changes in denier. In some embodiments, the core yarn may be exposed in strategic locations to be used as a passing loop, or using this core yarn to pull a passing loop into the desired portion.

In another embodiment, if an integrated structure 1071 is produced with an inner element 1082 having a length longer than the desired final length, one or both ends 1088a, 1088b of the outer element 1084 can be pulled towards the axial center 1090 of the composite structure 1071 to expose the inner element 1082, and then desired amount of the inner element 1082 can be removed. An alternative way to remove part of the inner element 1082 is to introduce a thin cutting tool inside the tube of the outer element 1084, to the depth where the inner thread is to be cut, and cutting it off with the tool, and then removing the unwanted portion of inner thread. Yet another way to remove a portion of the inner element 1082 is to spread the yarns of the outer element 1084, pull the inner element 1082 out through the opening in the outer element 1084, and cut off the desired amount, similar to as described above.

In some embodiments, the integrated structure 1071 can also be formed by placing the inner element 1082 within an already braided outer element 1084. This can be done by attaching the inner element 1082 to a traction loop, placing the traction loop along the axis of the outer element 1084, and pulling the traction loop, and thus the inner element 1082 to the desired position. In some embodiments, a traction loop can penetrate out the side of the outer structure 1084 and be used to pull the inner element 1082 into the outer element 1084, e.g., along the central longitudinal axis. Additional techniques may be used to place the inner element 1082 into the outer element 1084, or to remove portions of the inner element 1082 from the outer element 1084.

Figure 31:
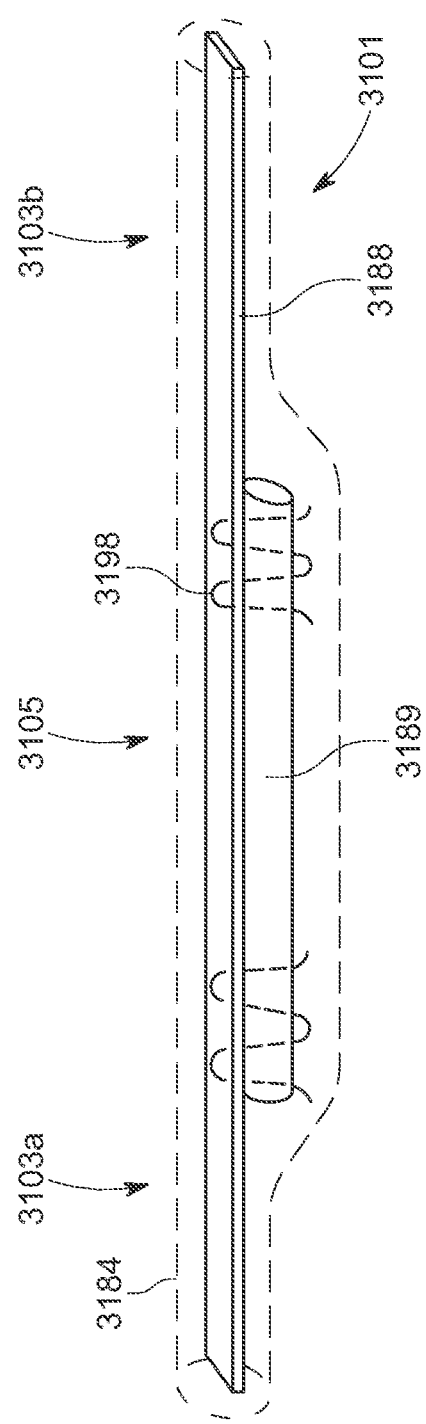
FIG. 31 shows a multi-denier yarn having a core element and a secondary element sewn thereto.

Referring to FIG. 31, a multi-denier yarn 3101 can include a core element 3188 having a length greater than a secondary element 3189. The secondary core element 3189 can be attached to the core element 3188 to make a segment 3105 having a higher denier than the low denier segments 3103a,b. The secondary core element 3189 can be attached to the core element 3188 by a stitched, zig-zag stitched, knitted, or warp knitted thread or by adhesion. Further, the multi-denier yarn 3101 can include a tubular outer layer 3184, such as a tubular overbraid.

Figure 32:
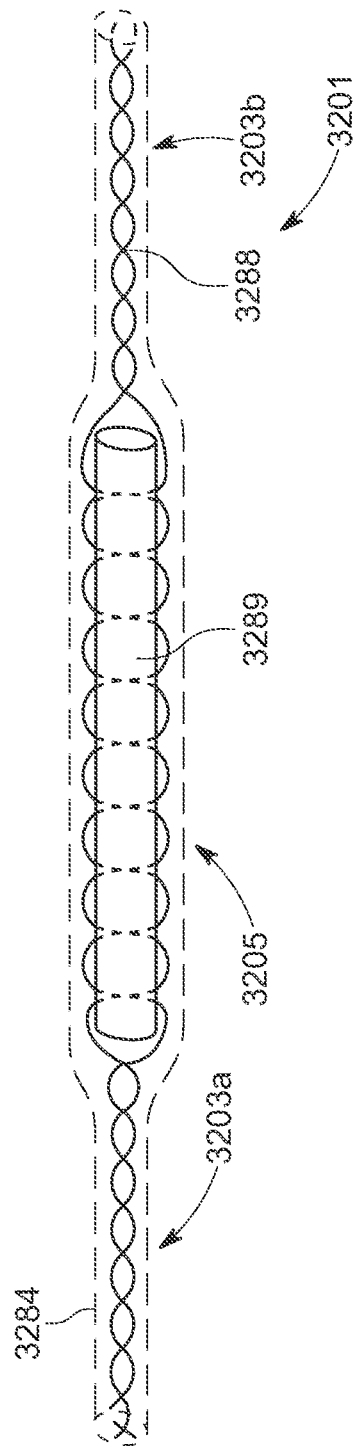
FIG. 32 shows a multi-denier yarn formed by one or more threads extending over a secondary element in at least one segment.

Referring to FIG. 32, a multi-denier yarn 3201 can include a higher denier segment 3205 and one or more lower denier segments 3203a,b. A core element 3288 of the yarn 3201 can be formed of one or more threads that extend in parallel or that are integrated together. The core element 3288 can be attached in the high denier segment 3205 to a secondary core element 3289. The threads of the secondary element 3288 can be sewn around or through the core element 3288 to attach the core element 3288 and secondary element 3289 together. Further, the multi-denier yarn 3201 can include a tubular outer layer 3284, such as a tubular overbraid.

The multi-denier yarns 3101 and 3201 can have multiple high denier and low denier segments. That is, the core element can include several secondary core elements attached thereto and varying intervals. Further, the secondary elements can themselves have varying denier or can have a constant denier that is different from one or more other secondary elements.

The multi-denier yarns 3101 and 3201 can advantageously be sewn in a continuous automatic process. Further, the overbraid can be applied in a continuous automatic process, creating a long uninterrupted suture structure with periodic variation in the denier. This automated process can reduce the production expense associated with the yarn or suture.

Figure 19:
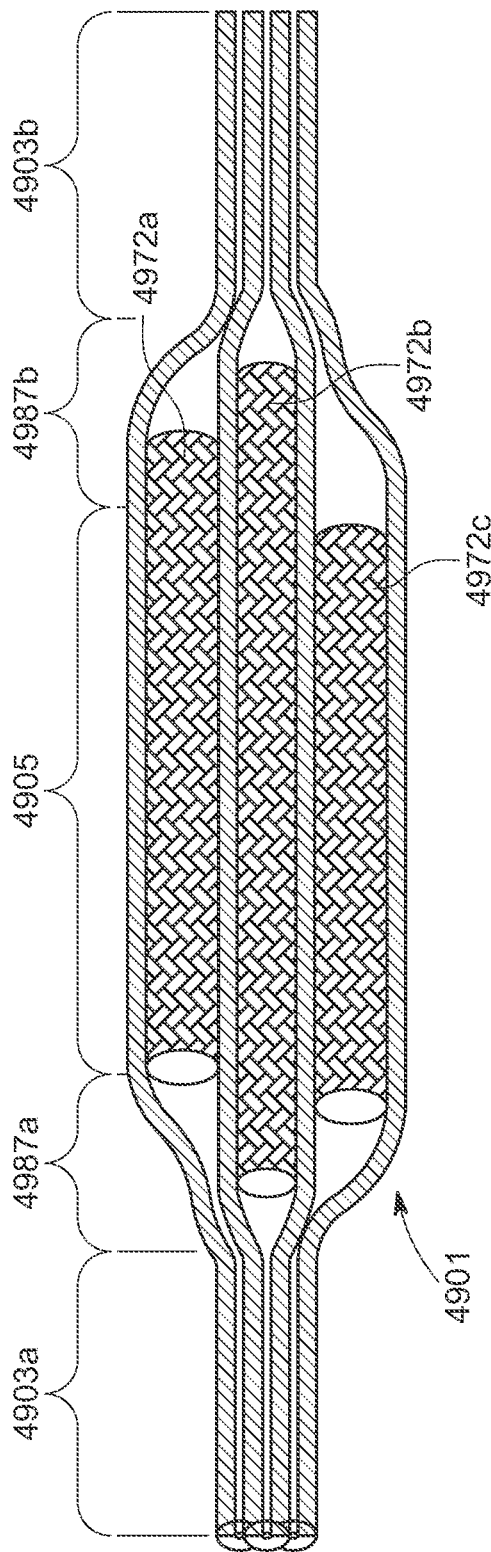
FIG. 19 shows a multi-denier suture having multiple cores.

Referring to FIG. 19, in one embodiment, a multi-denier structure 4901 includes a plurality of side-by side inner elements 4972a-c, such as tubular braids or twisted yarns. Further, an outer element 4984 can extend or be integrated around the inner elements 4972a-c, e.g., using a braiding machine to form the higher and lower denier segments 4905 and 4903a,b, respectively. In some embodiments, the inner elements 4972a-c can be staggered with respect to one another such that their terminations are staggered, thereby causing a slower change in denier at the transition zones 4987a,b. The suture 4901 can advantageously be flat so as to be used, for example, as a suture tape. In some embodiments, the suture 4901 can be made similar to a president's braid (e.g., with the same braiding machine used for a president's braid). In one embodiment, the inner elements 4972 a-c can be continuously overbraided so that each is enclosed in a tubular braid with the tubular structures sharing at least some the yarns among all tubular structures. Production of the multi-denier structure 4901 can advantageously be fully automated, and the multi-denier structure 4901 can be made in relatively small sizes, i.e. the central portion 4905 can have a denier equivalent to or as small as United States Pharmacopoeia (USP) No. 2.

Figure 23:
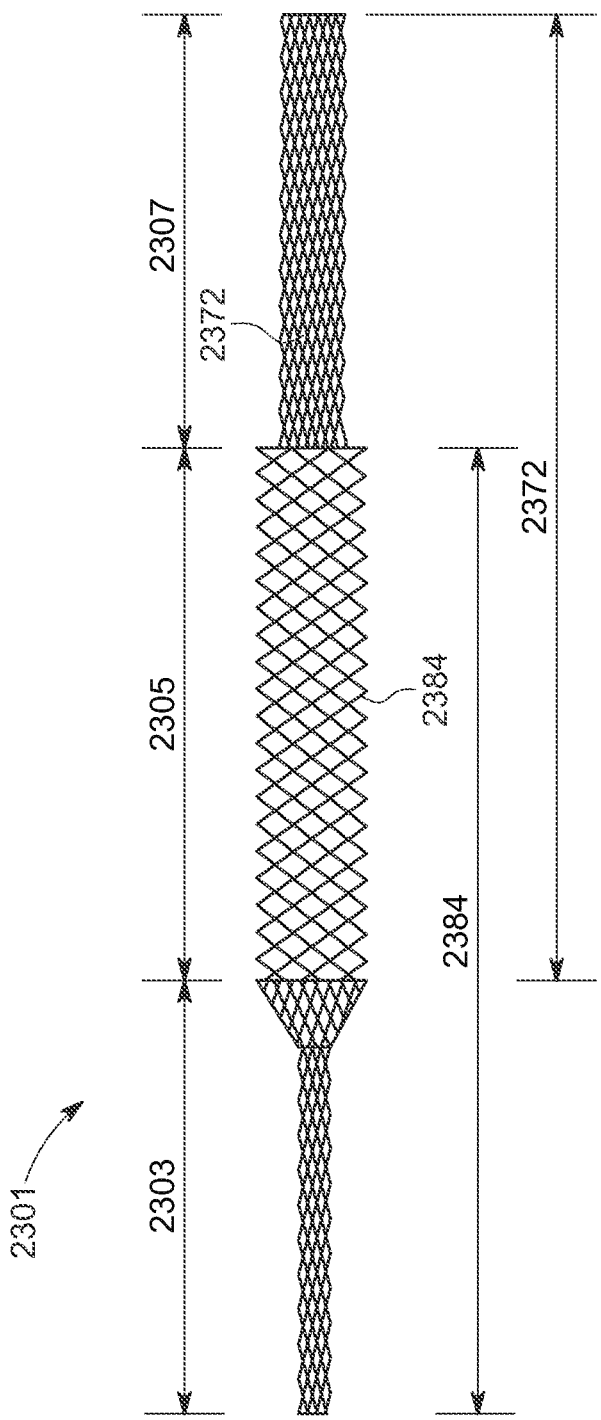
FIG. 23 shows a multi-denier structure having a partially exposed inner core.

Referring to FIG. 23, in one embodiment, a multi-denier structure 2301 includes an inner element 2372 with an outer element 2384 extending over the inner element 2372. The outer element 2384 can extend past the inner element 2372 to form a first segment 2303 of a lower denier than a second segment 2305. Further, the outer element 2384 can be pulled away to form a third segment 2307 of different denier than the first and second segments 2303, 2305. In some embodiments, the third segment 2307 has a denier between the first and second segments 2303, 2305. The multi-denier structure 2301 thus has three segments: a first segment 2303 with a cross-section including only the outer braid 2384, a second segment with a cross section including both the outer braid 2384 and the inner element 2372, and a third segment 2372 including only the inner element 2372.

The structure 2301 can be assembled and used by the manufacturer, assembled in a manufacturing process for surgeon use, or the necessary components can be provided to the surgeon for assembly and use by the surgeon. The outer braid 2384 can be positioned to cover part or most of the inner element 2372. The inner element 2372 may function as the main or principal suture element, or may be designed to serve together with the outer braid 2384. The inner element 2372 may be a braided element. After the outer braid 2384 is positioned over the end of the inner element 2372, the two elements together become a form of variable denier suture 2301.

In use, the first segment 2303 may be used to apply traction to the rest of the suture so as, for example, to pull the higher denier segments 2305 into a passageway (such as a lock, etc.), as described further below. The first segment 2303 may also be used to pull the third segment 2307 into the passageway. After the inner element 2372 is placed in the passageway, the outer braid 2384 may be removed by sliding the outer braid 2384 off of the inner element 2372, or the portion of suture including the outer braid 2384 may be cut away.

In some embodiments, the outer braid 2384 has a denier that is less than denier of the inner element 2372. The outer braid 2384 can be braided such that the denier of the outer braid 2384 is less than the denier of the inner element 2372. The outer braid 2384 can have a denier of less than ⅕ of the denier of the inner element 2372. The yarns of the outer braid 2384 may be poly filament or monofilament. Monofilament yarns may be heat-fused together without a burr. The yarn material may be any polymer material that is used for fabrication of sutures.

In some embodiments, the structure 2301 may be manufactured by producing a continuous braid having a core element. The continuous braid can then be cut to the desired length. In one embodiment, the core element can be grasped at the exposed end, the outer braid can be held near the same end, and the core element can be slid partially out of the outer braid. In another embodiment, the core element may be pulled partially into an outer braid with a passing loop, leaving part of the core element exposed. In another embodiment, the structure 2301 can be made from a continuous braid where, after cutting the braid into segments, the core element is exposed through the side wall of the outer braid, grasped, and one end of it pulled out through a side-wall and the other end of the core element pulled partially out from the end. Parts of the exposed core element may be cut off and removed. In yet another embodiment, the core element may be pulled into the axial space of the outer braid with a traction element that is introduced along the axial space of the outer braid. This traction element may penetrate the side wall of the outer broad, to enter the core element at a location of the outer braid other than the end.

Figure 14A:
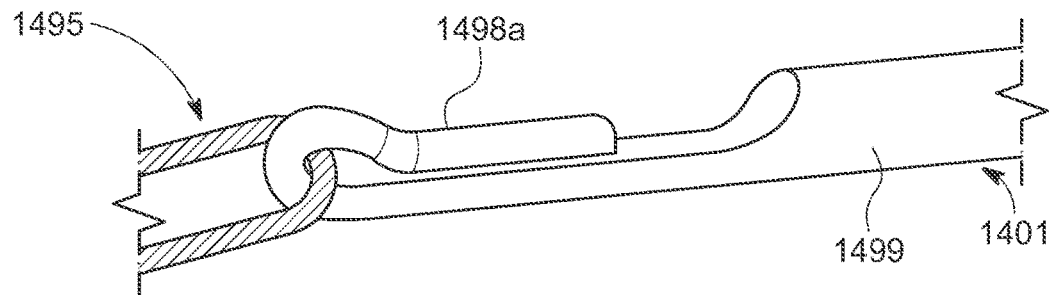
FIGS. 14A-14B show use of a multi-denier suture.
Figure 14B:
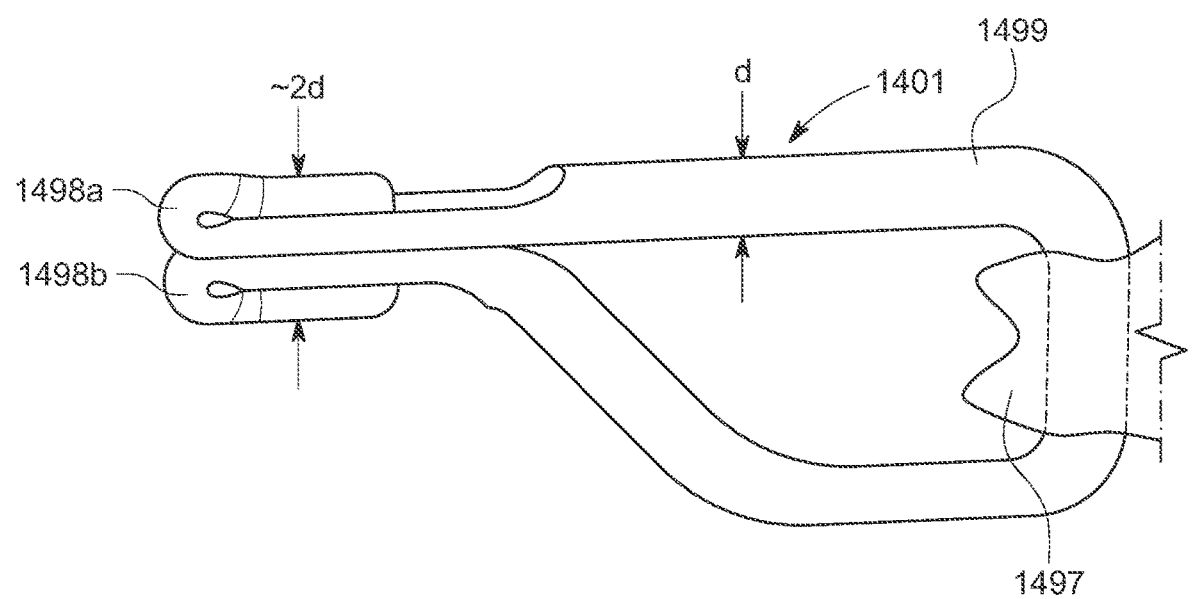

The structures described herein can advantageously be used as a suture during surgical procedures. Referring to FIG. 14A, the low denier portions 1198 can be at the ends of the suture 1101, allowing the suture 1101 to be wrapped around a traction loop 1195 so as to be more easily threaded through a small opening in a surgical instrument, surgical implant, or suture lock. For example, the ends 1198 of the suture 1101, when folded together, can have an equivalent or smaller diameter of the central portion 1199 of the composite structure. In use, therefore, the low denier portions 1198 can be placed straight or looped through a small opening, and traction can be applied to the low denier portion 1198 such that the low denier portion 1198 is first pulled through the hole. Then the high denier central portion 1199 is pulled through the opening, more nearly filling the entire dimension of the hole. Further, referring to FIG. 14B, in use, the high denier central portion 1199 can be placed against soft tissue 1197 being repaired. The lower-denier ends 1198a, 1198b can later be cut off and removed. Having the high denier portion against the tissue, with greater side profile, can advantageously increase the stability of the suture in the tissue. The suture 1101 can be any of the multiple-denier structures described herein.

Moreover, the multi-denier suture 1101 can advantageously provide for stronger lockings than traditional single denier sutures. Exemplary suture locks with which a suture as described herein can be used include a cinching suture lock (e.g., a lock used on a longitudinal structure, such as a cord, that allows tightening in one direction, but does not allow sliding loosening in another direction), a static force pinch-lock, a wedge lock, cam lock, a lock based on the Chinese fingertrap mechanism, or a double-ring lock. The locks based on the Chinese-finger-trap mechanism can include cable-puller type locks, belt splices, and eye splices.

Figure 15A:
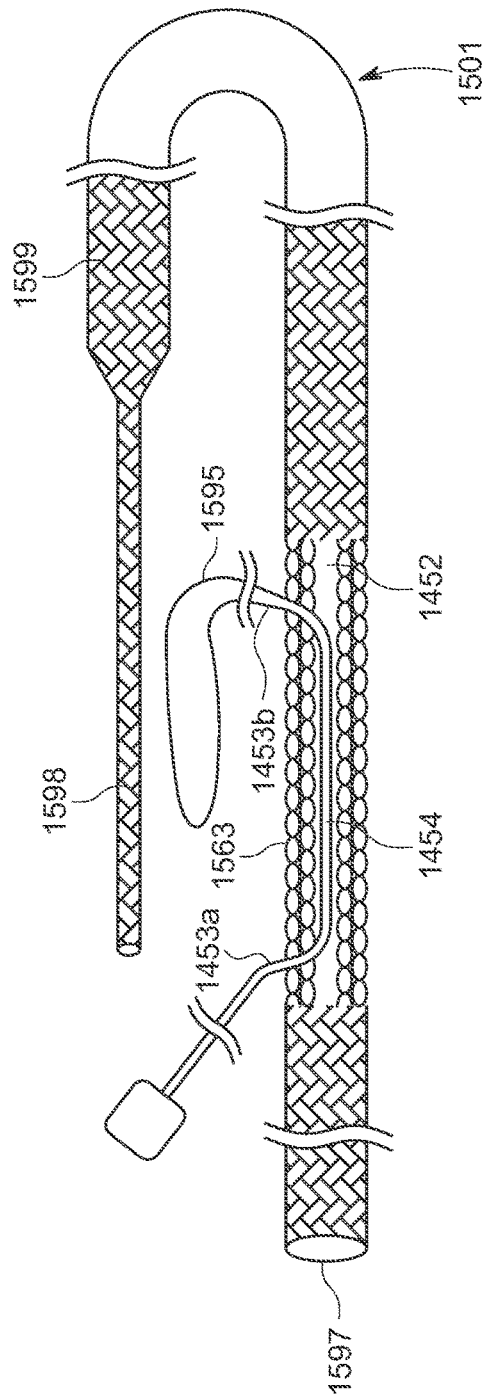
FIGS. 15A and 15B show a pull-loop through an inner channel of a multi-denier suture.
Figure 15B:
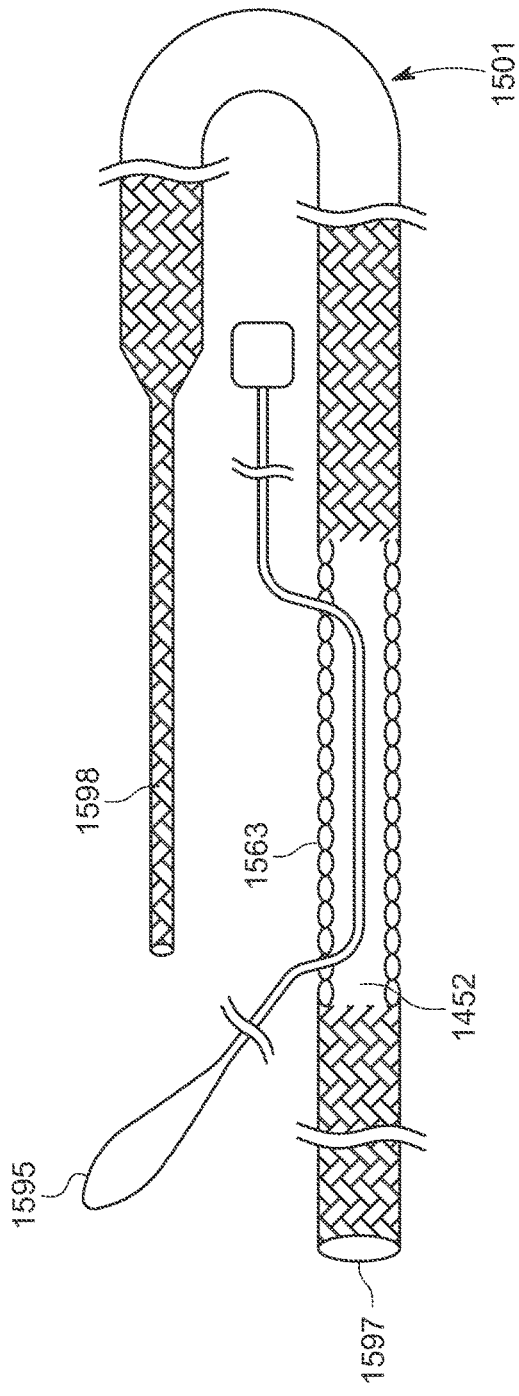

For example, referring to FIGS. 15A-15B, a multi-denier suture 1501 having a lower denier end 1598 and a high denier central segment 1599 can include a passage or channel 1452 therethrough. The channel 1452 can extend through the high denier central segment 1599, the lower denier end 1598, or both (the channel 1542 is through the central portion 1599 in FIGS. 15A-15B). The channel 1452 can include a middle portion 1454 and two end portions 1453a,b. In some embodiments, the hollow central column or radial core of a tubular braid can form the middle portion 1454. That is, the braid can be loose enough (e.g., have a low enough picks per length), such that there is an inner tubular space big enough to form a middle portion 1454 of the channel 1452. The end portions 1453a,b of the channel 1452 can extend through the walls 1563 of the suture 1501, such that there is passage through or between the yarn elements making up the suture 1501. The channel 1452 can be part of a cinching Chinese finger trap-type lock with a portion of the suture 1501 itself extending through the channel 1452. FIG. 15A illustrates the embodiment where the middle portion 1454 of the locking channel is surrounded by two layers of braid, providing increased locking force associated with tension on the suture. FIG. 15 B shows the embodiment where the middle portion 1454 of the locking channel is surrounded by a single layer of braid.

Figure 16A:
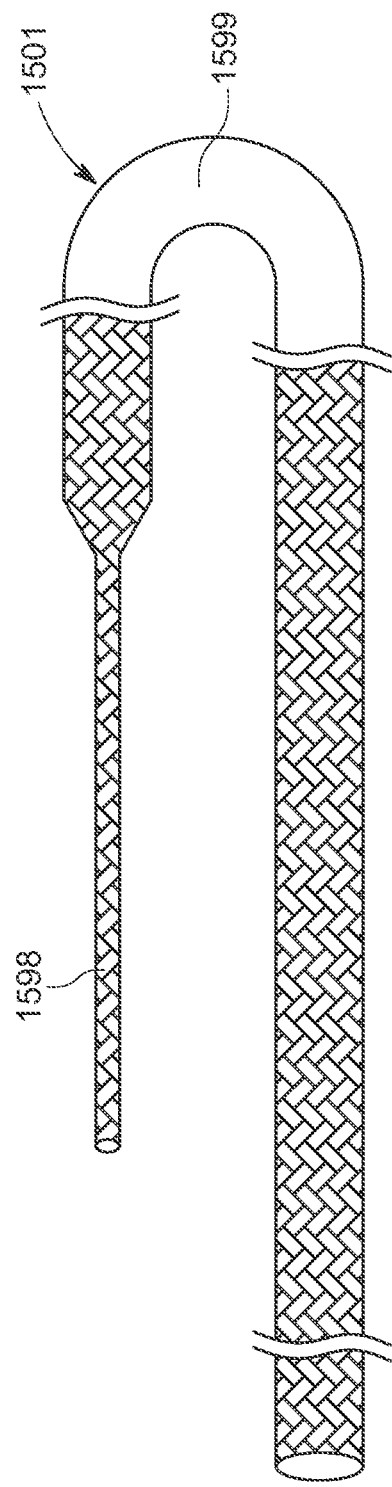
FIGS. 16A-16D show formation of a Chinese finger trap-type suture lock using a multi-denier suture.
Figure 16B:
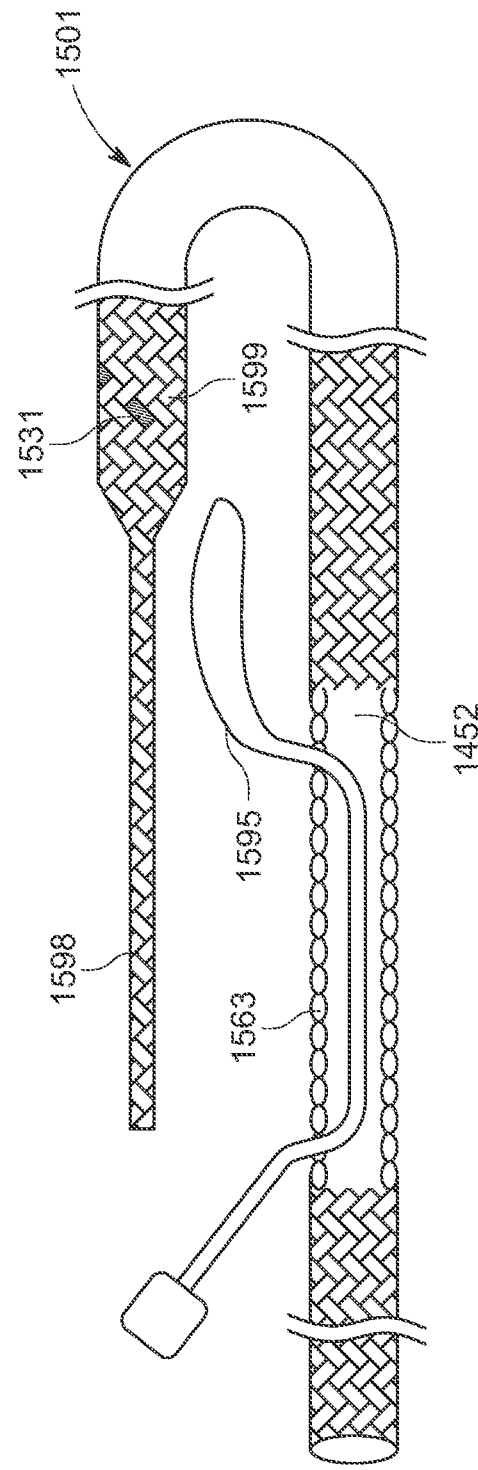
Figure 16C:
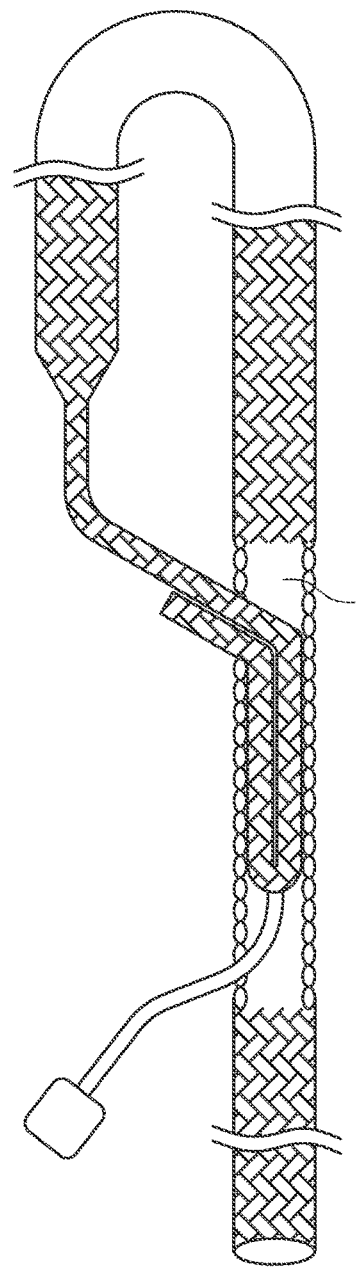
Figure 16D:
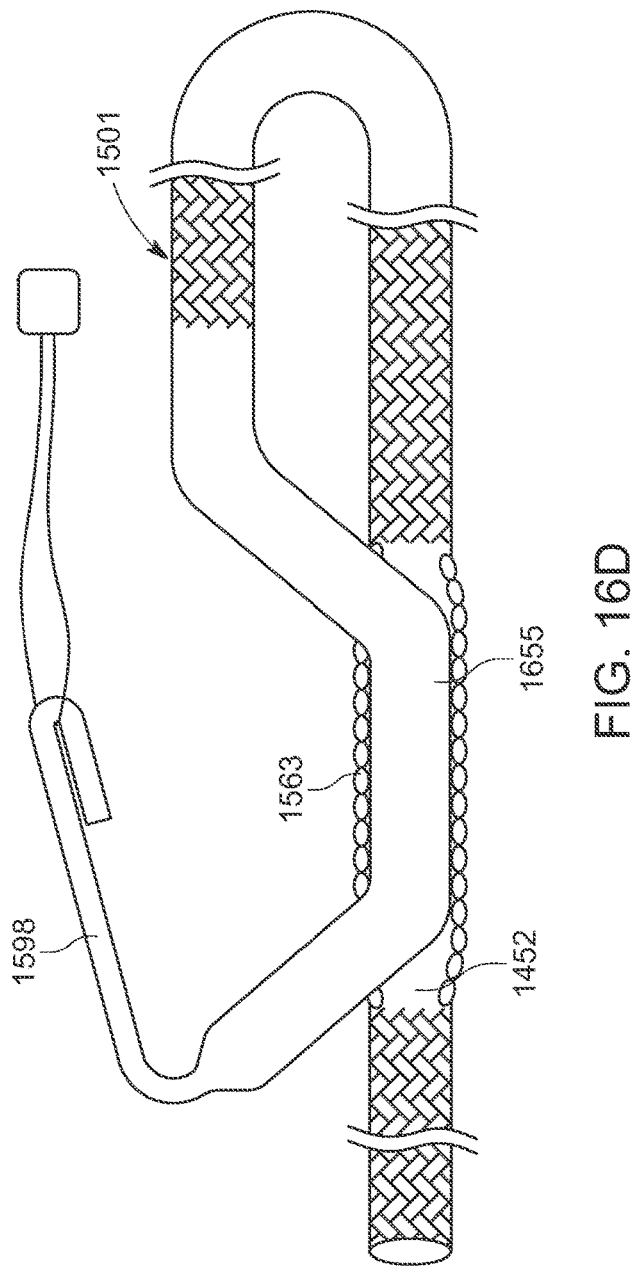

FIGS. 16A-16D show locking of a suture 1501 in a Chinese finger trap-type lock. As shown in FIG. 16B, a traction loop 1595 can be extended through the channel 1452. In some embodiments, the traction loop 1595 can be provided to the user already in place within the suture 1501. The suture 1595 can be threaded through tissue (e.g., the end 1598 can be looped through a needle as described above and pulled through tissue). After threading the suture 1501 through the tissue, the end 1598 of the suture 1501 can then be folded over the traction loop 1595 (e.g., such that the folded section can have a denier less than the denier of the folded higher denier central segment 1599, or preferably equal to or less than the denier of the central portion 1599), as shown in FIG. 16C. Referring still to FIG. 16C, the traction loop 1595 and folded end 1598 can then be pulled through the channel 1452. As shown in FIG. 16D, the traction loop 1595 and/or end portion 1598 can continue to be pulled until the higher denier central segment 1599 extends through the channel 1452. In some embodiments, the higher denier central segment 1599 can substantially fill any voids between the walls 1563 of the suture 1501. Further, in some embodiments, the higher denier central segment 1599 can expand the channel 1452 diameter (or radial distance between opposing walls of the suture 1501), as is allowed by the picks per inch of the braid. Once in place, the wall 1563 of the suture 1501 can act as a tightening force on the portion 1655 of suture 1501 that is resting in the channel, to resist axial movement of the suture 1501 within the channel 1452, thereby locking the suture in place. After the end 1598 is pulled entirely through the lock, it can be cut off of the rest of the suture 1501, but may be left in place, according to need.

Figure 17:
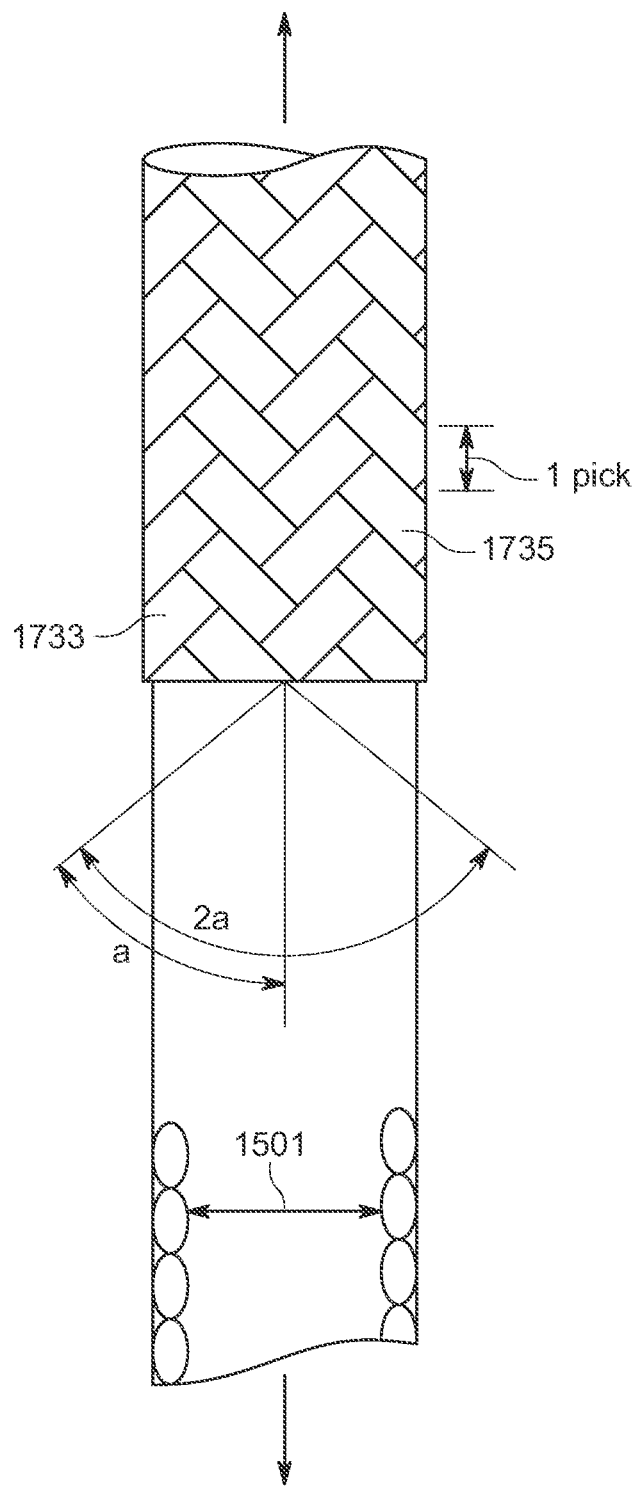
FIG. 17 shows the relation between the angle and tightness of a braid.

The suture 1501 described with respect to FIGS. 15A-16D can lock by a Chinese finger trap-type locking mechanism. Referring to FIG. 17, when tension is placed upon the braid (shown by the arrows in FIG. 17), the angle 2a between the right spiral threads 1733 and the left spiral threads 1735 reduces. This reduction reduces the radial distance between opposing inner walls of the suture 1501, thus reducing the cross-section of the channel. Referring back to FIG. 16D, the reduction in circumference places a tightening force or pressure on the portion 1655 of the central segment 1599 extending within the channel 1452, thereby preventing it from moving, and locking the suture 1501 in place. Advantageously, by having a segment 1598 of lower denier than segment 1599, the end segment 1598 can be easily pulled through the channel 1452 with the traction loop 1595 (i.e., such as doubled over the traction loop 1495) while allowing the higher denier segment 1599 to sit within the channel 1452 to lock the suture 1501 in place. That is, the pressure P placed on the portion of the suture within the channel is given by the following equation:

$$P = kT \tan \alpha$$

where k is a constant, T is the tension, and $\alpha$ is the angle between the braid yarn and the axis of the braid. The angle $\alpha$ increases with picks per length, or with the diameter of element running down the radial core of the suture. The steeper the braid angle $\alpha$, the more pressure applied by the braid in association with tension on the suture 1501. Maximizing the diameter of the portion 1655 inside the channel 1452 thus increases the locking force and friction on the portion 1655, increasing the force of the cinching locking mechanism overall.

The braid forming the suture can have a locking tightness that is multifactorial, controlled by picks per inch (ppi), number of carriers, braid pattern, dimension of axial yarn 1655, and tightness of the carrier springs in the braiding machine. However, the tightness of the braid (and thus the achievable width of the channel 1452) can be such that a doubled higher denier segment 1599 cannot pass there through even with angle α approaching 90°, but a single higher denier segment 1599 can pass through. In some embodiments, the circumference or cross-section of the higher denier segment 1599 is substantially equal to the widest achievable circumference or cross-section of the channel 1452 (i.e., when the angle α shown in FIG. 17 is as high as possible for the given braid, approaching 90°). In this relationship, the suture can act as a lock upon itself in the most effective way.

In embodiments where the multi-denier suture has an inner element and an outer element as in FIG. 15A, the inner element can have fewer yarns than the outer element. Fewer yarns permit the braid to achieve a higher alpha angle for a given total denier, and for the case of locking in the axis of the inner element, this allows a wider maximum passageway and superior locking.

Exemplary sutures having the picks per inch, number of carriers, braid patterns, dimensions, and tightness to function as a Chinese finger-trap type suture lock are provided below. Due to the differences in the specific gravity of various yarns, the examples provided are for a yarn having a specific gravity of 1.00. This denier would be increased by a factor of 1.4 for polyester or by a factor of 0.97 for polyethylene, for example.

In the first example, a 16-carrier regular braid made up of yarn elements of denier 90 is made in a way similar to the yarn 1801 of FIG. 8 (i.e., with a continuous braid forming both the higher and lower denier sections, with a fraction of the yarns removed in the lower denier section). The suture can be braided at 72 picks per inch which allows the same suture to be passed, with a loop 1595, down the central channel 1452 of the suture, filling the locking portion suture with a gentle friction fit. The lower denier first segment 1803a,b, reduced in denier to 30-40% of the second segment, can be doubled and pulled easily with a narrow wire loop through the central channel of the higher denier second segment 1805a. After pulling the looped lower denier first segment through, traction on the lower denier first segment pulls the higher denier second segment (16×1×90 denier) into the central channel with a gentle friction fit, without catching at the denier transition. To pull a loop of second segment 1805 into the same central channel, the channel must be greater than approximately 16×2×90 denier cross section. In the case of this example of 16 carriers×90 denier per carrier, the picks per inch must be reduced to 52 to allow passage of the 16×2×90 denier loop. Thus, in this example, the use of a lock with increased tightness of the braid from 52 to 72 picks per inch was made possible by the multi-denier suture described herein. Moreover, the multi-denier suture made it possible to lock with a much shorter length of locking channel 1452 and provided more secure locking.

A second example is a suture made similar to the yarn 1071 of FIG. 13 and suture 1501 in FIG. 15A The yarn denier is again normalized to a density of 1.00, a 16 carrier regular braid is used for the outer element 1084, and the yarn elements have a denier of 90. The inner element 1082 can be a tubular braid having the same properties as the outer element 1084, and a traction loop can be placed down the central channel of the inner element (and thus through the higher denier second segment). At 48 picks per inch and less, the second segment 1005 can be pulled easily into the locking channel. At 32 picks per inch and less, the doubled second segment can be pulled into the locking channel. Therefore, in this example, the multi-denier suture makes it possible to use a lock with tightness increased from 32 to 48 picks per inch. Moreover, passing the doubled first segment 1003 through the 48 ppi channel is much easier than passing the doubled second segment through the 32 ppi braid channel.

A third example again involves using a suture similar to the yarn 1071 of FIG. 13 and suture 1501 in FIG. 15A, but in this case, the higher denier second segment is locked in the lower denier first segment. Again, a 16 carrier regular braid is used and the same braid is used as both inner and outer elements. Here, the higher denier second segment can be passed through the central channel of the lower denier first segment when the ppi of the outer thread 1084 is equal or less than 52 ppi, and the doubled second segment can be passed with a braid equal or less than 36 ppi. In this case, the inner element serves as an expander to fill the suture lock, much as it is designed to fill the channel in other types of suture locks, including those shown in FIGS. 20A and 20B.

A fourth example is a suture with an outer braid and an inner element that is also a braid, such as shown in FIGS. 13, 15A, and/or FIG. 23. It is designed for the second segment to be locked in the axial channel of the same second segment of the suture at a different location, e.g., along the linear portion of the second segment. In this case, the outer braid has a denier that is less than the denier of the inner braid, for example 72 denier for the outer and 109 denier for the inner braid. The picks per inch of the inner braid are just high enough to accept passage of the second segment, in this case 56 ppi. The picks per inch of the outer braid is chosen to be 42 ppi, just high enough to accept free passage of the inner braid containing the second segment. In this way, the deniers for the outer and inner braids are adjusted to make the first segment have a denier less than half of the second segment, allowing very easy entry and passage of the looped first segment into and through the central channel in the second segment. Additionally, the picks per inch are adjusted to achieve maximal angle alpha for locking, in both the inner and outer braids; this maximizes the locking contribution of both inner and outer braids, minimizing the length of the locking channel required to achieve secure locking, and maximizing the locking pressure for a given tension on the lock. The same principles may be used for designing a suture with inner and outer elements that is intended to optimize passage and locking in the first segment. The same principles may be used for designing a suture having a single braid, where the first segment is made by terminating yarns or fibers in the transition zone, such as shown in FIGS. 8 and 15B, and where the second segment is locked in a channel of the second segment; the first segment can be chosen to have less than half the denier of the second segment, and the picks per inch of the second segment can be chosen to be just high enough to pass the second segment in its central channel.

Figure 18A:
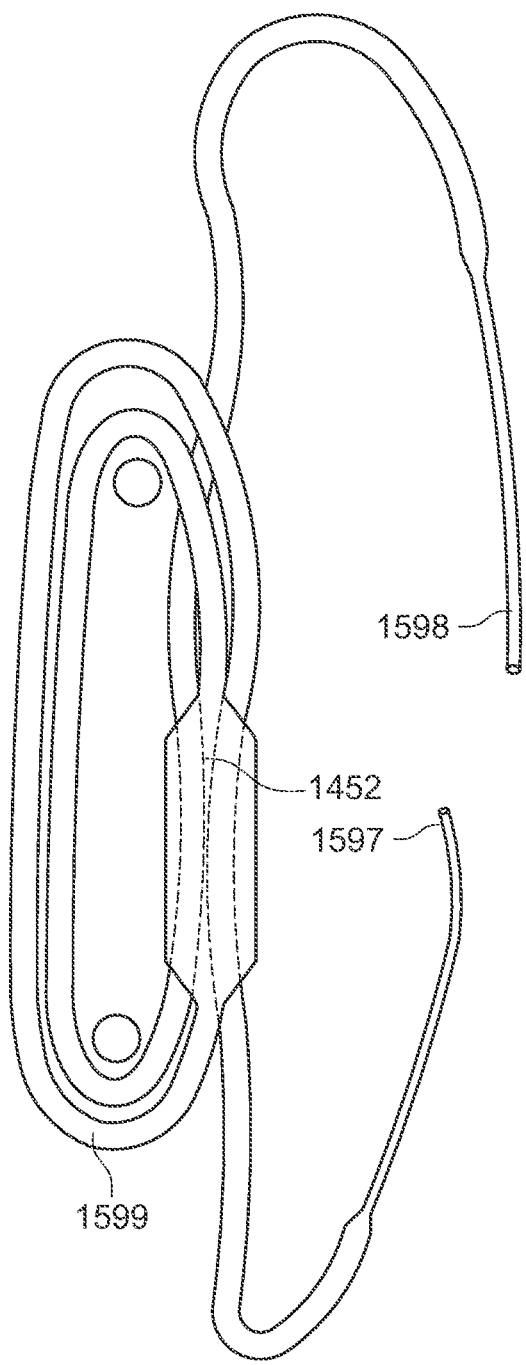
FIGS. 18A-18C show a double-lock Chinese finger trap-type suture.

A fifth example is that of a suture having an inner braid in the second segment, where a single locking channel in the second segment is designed to lock two ends of the second segment, the two ends passing in opposite directions, as shown in FIGS. 18A and B. The same optimization principles are used. In this case the lock must optimize locking on twice the denier instead of a single second denier. Again, 16 carrier regular braid is used for both inner and outer braids, and 72 and 109 deniers are used for the outer and inner braids, respectively. Here, 45 ppi for the inner braid and 36 ppi for the outer braid allows passage and optimizes locking.

The above examples provide approximations of the relations between carrier count, ppi, and denier required to optimize locking with the Chinese fingertrap mechanism. As shown by these examples, however, using a multi-denier suture can advantageously help achieve a much tighter locking than with conventional sutures, achieving much more secure locking. Further combining a multi-denier suture with proper ppi for the braid parameters optimizes the Chinese-finger-trap type locking characteristics of a suture, in sutures that are intended for such an application. For a tubular braid suture of the form of FIG. 8A, 8B, 10B or 15B, the segment 1805a, 2005b, or 1599 has a denier and ppi such that for maximum achievable angle α, the same portions 1805a, 2005b, or 1599 can still be passed down the central channel 1452, but the doubled central portions 1805a, 2005b, or 1599 cannot be passed down the central channel 1452. Similarly, for a suture of the form of FIGS. 15A and 13AB, picks per inch are adjusted so that for a maximum or near maximum angle α, the central portions will pass down the central channel 1452, but a doubled central portion will not pass. Similarly, for the application where the tubular braided suture is intended to lock the wide central portion 1805, and 1005, 1599 into the narrower segment 1803 and 1003, and 1598 respectively, the ppi, denier and yarn number for the wider portions are adjusted so that the wide portion taken singly will pass through the central channel 1452, but a doubled wide portion cannot be passed. This is in distinction to sutures used to date in suture locks, where a looped (doubled) wide portion has been passed. In all the above examples, the narrow portion 1803b, 2003, and 1003, 1598 is designed to allow passage when doubled, down the central channel 1452 of the tubular suture The alternatives for filling the inside channel are to pull through a bight of constant-width suture where the doubled cross-section of the bight completely fills the channel, or to pull through a bight of narrow first segment and use that to pull through a single wider second segment of suture that completely fills the channel. In cases where a loop does not actually cross itself or form a complete circle, it maybe referred to as a bight. In the context of this paragraph, loop and bight can mean substantially the same thing. In the first case, one half of the bight is left in the channel, half filling the channel. In the second case, as in FIGS. 16 D and 20 B, for example, a channel-filling suture is left in the channel. In the second case, one can pull a suture into the channel that is approximately twice the cross-section as in the first case. This is because the channel in the first case was used to pass a doubled cross-section of a constant width suture. Therefore the question is to compare the locking friction generated in Chinese-finger-trap type locks, for those two cases.

The first case is where the doubled constant-width suture occupies a fraction of the inner cross-section of the locking channel, 0.95, for example. After the doubled (bight) single suture pulls the attached same single suture into the channel, the fraction of channel cross-section occupied is halved to 0.47, and the diameter occupancy is reduced to 0.68. In the second case, using the variable denier suture, the full sized second segment of the single suture occupies 0.95× the cross section of the locking channel, or 0.97× the available inner diameter of the channel; this is for the case where the first segment is half or less than the denier of the second segment, and does not consider the small additional denier of the traction loop. Clamping force and frictional locking is generated especially with applied axial tension on the suture, according to the principles of a dynamic lock. The calculated increase in frictional force per braid yarn on the 0.97 fill of the diameter is 3 times greater than for the 0.67 diameter fill. With increased fill of the locking channel and associated increased braid angle α, there is an increase in ppi of the locking channel portion, ppi varying as tang. More yarns per inch apply increased force per inch. For the examples given, there is 2.5 times increase in yarns per inch in the 0.95 fill locking portion compared to the 0.47 fill locking portion. The calculated increase in locking force per unit length of locking portion for the examples given is therefore the product of: 3×2.5=7.5. Values in this range are verified experimentally. Therefore, drawing the wider suture into the suture lock with the narrow first segment provides a far superior suture lock.

As described above, a suture can lock within itself in multiple different ways, such as eye splice, a belt splice, and double splices where both ends of the braided structure pass through the same locking channel, but in opposite directions. For example, referring to FIG. 15A, the suture 1501 can be cinched in an eye splice formation such that the traction loop 1595 (and end 1598) is pulled away from the functional suture loop and towards the opposite end 1597 of the suture 1501. Referring to FIG. 15B, the suture 1501 can be cinched in a belt formation such that the traction loop 1595 (and end 1598) is pulled towards the suture loop and away from the opposite end 1597 of the suture 1501.

Figure 22A:
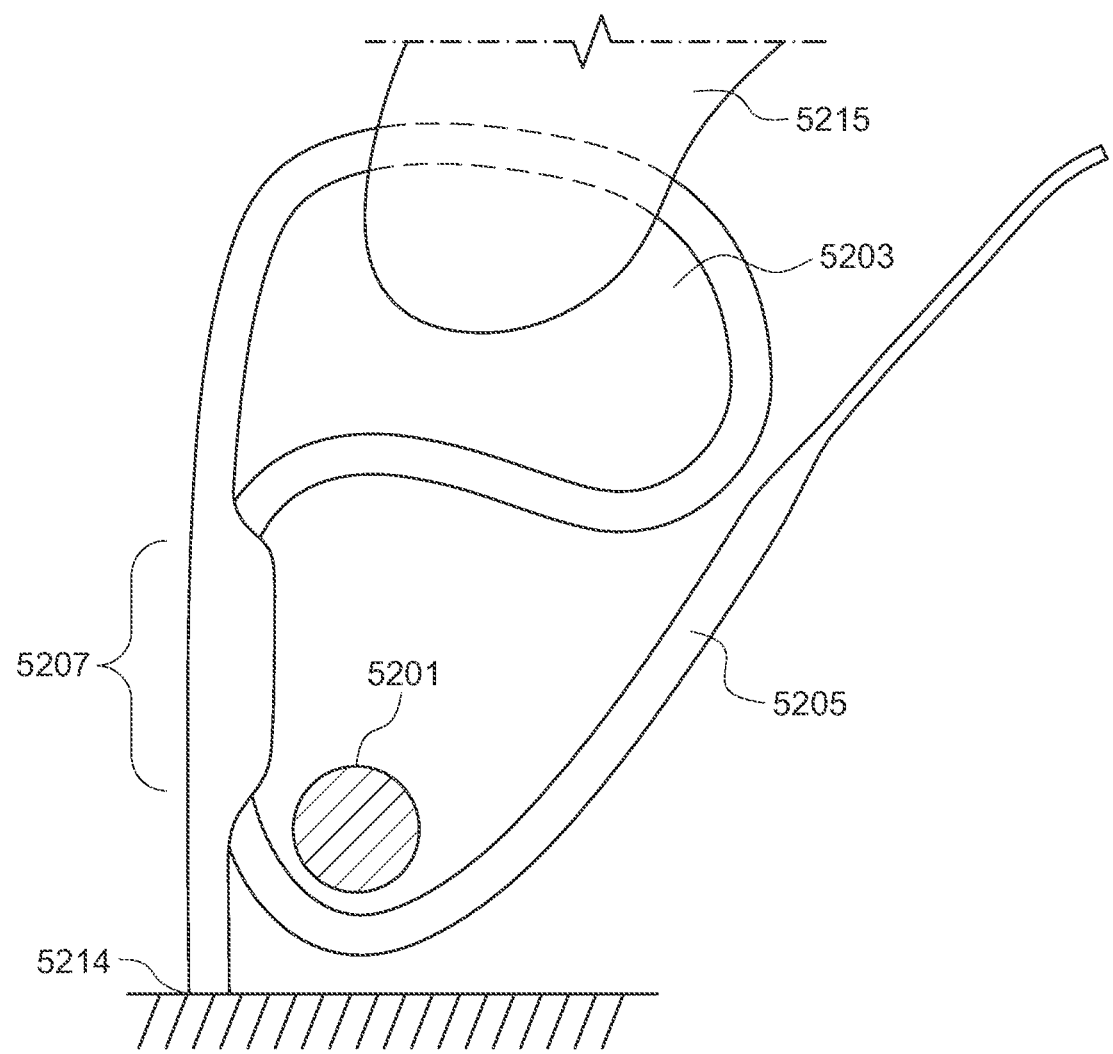
FIGS. 22A-22V show various locking mechanisms.
Figure 22B:
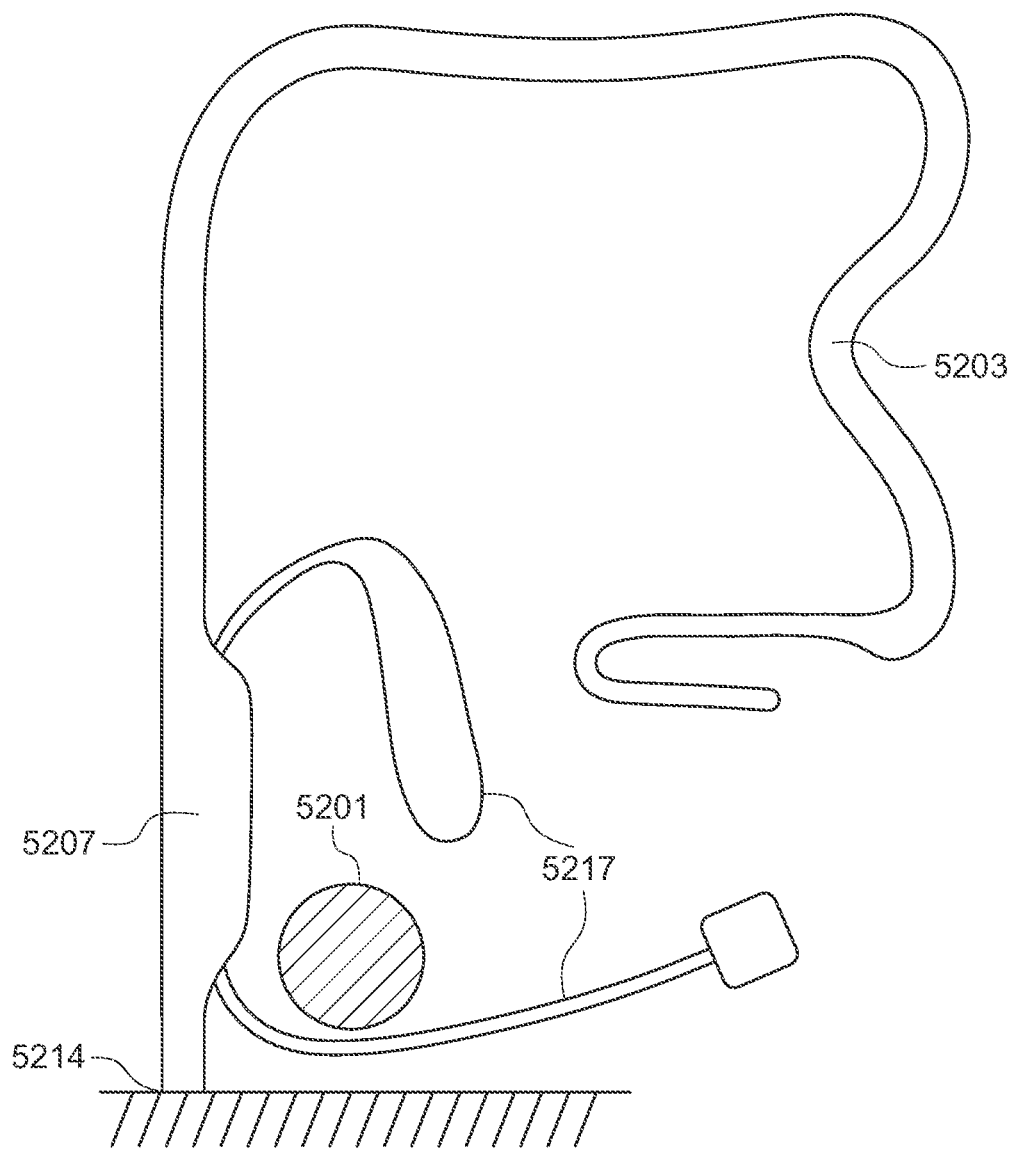

In some embodiments, a pulley, restraint, and or tether can be used to assist in locking a Chinese finger trap-like suture lock such as that described with respect to FIGS. 15A-16D. For example, referring to FIGS. 22A-22B, traction on the loop of the eyesplice 5203 will cause tension on the entire portion of the suture forming the locking channel 5207, greatly enhancing the locking of the Chinese finger trap mechanism. In order for traction on the end of the suture 5205 to cause slippage through the lock and cinching or tensioning of the loop, the suture can be passed around a pulley 5201 so that traction on the suture end (such as with the traction loop 5217 or directly on the end of the suture 5205) causes relaxation of the locking channel, allowing slippage and cinching to occur. This is referred to as a tensionable lock, which can be used to lock the suture within tissue 2215 near a point of attachment 5214.

Figure 22C:
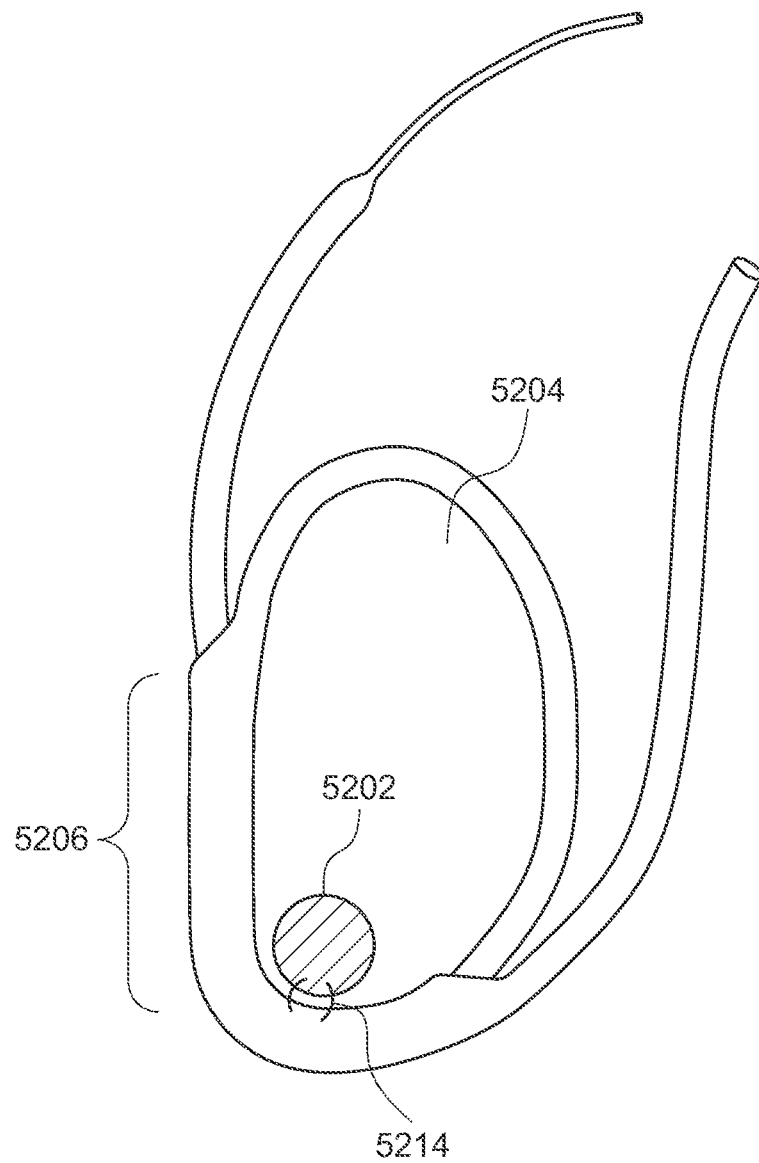
Figure 22D:
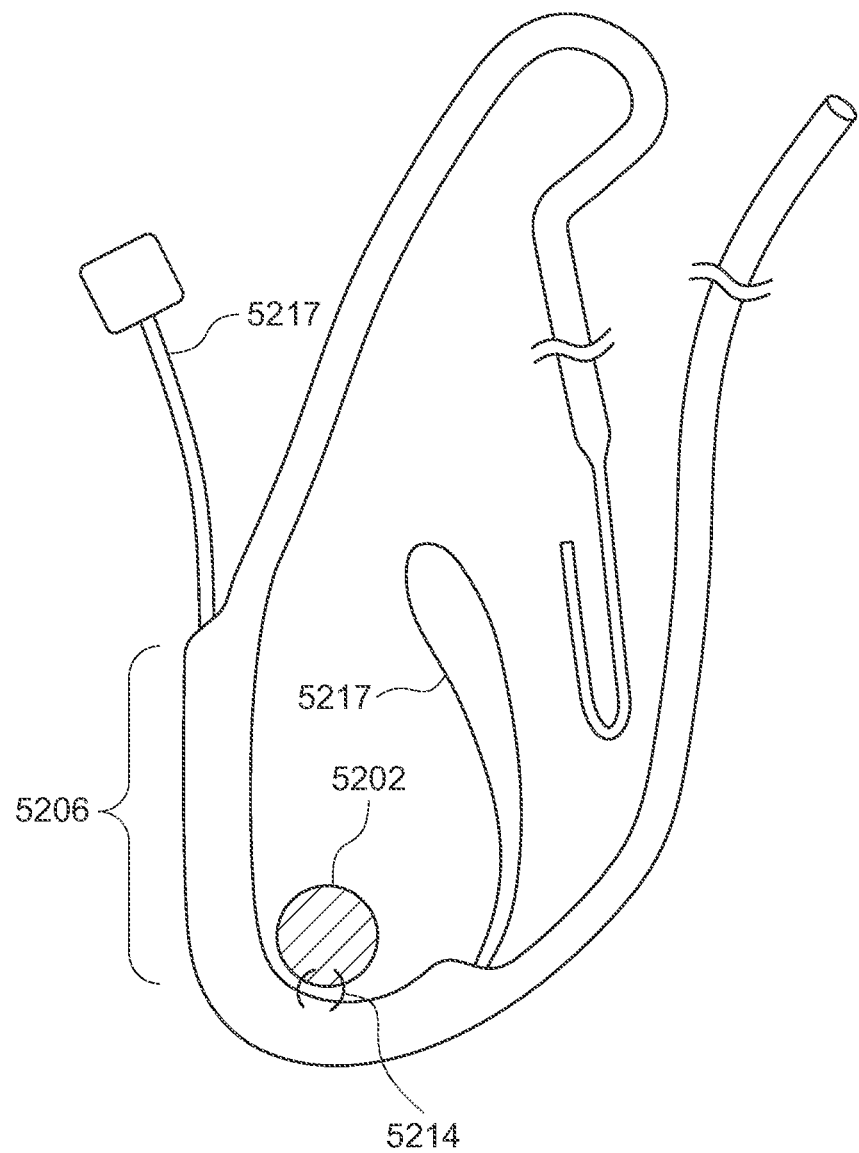

FIGS. 22C-D show a belt-type lock, where tension on the loop 5204 without tension on the suture ends does not fully tension the locking channel. In order to achieve locking here, the locking channel passes around a restraint 5202 functioning partially as a pulley and, the part of the locking portion 5206 from the restraint 5202 constituting the direct connection to the loop is then tensioned fully, allowing more secure locking of the belt-splice. The locking portion 5206 of the suture may be fastened with a tether 5214 or other fastening mechanism to the restraint 5202 to preserve optimal position of the locking portion 5206 relative to the restraint 5202. The near complete fill and friction fit of the second segment in the locking channel reduces the need for axial tension on both ends of the channel to initiate locking.

FIGS. 22E-F show an embodiment of a belt-splice lock where one end of the suture is attached to a fixed point or to a suture anchor. Referring to FIG. 22F, the suture passes from the fixed point 5214 as a tensioning suture segment 5212 through the functioning suture loop 5204 formed by the suture, back round a pulley 5215, then back to where the suture forms the lock portion 5207. From the lock portion 5207 the suture 5213 continues through a tissue 5211 to be repaired, then under the tensioning suture segment 5212, and then into the lock 5207. The free end 5208 projects from the opposite end of the locking channel, and tension is applied to the end to cinch the functioning suture loop 5204. FIG. 22E shows the appearance before the functioning suture loop 5204 is made. The thin first segment free end 5208 is passed through the tissue 5211 to be repaired, then captured by a form of traction loop or tie 5217 that is pre-positioned through the lock portion, also as in FIG. 15A, B. Traction on the traction loop pulls the doubled first portion into the lock portion. A tube or other structure 5209 carrying the traction loop may be positioned in the lock portion, making entry of the knuckle of the doubled first segment into the lock portion easier. Continued traction on the traction loop pulls the tube out as it pulls the first segment into the lock portion. A knot-pusher 5210 can be used to relax tension on the lock portion 5207 as the first then second segments are pulled through the lock portion. The loop 5204 holding tissue may be cinched by applying simultaneous traction on the suture end and applying pressure with the knot pusher. Thus, with the example construct in figures E and F, functional load by tissue 5211 on the belt splice loop 5204 applies tension to the tensioning suture segment 5212, in turn applying tension to the suture 5216 at the end of the locking portion 5207, achieving tension on the locking portion 5207, much as in an eye-splice. This embodiment has further advantages. The loop 5204 can hold the tissue 5211 closer to the fixed point of attachment 5214 than can the loop of the eye splice. The locking can also be greatly enhanced by the use of a variable denier suture because it is possible to achieve complete fill and a friction fit of the second segment in the locking channel. The length of the locking portions 5207 and 5206 can be shorter and still achieve locking, compared to Chinese-finger-trap type locking where variable denier suture is not used. The embodiment shown in FIGS. 22 E and F places the ⅔ of tension on the actual loop 2204, and only ⅓ on the suture 5216 attached to the locking portion 5207.

FIGS. 22G-Q show multiple additional embodiments of belt and eye splices, where the narrow free end 6298 of the suture may be passed through tissue 6215 before being passed through the locking portion 6207 of the suture, and where the loops 6204 of the suture may be cinched and tensioned with traction on the free end 6298. These figures demonstrate various mechanisms for maintaining tension on a locking portion 6207 of a suture having a lower denier end 6298. Using a variable denier suture advantageously provides for easier passing of the free end of the suture, more complete filling of the locking portion, and tighter locking of the loop 6204, similar to as described above. Further, tighter locking resulting from the variable denier suture can allow for use of shorter locking portions 6207 and shorting tissue holding loops 6204. Further, in Figures P,Q,R, S shorter eye splice locking portions 6207 make it possible to draw the repaired tissue 6215 closer to the point of attachment 6214.

Figure 22H:
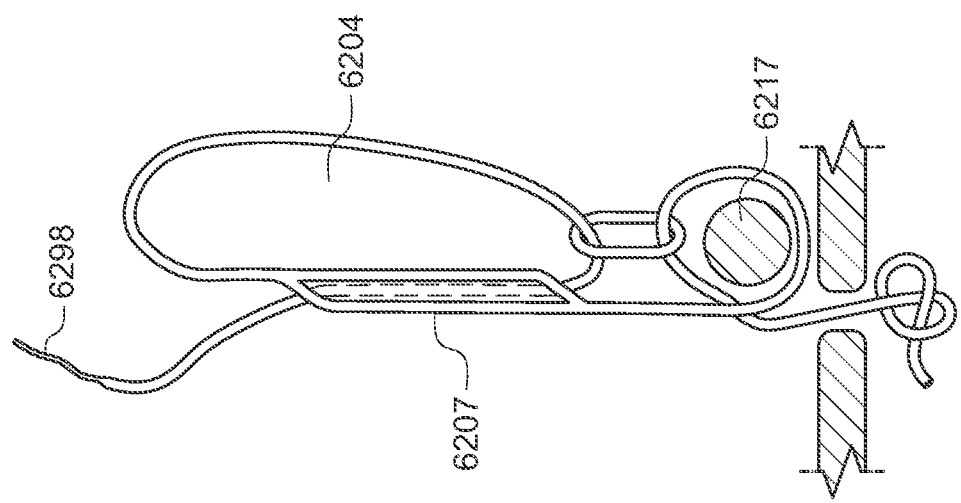
Figure 22G:
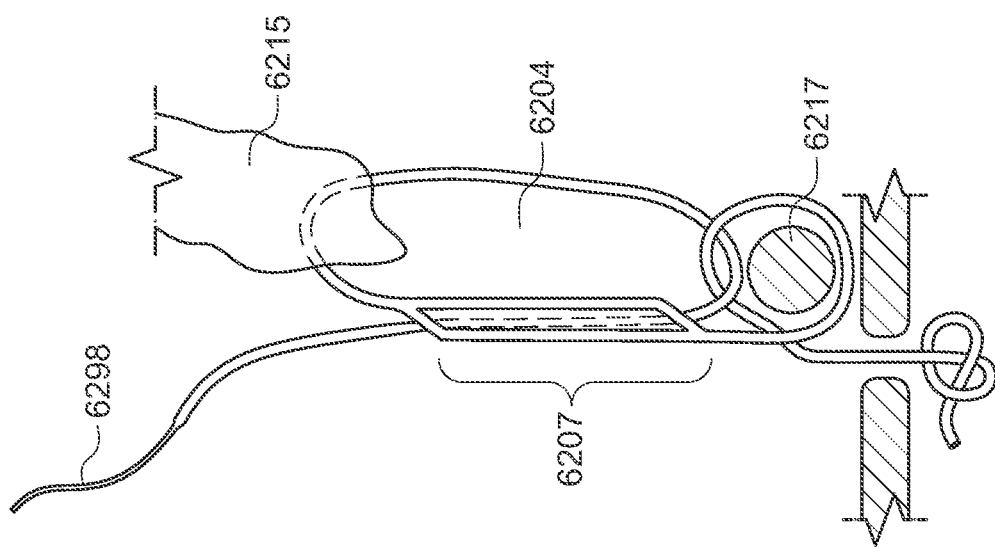
Figure 22J:
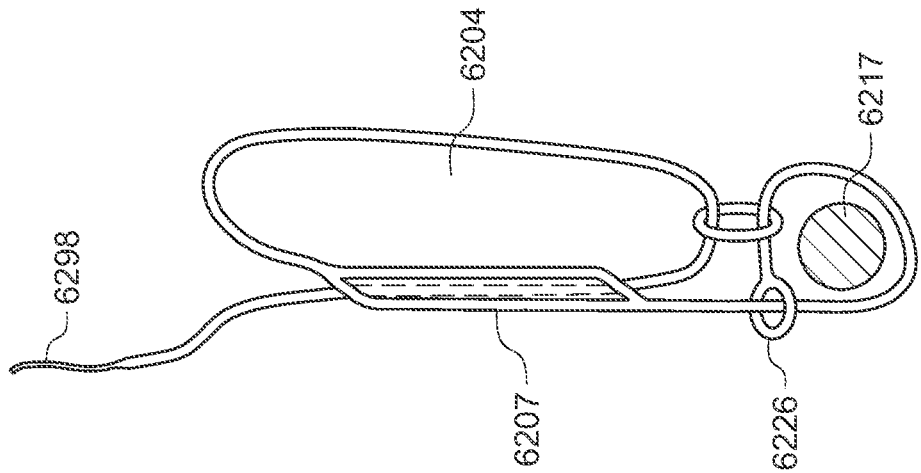
Figure 22I:
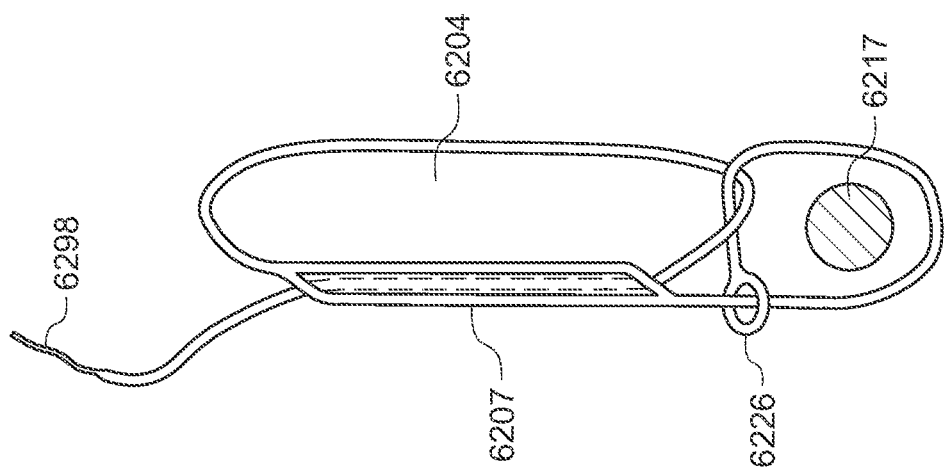
Figure 22L:
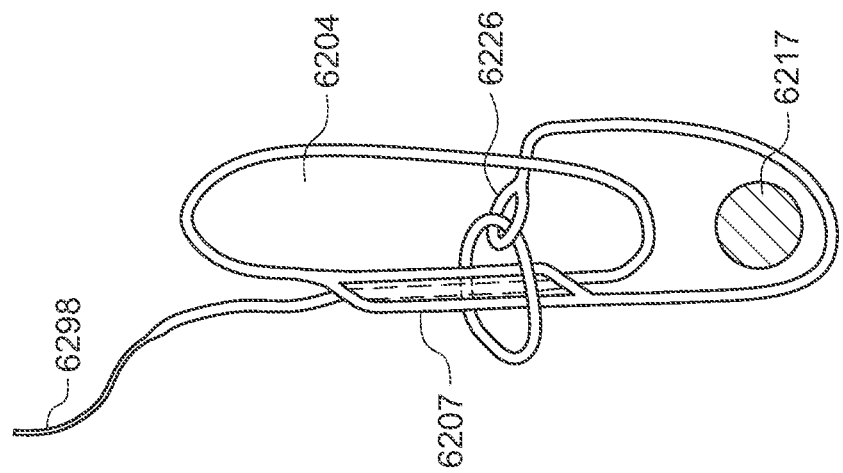
Figure 22K:
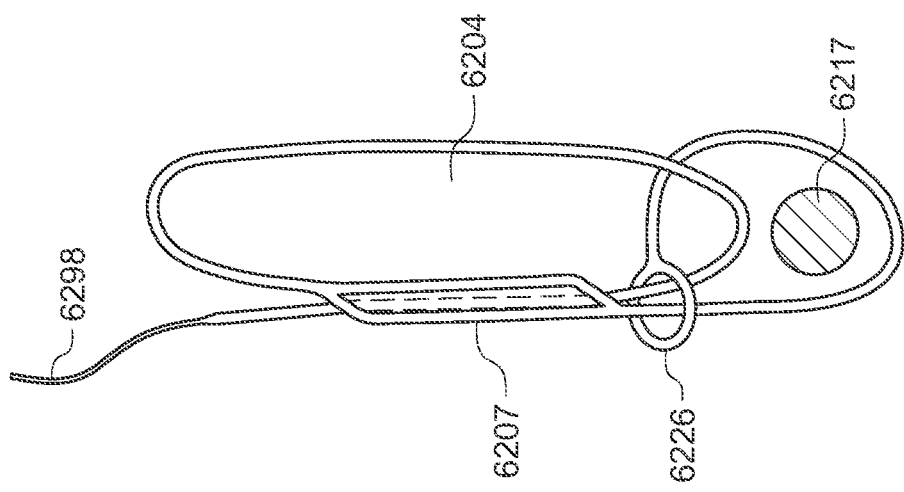
Figure 22N:
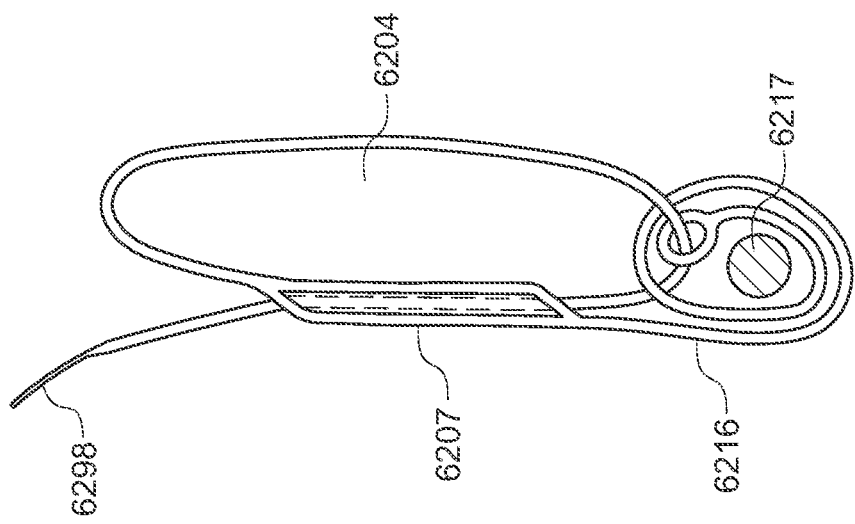
Figure 22M:
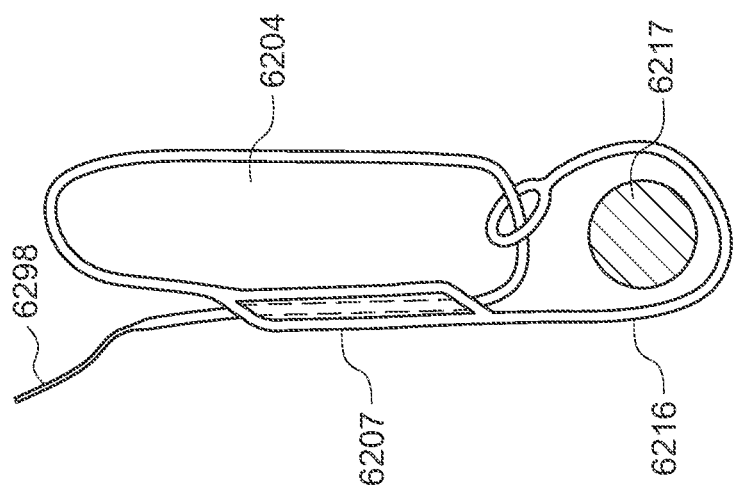
Figure 22O:
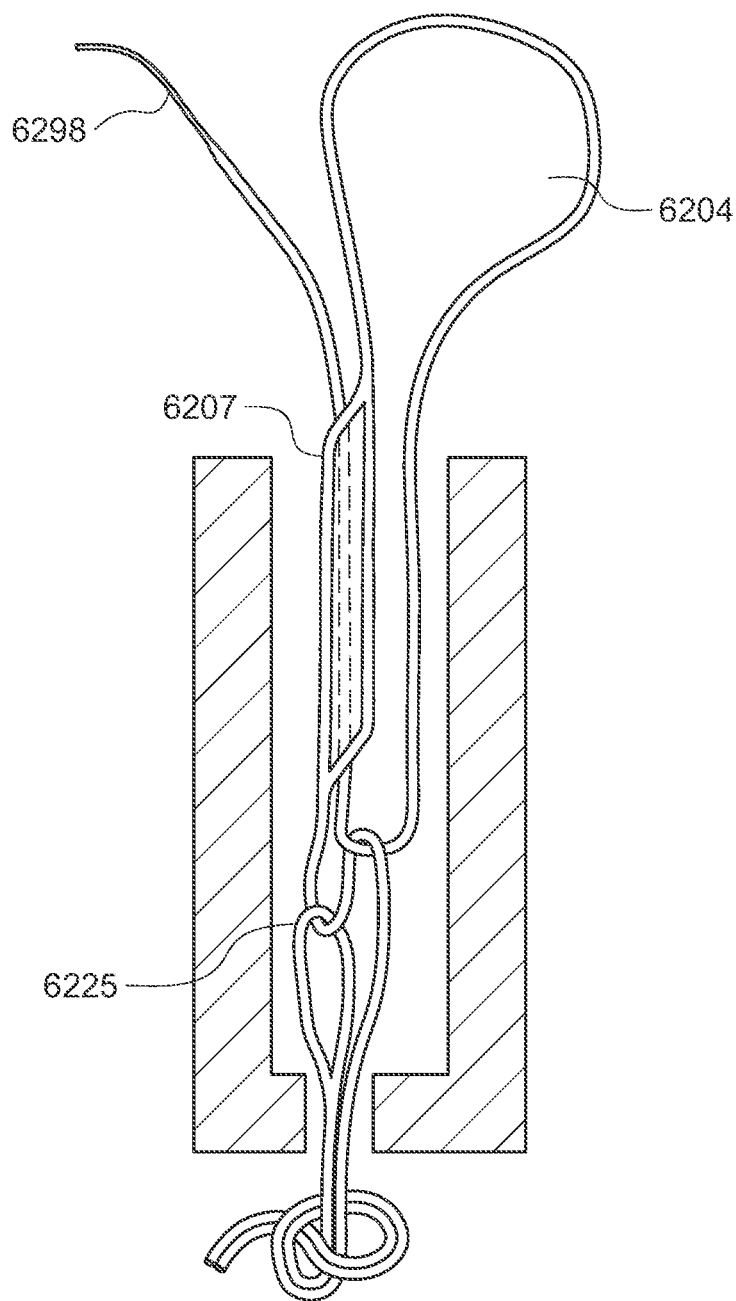
Figure 22Q:
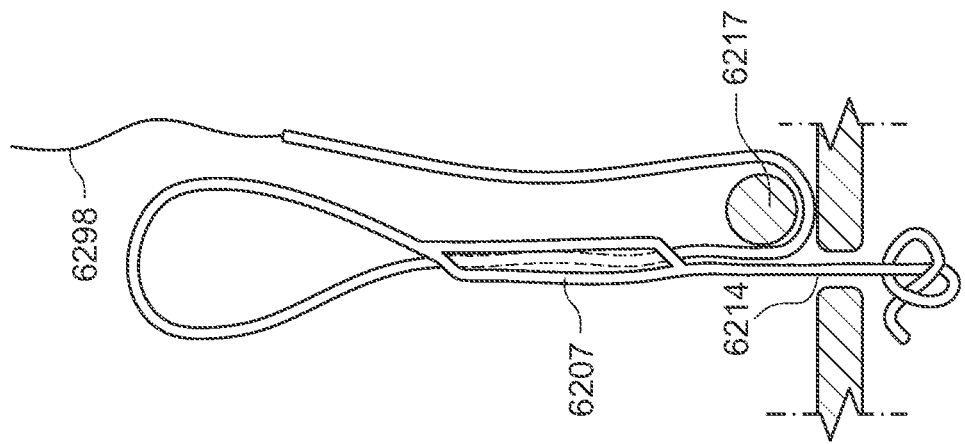
Figure 22P:
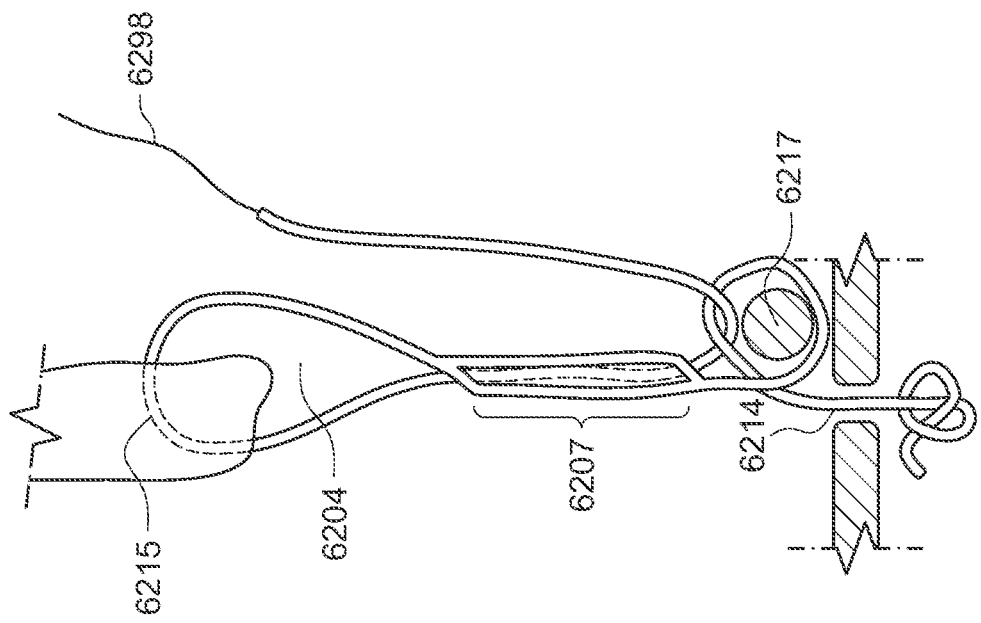
Figure 22S:
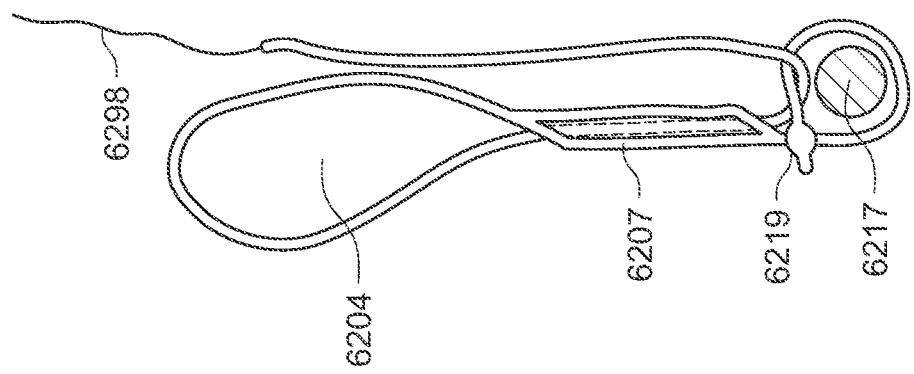
Figure 22R:
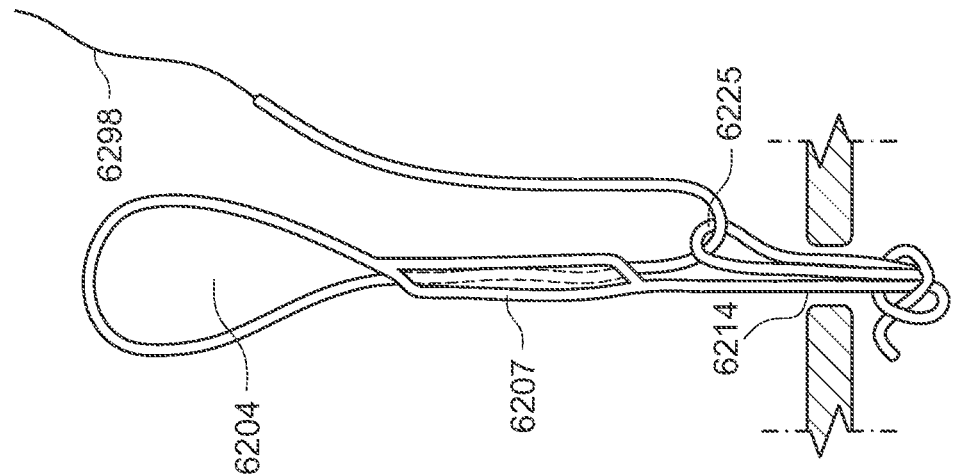

Embodiments in FIGS. 22E, F, G, H, O, P, R, and Q show terminal attachment of the suture in a single location, requiring only a single knot or other means of fixation. FIGS. 22H, J, L, show a supplemental ring of soft or hard material to facilitate the mechanism. In some embodiments, a pulley 6217 or other point of attachment, such as a hard structure or a soft structure (a suture or textile annulus), may be used to assist in locking. FIG. 22N shows a pulley 6217 system reducing the equilibrium tension on the suture 6216 to ¼ the pull on the loop 6204, thereby reducing the side pressure on the opening of the locking channel within the locking portion 6207. This is in contrast to FIG. 22M, where half of applied tension from the loop 6204 is experienced by the suture 6216. FIG. 22O shows how the construct may be recessed into an opening in a suture anchor or other orthopedic implant. Likewise, FIGS. 22O and 22R show how the pulley 6217 may be substituted with a suture 6225. FIG. 22S shows a fixed loop around holding element 6217, where connection 6219 of fixed loop is secure and non-sliding. Connection 6219 may be a knot or where the suture pierces through itself one or more times creating a secure attachment, or a combination thereof. The same method of suture piercing through itself to form secure non-sliding attachment may be facilitated by a thin first segment being pulled through the pierce-hole with a needle, and this method may also be used in place of knots shown. A sliding termination of the suture 6226 is shown in FIGS. 22I, J, K, L, M, N, and this is especially useful when the locking loops are fixed around a single structure 6217. A sliding termination can be facilitated by piercing as above, or by conventional knots such as a bowline or a combination thereof.

Figure 22U:
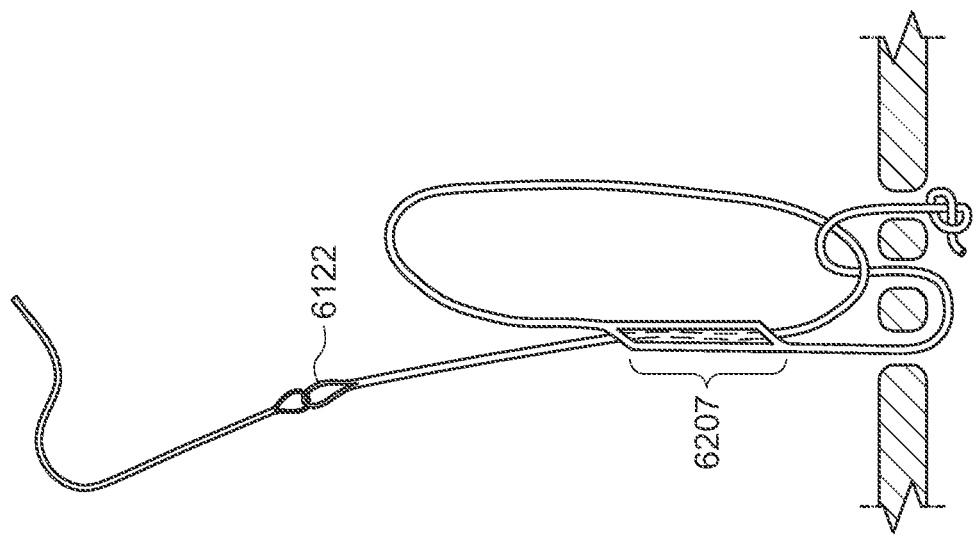
Figure 22T:
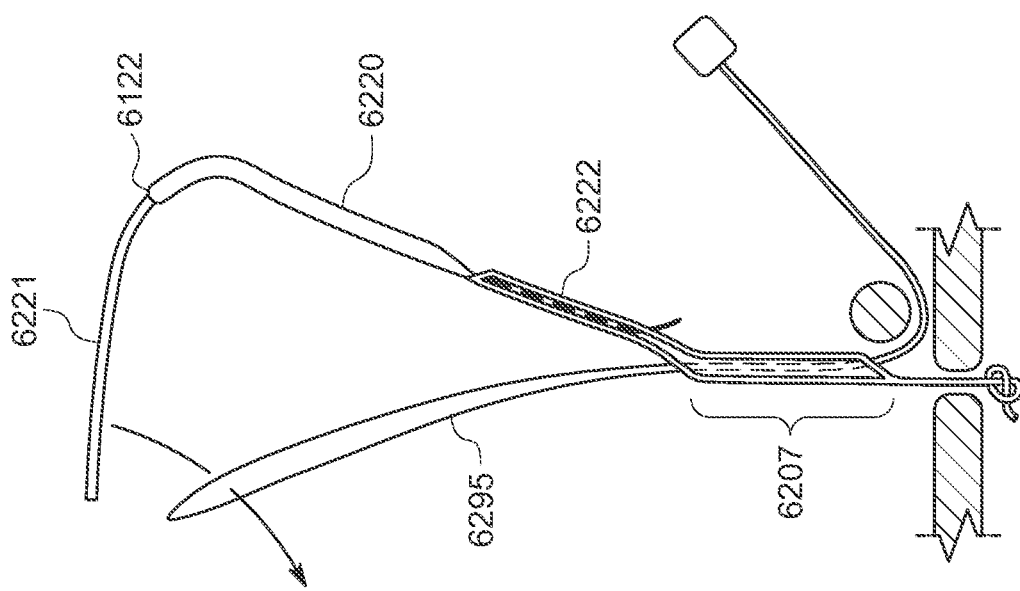
Figure 22V:
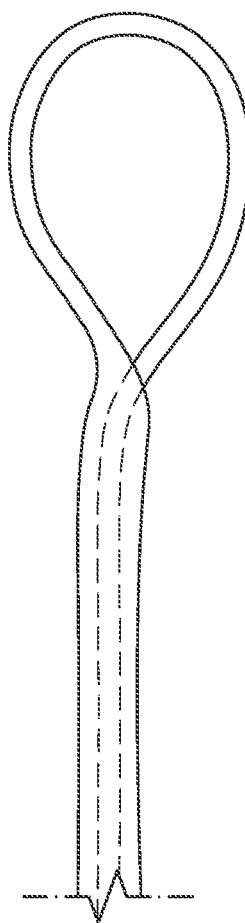

Referring to FIGS. 22T-V, a variable denier suture (such as the suture shown in FIG. 1B) can be locked using an eye splice (shown in FIG. 22T) or a belt splice (shown in FIG. 22U). As shown in FIG. 22T, the free end of the suture 6220 is formed into a loop that is attached to itself at a point 6222 near the locking portion 6207, while a much thinner yarn 6221 forms an opposing bight, this bight forming the end of the variable denier suture. The bights of the sutures 6220, 6221 are joined together at a node 6122 (122 in FIG. 1B). The yarn 6221 is preferably less than half the denier of the yarn 6220. The two arms of the thinner yarn 6221 then function as a lower denier first segment of the suture as described above, while the two arms of the yarn 6220 serve as the higher denier second segment of the suture. The two thin ends of suture 6221 are pulled through the locking portion 6207 using a traction loop 6295.

Referring to FIG. 22U, the bight of the yarn 6220 can be joined to make a loop near the node 6122 by pulling the yarn 6220 coaxially inside of itself over the entire remaining length of the yarn 6220, thereby making a second segment of suture with a loop at the end. As shown in FIG. 22U-V, the locking portion 6207 can be created by pulling one arm of the yarn 6220 down the axis of the other arm, thereby creating a coaxial braid-within-a-braid locking portion 6207, much as is shown in FIG. 15A cross-section.

In FIG. 22 T, the bight 6220 can also be joined at junction 6222, away from the locking portion 6207, such that the locking portion cross-section is as in FIG. 15B. Deniers and picks per inch can be adjusted to achieve optimal locking in much the same way that is described elsewhere in this application. The yarn 6221 may also have one arm drawn down the axis of the other arm, as shown in FIGS. 22U-V, so as to present a single coaxial textile structure 2223 to the surgeon for easier handling. The opposing bights of yarn are each thus joined to make a variable denier suture as in FIG. 22U. Opposing bights of yarn joined at node 6122 may also function as a suture, not having the bights being joined into loops, without departing from this invention.

Figure 18B:
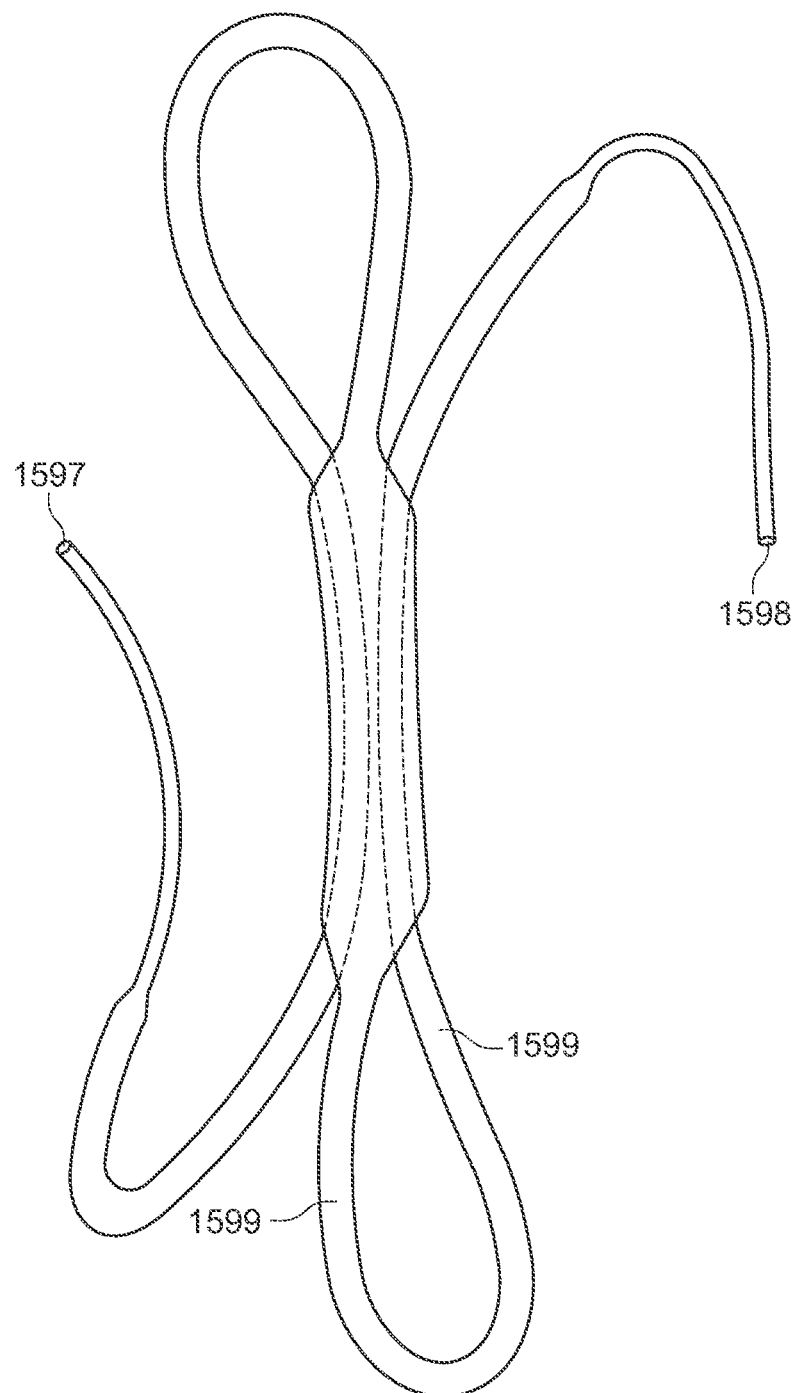

Referring to FIGS. 18A-18B, in some embodiments, both ends 1597, 1598 can be pulled through the channel 1452 in opposite directions. For the case where both ends share locking in at least a portion of the braid, the functioning arms of the loop may extend both from one end of the lock portion (as shown in FIG. 18A), or one arm from either side of the locking portion (as shown in FIG. 18B), as eye-splices. In the case where both arms of one loop extend from one side of the locking portion, each of the two loops may be tightened without relaxing tension on the other loop. In the case where each loop has an arm originating from both ends of the lock, as in FIG. 18A, tightening one loop causes laxity in the other loop, so concurrent tightening with simultaneous traction on the ends is preferred. In FIG. 18, each loop serves to provide tension to the other side of the lock channel as from that loop originates, enhancing the locking effect for the other loop. For optimal hold of the double loop lock, load is carried by both loops. For the case where multiple loops share a single locking portion, the channel cross-section is greater than the channel cross section where the lock holds a single suture. For the case where the lock portion is designed to lock two sutures, the locking portion can pass 2× the denier of the second segment, but less than 3× the denier of the second segment and at least 3× the denier of the first segment. The denier of the first segment can decrease from the second segment by at least ⅓. In this way, when a first segment is passed and un-doubled, the passage is ⅓ occupied. That leaves space for the next doubled ⅔ denier to pass. Once both first segments are passed, that leaves the channel up to ⅔ occupied. Pulling the second segments into the channel then fully occupies the central channel. Where the locking portion is designed to lock two sutures, the sutures may enter the locking portion through separate entry sites as shown in FIG. 18 B, or both sutures may pass through the same entry or exit site.

Figure 18C:
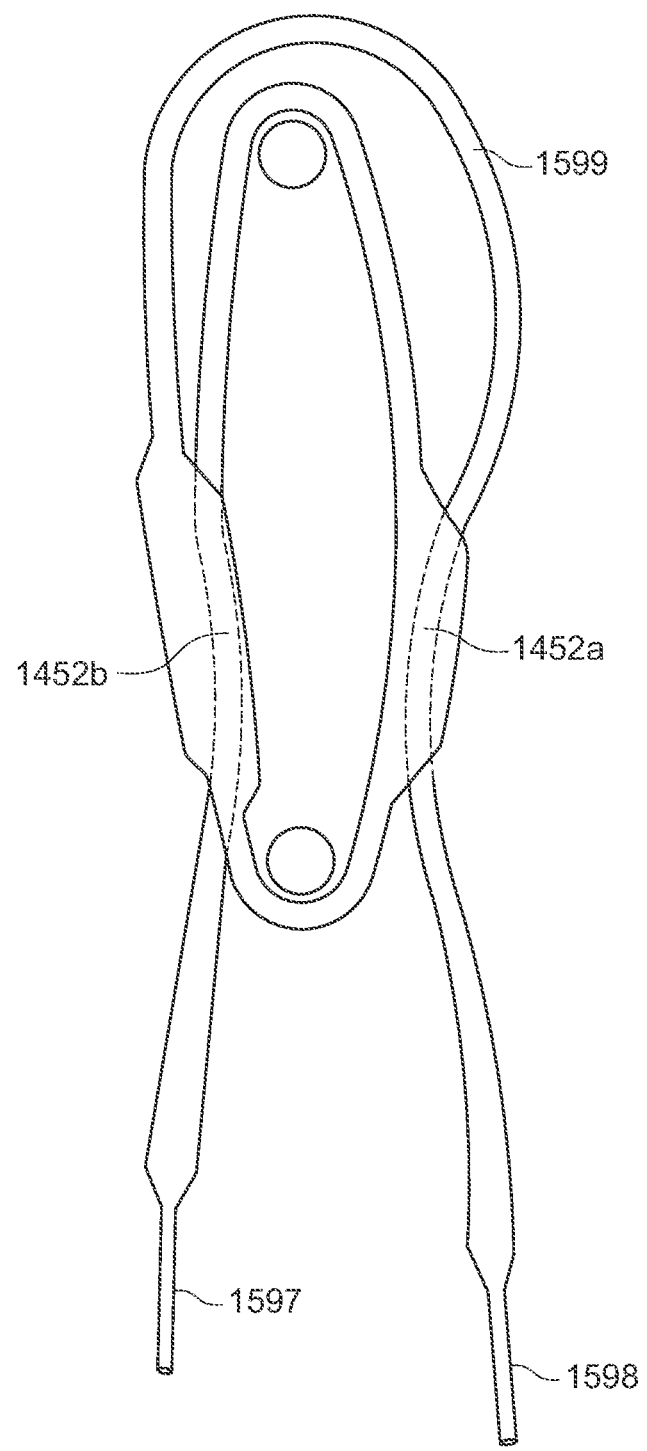

Further, referring to FIG. 18C, in some embodiments, both ends 1597, 1598 can be pulled through separate channels 1452a,b in a suture. Advantageously, by using a double locking mechanism as shown in FIG. 18C, locking can be applied by portions of the suture that have a functional and dynamic tension applied to both ends of the channels 1452 a and b.

The second end 1597 of the suture can also have a reduced diameter segment relative to the central segment 1599.

Figure 20A:
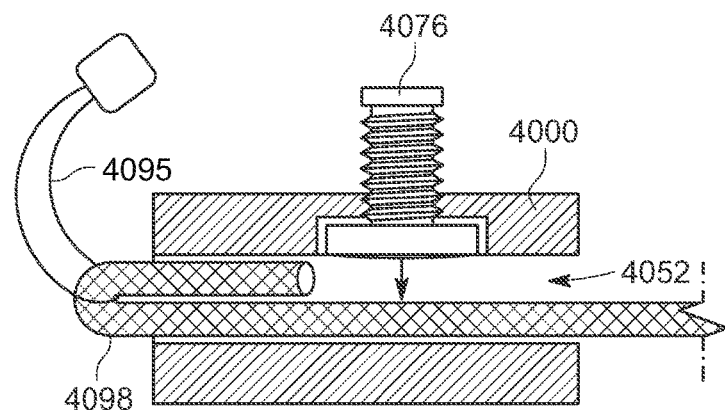
FIGS. 20A-20B show static compression locks.
Figure 20B:
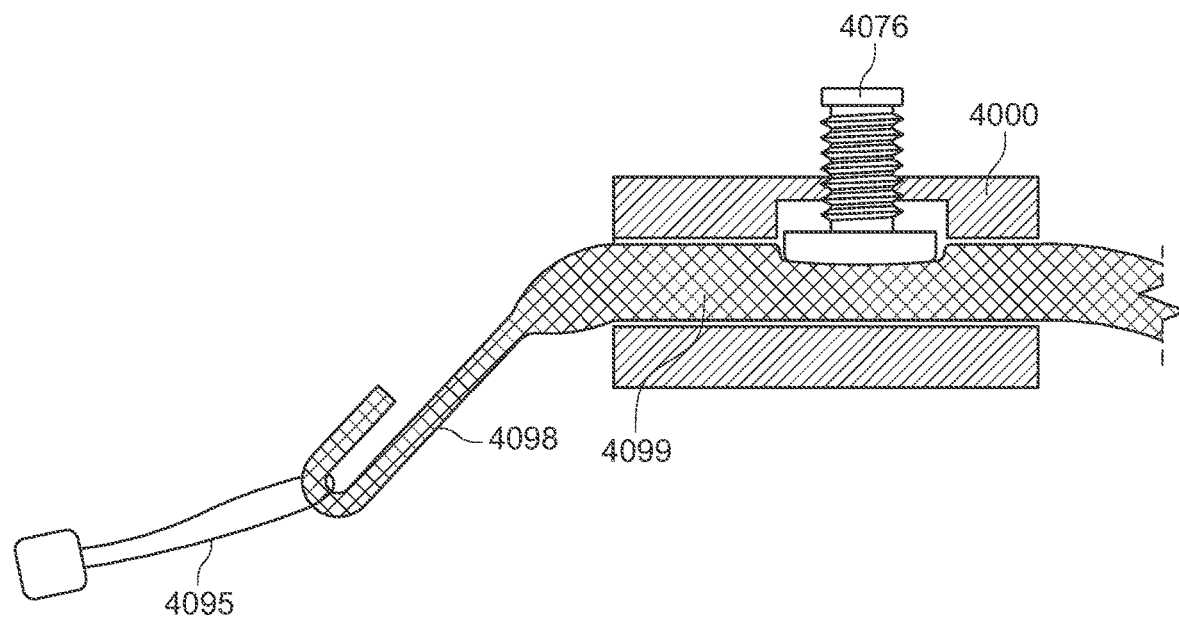
Figure 21:
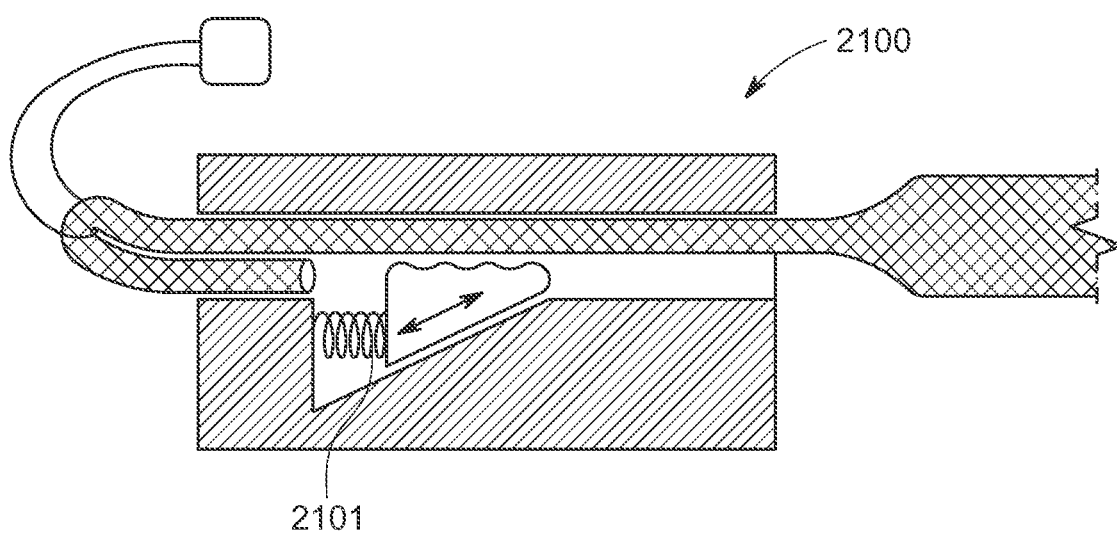
FIG. 21 shows a wedge lock.

Referring to FIGS. 20A-21, the sutures described herein can be advantageously used with other types of suture locks. For example, referring to FIGS. 20A-20B, a multi-denier suture 4001 as described herein can be used with a screw pinch lock 4000. The lower denier segment 4098 can be wrapped around the traction loop 4095 and pulled through the channel 4052 of the screw pinch lock until the higher denier segment 4099 is within the channel 4052. By doing so, the locking screw 4076 has to move a shorter distance to engage against the suture, and the suture 4001 fills more of the channel 4052, thereby enhancing ease of use of the lock 4000 and enhancing the friction effect, and increasing the size and strength of the suture that may be locked and thus the holding force, of the lock 4000. Thus for a given size suture, the size of the suture lock can be reduced. Similarly, a higher denier segment of a suture can advantageously increase the simplicity, space efficiency and usability of the wedge lock 2100 shown in FIG. 21. Moreover, if the cross-section of the passageway through the locks 4000, 2100 is the minimum to allow passage of the single strand of suture, then frictional contact of the locking mechanism against the suture can advantageously be provided without a supplemental biasing mechanism 2101, reducing complexity of the lock.

Figure 24A:
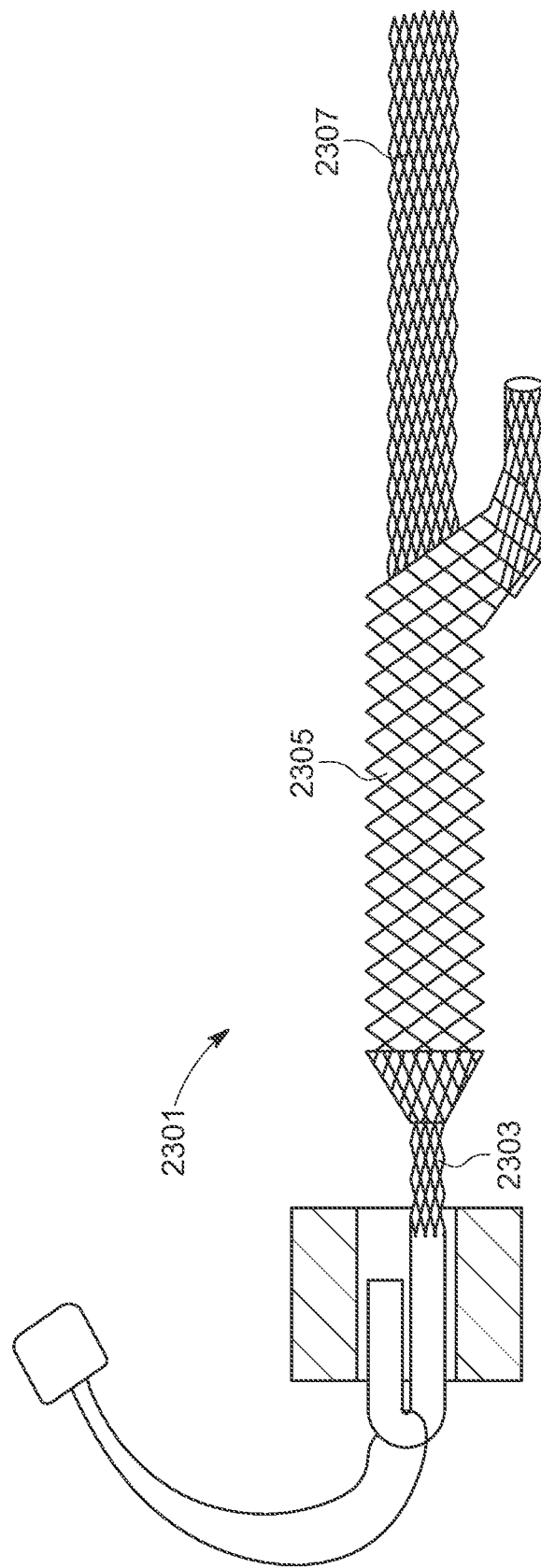

Referring to FIGS. 24A-24B, It is to be understood that the structure 2301 (shown in FIG. 23) can also be used as suture and can lock through the Chinese finger trap-like mechanism (see FIG. 24B) or other suture lock (see FIG. 24A), as described herein for other suture embodiments. During use of the structure 2301 as a suture, the first segment 2303 is pulled through the channel of a suture lock. Once through, the free end is used to pull next the second segment 2305 and then the third segment 2307 to rest in the suture lock. Under certain circumstances, only the second segment 2305 is pulled into the channel of the suture lock. The structure 2301 may be locked in another suture channel lock in the form of a Chinese finger trap. The second and third segments 2305, 2307 may be combined as the locked and locking portions. The structure 2301 may use either the second or third portions of itself as the lock, as shown by the position of outer braid 2384 termination at 3402 or 3403 in the figure. Termination of outer braid 2384 in location 3401 in the figure shows part of the third segment being used as the lock portion, with the third segment also being locked.

The multi-denier sutures described herein can advantageously allow passage of a thinner leading loop through passageways in surgical suture lock passageways, instrument passageways, catheters, and implant passageways. After passage of the thinner loop, traction can be applied to the thin end and the thicker segment of the multi-denier suture is pulled into the passageway, filling or more nearly filling the passageway and enhancing the function and space efficiency of diverse suture locks, instruments, and implants.

As described herein the sutures may be designed for locking in a separate locking mechanism or may be designed for locking within itself with the Chinese-finger-trap locking mechanism. The second segment may be locked in either the first or second segment. For locking in the first segment, the first segment can be designed to have a denier such that the doubled first section will pass easily through its own hollow core with a traction loop, and the single second section denier substantially fills the first segment axial space at near maximal achievable braid angle alpha. The enhanced locking is expected to function even when fill by the second segment is between 50% and 100% of the locking channel. The preferred embodiment is to configure the suture to allow fit of the second segment down the axis of the second segment, and to have the doubled first segment pass easily down the axis of the second segment. Here, the second segment can nearly fill the expanded dimension of the axial space of the second segment, i.e., the axial space of the inner element braid. With second segment locking into second segment, the minimum tensile strength and cross-sectional profile of the locked suture is that of the second segment, whereas with locking of the second segment into the first segment, the thinner first segment defines tensile strength and part of the side-profile against tissue.

The multi-denier sutures described herein can thus be used for knotless locking mechanisms to enhance the space and mechanical efficiency and reduce complexity. Such multi-denier sutures can advantageously enhance locking function, enhance suture lock size efficiency, and reduce design complexity.

The yarns and sutures herein are described as having a denier or multiple denier. It is to be understood that where the phrase "denier" is used, "denier/density" is also applicable, which gives volume/length (where denier is mass/length). That is, for equal suture material, comparison of suture denier or volume/length is the same. The term denier is used above with the assumption that the yarns materials of the compared braids are the same. However, the phrase "denier" can imply "denier/density" above for yarns of the different braids being of different materials. Further, as used herein, passing-cross-section is defined as the greatest suture cross-sectional area that can be pulled through a suture lock with a traction loop. In terms of denier, this corresponds to denier/density of the loop of suture that can be pulled through the lock. Compressed cross-section corresponds to the same number, referring to the denier of the suture, approximately density x cross section of passage, that can be pulled through a hole of given cross-section.

As used herein, a traction loop or passing loop, such as loop 1595 shown FIG. 15A, may be in many different forms. A single braid may be used as passing loop by piercing transversely through the braid, and using the transverse hole as the loop, to pass first segment 1598. A so-called "button hole braid" may be used, where there is a braided window through a continuous braid. The traction loop may be an actual loop as shown in FIG. 15A and elsewhere, or a monofilament with a slit-hole cut transversely through in a plane parallel to the longitudinal axis. Generally, the traction loop is smaller in denier than the element being pulled, and the smallness is limited by the strength requirement of the pulling. In FIGS. 22E and F, the traction loop construct may include a small tube 5209 having similar diameter as the second segment or doubled first segment, such that the locking channel is kept fully open by the tube; the traction loop runs in the lumen of the tube, and as the doubled first segment is pulled into the channel, it butts against the tube-end and pushes the tube ahead of it as it enters and traverses the channel. This reduces the force required to pull the folded first segment into the locking channel 5207. The tube 5209 is discarded along with the traction loop 5217, after use.

FIG. 16B shows another embodiment and fabrication method for making variable denier suture, where some of the yarns or fibers of a braid are terminated along the braid, in the zone of transition from larger denier to smaller denier. Yarns or fibers are terminated individually, without termination of immediately adjacent yarns or fibers, leaving a very smooth transition in denier in an otherwise smooth braided structure. The number of yarns terminated is according to the desired reduction in denier at the transition. This is shown in FIG. 16B for a single yarn, where the black yarn is terminated at the yarn end 1531. This may be achieved in two ways, the first method being by selective automated or manual removal of yarns or fibers from the braid. The individual yarns are picked up from the braid, pulled out of the braid for a distance corresponding to the length of the reduced denier segment, and then cut away. Traction is then applied to the braid, pulling the cut yarn ends back into the remaining braid, and correcting the accordion-effect caused to the braid. The second method is to remove the yarns by chemical dissolution of a fraction of the fibers in the reduced denier segment. For example, the yarns or fibers to be removed in the reduced denier segment can be PET yarns, and the yarns or fibers to be preserved in the reduced denier segment can be polyethylene yarns. The PET yarns can be dissolved away by placing the intended reduced denier segments in solvents including heated phenol, sulfolane, or mixtures of solvents, or in chemical solutions including sodium hydroxide and ammonia. Polypropylene fibers may also be dissolved similarly or otherwise chemically removed, leaving fibers of polyethylene.

Moreover, the structures described herein can be used for other applications. Other possible applications include placement of sutures through an endovascular catheter, a laparoscope, or a thoracoscope or other minimally invasive portals. In another embodiment, a vascular graft is formed from a multi-denier yarn as shown in FIG. 8C. That is, the graft can divide or bifurcate from a singular tubular structure into two or more tubular structures. The graft can be made by continuous seamless braiding, such as with a Herzog VF 1/(4-32)-140 S Variation Braiding Machine.

What is claimed is:

1. A method of suturing, comprising:
    inserting a first end of a suture through a loop wherein the first end of the suture is a first end of a first segment of the suture, wherein the first segment comprises first strands that extend to the first end of the first segment, at least a portion of the first strands braided together in a first braid;
    folding the first segment over to form a doubled first segment, the doubled first segment including the first end of the suture;
    pulling the loop and the doubled first segment through an opening; and
    continuing to pull the first segment through the opening such that a second segment of the suture extends through the opening,
    wherein the second segment comprises second strands and the first strands, at least a portion of the second strands braided together with at least a portion of the first strands in a second braid, wherein the second braid is tubular and continuous with the first braid to form a continuous suture braid along an outermost layer of the suture, wherein there are more strands in the second segment than first strands in the first segment, wherein a second denier of the second segment has greater denier than a first denier of the first segment, and further wherein a total denier of the doubled first segment is less than the second denier of the second segment.

2. The method of claim 1, wherein the second segment fills the opening more than the first segment fills the opening.

3. The method of claim 1, wherein the second segment fills the opening more than the doubled first segment fills the opening.

4. The method of claim 1, wherein as the second segment is pulled through the opening, wherein the opening is an opening in a surgical implant, it fills the opening of the surgical implant, to restrain the suture from movement after completion of a surgical process.

5. The method of claim 1, further comprising, prior to the inserting step, threading the suture through an opening in a surgical instrument and pulling the suture through soft tissue to place a portion of the suture having a higher denier than the first segment, against the soft tissue, wherein the soft tissue is being repaired.

6. The method of claim 5, wherein the portion of the suture having a higher denier than the first segment comprises the second segment.

7. The method of claim 5, wherein the portion of the suture having a higher denier than the first segment comprises a third segment, the third segment having a constant third denier that is different from the first denier and the second denier.

8. The method of claim 5, wherein the portion of the suture having a higher denier than the first segment has a greater side profile than the first segment.

9. The method of claim 1, wherein the opening is an opening in a surgical instrument or an opening in a surgical implant.

10. The method of claim 1, wherein the opening is an opening in a surgical implant, further wherein the surgical implant comprises a suture lock, the suture lock including the opening.

11. The method of claim 1, further comprising, after the continuing step, cutting off the first segment.

12. The method of claim 1, wherein the portion of second strands braided together with at least a portion of the first strands form a braid positioned around an inner element.

13. The method of claim 1, wherein the first denier of the first segment is constant, and the second denier of the second segment is constant.

14. The method of claim 1, wherein a transition zone between the first and second segments comprises ends of the second strands.

15. The method of claim 14, wherein there is a gradual increase in denier in the transition zone.

16. The method of claim 1, wherein the suture further comprises a third segment wherein the third segment has a constant third denier that is different from the first denier and the second denier.

17. The method of claim 16, wherein the third segment is between the first segment and the second segment.

18. The method of claim 16, wherein the constant third denier is greater than the second denier.

19. The method of claim 16, wherein the constant third denier is less than the second denier.

20. The method of claim 16, wherein the suture comprises a transition zone between the first segment and the second segment, wherein the outermost layer of the suture comprises a portion of the second strands braided together in the second braid along the outermost layer of the suture, and further wherein the portion of the second strands braided together in the second braid have ends in the transition zone.

21. The method of claim 1, wherein the first braid is a tubular braid.

22. The method of claim 1, wherein ends of a portion of the second strands are aligned transversely to the axis of the suture to create a sudden change in denier.

23. A method of suturing, comprising:
a first pulling step, wherein a first end of a suture is pulled through tissue,
wherein the suture includes a first segment comprising first strands, and a second segment comprising the first strands and second strands,
wherein the second segment has a denier that is at least two times greater than a denier of the first segment, wherein at least a portion of second strands are braided together to form an outermost layer of the suture, and further wherein in a transition zone between the first segment and the second segment, the outermost layer comprises a plurality of ends of the second strands,
inserting the first segment through a loop after pulling the suture through tissue, wherein the first segment is folded over the loop;
a second pulling step, wherein the folded over first segment is pulled through a first opening with the loop; and
continuing to pull the first segment until the second segment extends through the first opening,
wherein there is an increase in denier of the suture from the first segment to the second segment, as the second segment is pulled into the first opening.

24. The method of claim 23 further comprising,
prior to the first pulling step, threading the suture through a second opening wherein the second opening is an opening in a surgical instrument,
wherein pulling the suture through tissue places a high denier portion of the suture against tissue, and wherein the tissue is soft tissue being repaired.

25. The method of claim 23, wherein the first opening is an opening in a surgical implant, further wherein the surgical implant comprises a suture lock, the suture lock including the first opening.

26. The method of claim 25, wherein the higher denier segment fills the first opening in the suture lock more than the folded over first segment, to restrain the suture from movement after completion of a surgical process.

27. The method of claim 23, wherein the portion of second strands braided together form a braid positioned around an inner element.

28. The method of claim 23, wherein the first and second segments have a constant denier, and wherein the first strands of the suture extend to the first end of the suture.

29. The method of claim 23, wherein the plurality of ends of second strands comprises ends of the strands that are braided together to form the outermost layer of the suture, wherein the outermost layer of the suture comprises a continuous braid extending the entire length of the suture.

30. The method of claim 23, wherein inserting the first segment through a loop comprises inserting a first end of the first segment through the loop, wherein the first end of the first segment is the first end of the suture, further wherein the first strands of the suture extend to the first end of the suture.

31. The method of claim 23, wherein the suture further comprises a third segment between the first and second segments, wherein the third segment has a constant denier that is different from the denier of the first segment and the denier of the second segment.

32. A method of suturing, comprising:
inserting a first end of a suture through a loop, wherein the first end of the suture is a first end of a first segment of the suture, wherein the first segment comprises first strands that extend to the first end of the first segment, at least a portion of the first strands braided together in a first braid;
folding the first segment over the loop, to form a doubled first segment, the doubled first segment including the first end of the suture;
pulling the loop and the doubled first segment through an opening; and
continuing to pull the first segment through the opening, wherein a second segment of the suture extends through the opening,
wherein the second segment has second strands and the first strands, at least a portion of the second strands braided together with at least a portion of the first strands in a second braid, wherein the second braid is tubular and continuous with the first braid to form a continuous suture braid along an outermost layer of the suture, wherein there are more strands in the second segment than first strands in the first segment, and wherein a denier of the second segment is at least twice as great as a denier of the first segment.

33. A method of suturing, comprising:
threading a first segment of a suture through an opening in a surgical instrument, and pulling the suture through tissue,
wherein the suture includes a first segment comprising first strands, and a second segment comprising second strands and the first strands,
wherein the second segment has a greater number of strands than a number of strands of the first segment, wherein at least a portion of the second strands are braided together to form an outermost layer of the suture, and further wherein the second strands terminate in a transition zone between the first segment and the second segment,
inserting the first segment through a loop after the threading step, wherein the first segment is folded over the loop, wherein the folded over first segment, when placed or pulled with a loop through a small opening in a surgical implant, has an equivalent or smaller diameter than the second segment;

pulling the folded over first segment through the opening in the surgical implant with the loop; and continuing to pull the first segment until the second segment extends through the opening in the surgical implant, wherein there is an increase in the number of strands of the suture from the first segment to the second segment, as the second segment is pulled into the opening in the surgical implant.

* * * * *